United States Patent
Kreel et al.

(10) Patent No.: US 10,724,054 B2
(45) Date of Patent: Jul. 28, 2020

(54) USE OF SERINE PROTEASES FOR IMPROVING ETHANOL YIELD

(71) Applicant: NOVOZYMES A/S, Bagsvaerd (DK)

(72) Inventors: Nathaniel Edward Kreel, Louisburg, NC (US); Joseph Jump, Raleigh, NC (US); Melissa Carrie Hooss, Franklinton, NC (US); Madison Roberts, Raleigh, NC (US); Bernardo Vidal, Jr., Wake Forest, NC (US); Kenneth Jensen, Oelsted (DK); Xinyan Guo, Beijing (CN); Henrik Frisner, Frederiksberg C (DK); Tine Hoff, Holte (DK); Ye Liu, Beijing (CN); Lan Tang, Beijing (CN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

(21) Appl. No.: 15/761,579

(22) PCT Filed: Sep. 26, 2016

(86) PCT No.: PCT/CN2016/100090
§ 371 (c)(1),
(2) Date: Mar. 20, 2018

(87) PCT Pub. No.: WO2017/050291
PCT Pub. Date: Mar. 30, 2017

(65) Prior Publication Data
US 2018/0340191 A1 Nov. 29, 2018

Related U.S. Application Data

(60) Provisional application No. 62/232,903, filed on Sep. 25, 2015.

(30) Foreign Application Priority Data

Jul. 1, 2016 (WO) ................ PCT/CN2016/088143

(51) Int. Cl.
| | |
|---|---|
| C12P 7/06 | (2006.01) |
| C12N 9/58 | (2006.01) |
| C12N 9/50 | (2006.01) |
| C12N 9/54 | (2006.01) |
| C12N 15/63 | (2006.01) |
| C12N 9/48 | (2006.01) |
| C12N 9/24 | (2006.01) |
| C13K 1/06 | (2006.01) |

(52) U.S. Cl.
CPC .............. *C12P 7/06* (2013.01); *C12N 9/2402* (2013.01); *C12N 9/48* (2013.01); *C12N 9/50* (2013.01); *C12N 9/54* (2013.01); *C12N 9/58* (2013.01); *C12N 15/63* (2013.01); *C12Y 302/01001* (2013.01); *C12Y 304/14* (2013.01); *C12Y 304/21* (2013.01); *C13K 1/06* (2013.01); *C12P 2203/00* (2013.01); *Y02E 50/17* (2013.01)

(58) Field of Classification Search
CPC ....................................................... C12N 9/16
USPC ........................................................ 435/219
See application file for complete search history.

(56) References Cited

U.S. PATENT DOCUMENTS

| | | | |
|---|---|---|---|
| 5,231,017 A | 7/1993 | Lantero | |
| 7,563,607 B2 * | 7/2009 | Duan | C12N 9/48 435/161 |

FOREIGN PATENT DOCUMENTS

| | | |
|---|---|---|
| WO | 07/145912 A1 | 12/2007 |
| WO | 03/066826 A2 | 8/2008 |
| WO | 2010/008841 A2 | 1/2010 |
| WO | 2013/98185 A1 | 7/2013 |
| WO | 2014/037438 A1 | 3/2014 |
| WO | 2014/205198 A1 | 12/2014 |
| WO | 2015/031477 A1 | 3/2015 |
| WO | 2015/078372 A1 | 6/2015 |

OTHER PUBLICATIONS

Fernandez-Fueyo et al, 2012, Proc Natl Acad Sci U S A 109, 5458-5463.
Fernandez-Fueyo et al, 2013, Uniprot accession No. M2QQ01.
Fernandez-Fueyo et al, 2013, Uniprot accession No. M2QWH2.
Fernandez-Fueyo et al, 2013, Uniprot accession No. M2RD67.
Floudas et al, 2012, Science 336, 1715-1719.
Martinez et al, 2009, Proc Nati Acad Sci U S A 106, 1954-1959.
Martinez et al, 2009, Uniprot accession No. B8P431.
Martinez et al, 2009, Uniprot accession No. B8PMI5.
Wibberg, 2015, NCBI Accession No. CRG91570.1.
Wymelenberg et al, 2006, Uniprot accession No. Q281W2.
Wymelenberg et al, 2006, Fungal Gen Biol 43, 343-356.
Zheng et al, 2014, NCBI Accession No. XP_006668287.1.
WO 2014-037438—Accession No. MER078639.
Guimaraes, 2012, Intech Chapter 20, 1-18.

* cited by examiner

*Primary Examiner* — Tekchand Saidha
(74) *Attorney, Agent, or Firm* — David Fazzolare

(57) ABSTRACT

S53 proteases and the use of S53 protease in processes for converting starch to ethanol are provided.

15 Claims, No Drawings

Specification includes a Sequence Listing.

US 10,724,054 B2

USE OF SERINE PROTEASES FOR IMPROVING ETHANOL YIELD

CROSS-REFERENCE TO RELATED APPLICATIONS

This application is a 35 U.S.C. 371 national application of PCT/CN2016/100090 filed Sep. 26, 2016, which claims priority or the benefit under 35 U.S.C. 119 of International application no. PCT/CN2016/088143 filed Jul. 1, 2016 and U.S. application No. 62/232,903 filed Sep. 25, 2015, the contents of which are fully incorporated herein by reference.

REFERENCE TO SEQUENCE LISTING

This application contains a Sequence Listing in computer readable form. The computer readable form is incorporated herein by reference.

FIELD OF THE INVENTION

The present invention relates to processes for producing fermentation products from gelatinized and/or un-gelatinized starch-containing material.

BACKGROUND OF THE INVENTION

Production of fermentation products, such as ethanol, from starch-containing material is well-known in the art. Generally two different kinds of processes are used. The most commonly used process, often referred to as a "conventional process", includes liquefying gelatinized starch at high temperature using typically a bacterial alpha-amylase, followed by simultaneous saccharification and fermentation carried out in the presence of a glucoamylase and a fermenting organism. Another well-known process, often referred to as a "raw starch hydrolysis"-process (RSH process) includes simultaneously saccharifying and fermenting granular starch below the initial gelatinization temperature typically in the presence of an acid fungal alpha-amylase and a glucoamylase.

U.S. Pat. No. 5,231,017-A discloses the use of an acid fungal protease during ethanol fermentation in a process comprising liquefying gelatinized starch with an alpha-amylase.

WO 2003/066826 discloses a raw starch hydrolysis process (RSH process) carried out on non-cooked mash in the presence of fungal glucoamylase, alpha-amylase and fungal protease.

WO 2007/145912 discloses a process for producing ethanol comprising contacting a slurry comprising granular starch obtained from plant material with an alpha-amylase capable of solubilizing granular starch at a pH of 3.5 to 7.0 and at a temperature below the starch gelatinization temperature for a period of 5 minutes to 24 hours; obtaining a substrate comprising greater than 20% glucose, and fermenting the substrate in the presence of a fermenting organism and starch hydrolyzing enzymes at a temperature between 10° C. and 40° C. for a period of 10 hours to 250 hours. Additional enzymes added during the contacting step may include protease.

WO 2010/008841 discloses processes for producing fermentation products, such as ethanol, from gelatinized as well as un-gelatinized starch-containing material by saccharifying the starch material using at least a glucoamylase and a metalloprotease and fermenting using a yeast organism. Particularly the metallo protease is derived form a strain of *Thermoascus aurantiacus*.

WO 2014/037438 discloses serine proteases derived from *Meripilus giganteus*, *Trametes versicolor*, and *Dichomitus squalens* and their use in animal feed.

WO 2015/078372 discloses serine proteases derived from *Meripilus giganteus*, *Trametes versicolor*, and *Dichomitus squalens* for use in a starch wet milling process.

S53 proteases are known in the art. A S53 peptide from *Grifola frondosa* with accession number MER078639. A S53 protease from *Postia placenta* (Uniprot: B8PMI5) was isolated by Martinez et al in "Genome, transcriptome, and secretome analysis of wood decay fungus *Postia placenta* supports unique mechanisms of lignocellulose conversion", 2009, *Proc. Natl. Acad. Sci. USA* 106:1954-1959.

Vanden Wymelenberg et al. have isolated a S53 protease (Uniprot: Q281W2) in "Computational analysis of the *Phanerochaete chrysosporium* v2.0 genome database and mass spectrometry identification of peptides in ligninolytic cultures reveal complex mixtures of secreted proteins", 2006, *Fungal Genet. Biol.* 43:343-356. Another S53 polypeptide from *Postia placenta* (Uniprot:B8P431) has been identified by Martinez et al. in "Genome, transcriptome, and secretome analysis of wood decay fungus *Postia placenta* supports unique mechanisms of lignocellulose conversion", 2009, *Proc. Natl. Acad. Sci. U.S.A.* 106:1954-1959.

Floudas et al have published the sequence of a S53 protease in "The Paleozoic origin of enzymatic lignin decomposition reconstructed from 31 fungal genomes", 2012, *Science*, 336:1715-1719. Fernandez-Fueyo et al have published the sequences of three serine proteases in "Comparative genomics of *Ceriporiopsis subvermispora* and *Phanerochaete chrysosporium* provide insight into selective ligninolysis", 2012, *Proc Natl Acad Sci USA*. 109:5458-5463 (Uniprot:M2QQ01, Uniprot:M2QWH2, UniprotM2RD67).

It is an object of the present invention to identify proteases that will result in an increased ethanol yield in a starch to ethanol process, when said proteases are added/are present during saccharification and/or fermentation.

SUMMARY OF THE INVENTION

The invention provides in a first aspect a process for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a serine protease belonging to the S53 family.

In a second aspect the invention provides a process for producing a fermentation product from starch-containing material comprising the steps of:
  (a) liquefying starch-containing material in the presence of an alpha-amylase;
  (b) saccharifying the liquefied material obtained in step (a) using a carbohydrate-source generating enzyme;
  (c) fermenting using a fermenting organism;
wherein a serine protease belonging to family 53 is present during step b) and/or c).

In another aspect the present invention provides a polypeptide having serine protease activity, selected from the group consisting of:
  (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 12;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 10.

In another aspect the present invention provides a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 15;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 13.

In another aspect the present invention provides a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the polypeptide of SEQ ID NO: 27;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 25.

In another aspect the present invention provides a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the polypeptide of SEQ ID NO: 31;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 29.

In another aspect the present invention provides a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 38, such as amino acids 195 to 560 of SEQ ID NO: 38 or amino acids 190 to 560 of SEQ ID NO: 38.

In another aspect the present invention provides a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 39, such as amino acids 226 to 647 of SEQ ID NO: 39 or amino acids 221 to 647 of SEQ ID NO: 39.

In another aspect the invention relates to a use of a serine protease, particularly a S53 protease, in a process of fermenting gelatinized and/or un-gelatinized starch-containing material into a fermentation product.

In another aspect the invention relates to a composition comprising a S53 protease and a carbohydrate-source generating enzyme and optionally an alpha-amylase.

In another aspect the invention relates to a polynucleotide encoding the polypeptide of the invention.

In another aspect the invention relates to a nucleic acid construct or expression vector comprising the polynucleotide of the invention operably linked to one or more control sequences that direct the production of the polypeptide in an expression host.

In another aspect the invention relates to a recombinant host cell comprising the polynucleotide of the invention operably linked to one or more control sequences that direct the production of the polypeptide.

Definitions

S53 protease: The term "S53" means a protease activity selected from:

(a) proteases belonging to the EC 3.4.21 enzyme group; and/or (b) proteases belonging to the EC 3.4.14 enzyme group; and/or (c) Serine proteases of the peptidase family S53 that comprises two different types of peptidases: tripeptidyl aminopeptidases (exo-type) and endo-peptidases; as described in 1993, *Biochem. J.* 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 3.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 6.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 9.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 12.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 15.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 27.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 31.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 35.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 38.

In one aspect, the S53 protease have at least 20%, e.g., at least 40%, at least 50%, at least 60%, at least 70%, at least 80%, at least 90%, at least 95%, or at least 100% of the protease activity of the mature polypeptide of SEQ ID NO: 39.

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Catalytic domain: The term "catalytic domain" means the region of an enzyme containing the catalytic machinery of the enzyme.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Endo-protease: Polypeptides having protease activity, or proteases, are sometimes also designated peptidases, proteinases, peptide hydrolases, or proteolytic enzymes. Proteases may be of the exo-type (exopeptidases) that hydrolyse peptides starting at either end thereof, or of the endo-type that act internally in polypeptide chains (endopeptidases).

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more (e.g., several) amino acids absent from the amino and/or carboxyl terminus of a mature polypeptide or domain; wherein the fragment has serine protease activity.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 199 to 564 of SEQ ID NO: 2. Amino acids 1 to 17 of SEQ ID NO: 2 are a signal peptide. In one aspect, the mature polypeptide is amino acids 200 to 565 of SEQ ID NO: 5. Amino acids 1 to 17 of SEQ ID NO: 5 are a signal peptide. In one aspect, the mature polypeptide is amino acids 203 to 567 of SEQ ID NO: 8. Amino acids 1 to 17 of SEQ ID NO: 8 are a signal peptide. In one aspect, the mature polypeptide is amino acids 202 to 567 of SEQ ID NO: 11. Amino acids 1 to 18 of SEQ ID NO: 11 are a signal peptide. In one aspect, the mature polypeptide is amino acids 200 to 565 of SEQ ID NO: 14. Amino acids 1 to 17 of SEQ ID NO: 14 are a signal peptide. In one aspect, the mature polypeptide is amino acids 203 to 565 of SEQ ID NO: 26. Amino acids 1 to 17 of SEQ ID NO: 26 are a signal peptide. In one aspect, the mature polypeptide is amino acids 199 to 565 of SEQ ID NO: 30. Amino acids 1 to 18 of SEQ ID NO: 30 are a signal peptide.

In one aspect, the mature polypeptide is amino acids 209 to 639 of SEQ ID NO: 34. Amino acids 1 to 28 of SEQ ID NO: 34 are a signal peptide. In one aspect, the mature polypeptide is amino acids 195 to 560 of SEQ ID NO: 38. In another aspect the mature polypeptide is amino acids 190 to 560 of SEQ ID NO: 38. Amino acids 1 to 19 of SEQ ID NO: 38 are a signal peptide. In one aspect, the mature polypeptide is amino acids 226 to 647 of SEQ ID NO: 39. In another aspect the mature polypeptide is amino acids 221 to 647 of SEQ ID NO: 39. Amino acids 1 to 16 of SEQ ID NO: 39 are a signal peptide. The N-terminals of the mature S53 polypeptides used according to the present invention were experimentally confirmed based on EDMAN N-terminal sequencing data and Intact MS data. The mature polypeptides are also included as SEQ ID NO: 3 (mature S53 protease 3 from *Meripilus giganteus*), SEQ ID NO: 6 (mature S53 protease from *Trametes versicolor*), SEQ ID NO: 9 (mature S53 protease from *Dichomitus squalens*), SEQ ID NO: 12 (mature S53 protease from *Polyporus arcularius*), SEQ ID NO: 15 (mature S53 protease from *Lenzites betulinus*), SEQ ID NO: 27 (mature S53 protease from *Ganoderma lucidum*), SEQ ID NO: 31 (mature S53 protease from *Neolentinu lepideus*), and SEQ ID NO: 35 (mature S53 protease from *Bacillus* sp. 19138).

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having serine protease activity. In one aspect, the mature polypeptide coding sequence is nucleotides 604 to 1701 of SEQ ID NO: 10 and nucleotides 1 to 54 of SEQ ID NO: 10 encode a signal peptide. In one aspect, the mature polypeptide coding sequence is nucleotides 598 to 1695 of SEQ ID NO: 13 and nucleotides 1 to 51 of SEQ ID NO: 13 encode a signal peptide.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Protease activity: The term "protease activity" means proteolytic activity (EC 3.4). There are several protease activity types such as trypsin-like proteases cleaving at the carboxyterminal side of Arg and Lys residues and chymotrypsin-like proteases cleaving at the carboxyterminal side of hydrophobic amino acid residues. Proteases of the invention are serine endopeptidases (EC 3.4.21) with acidic pH-optimum (pH optimum<pH 7).

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 15, 20, 25, 30, 35, 37, 40, 45, 50, 55, 60, 65, 70, 80, 90, or 95° C. Examples of general protease substrates are casein, bovine serum albumin and haemoglobin. In the classical Anson and Mirsky method, denatured haemoglobin is used as substrate and after the assay incubation with the protease in question, the amount of trichloroacetic acid soluble haemoglobin is determined as a measurement of protease activity (Anson, M. L. and Mirsky, A. E., 1932, *J. Gen. Physiol.* 16: 59 and Anson, M. L., 1938, *J. Gen. Physiol.* 22: 79).

For the purpose of the present invention, protease activity was determined using assays which are described in "Materials and Methods", such as the Kinetic Suc-AAPF-pNA assay, Protazyme AK assay, Kinetic Suc-AAPX-pNA assay and o-Phthaldialdehyde (OPA). For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity.

Sequence identity: The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

$$(\text{Identical Residues} \times 100)/(\text{Length of Alignment} - \text{Total Number of Gaps in Alignment})$$

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

$$(\text{Identical Deoxyribonucleotides} \times 100)/(\text{Length of Alignment} - \text{Total Number of Gaps in Alignment})$$

Stringency conditions: The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more (e.g., several) nucleotides absent from the 5' and/or 3' end of a mature polypeptide coding sequence; wherein the subsequence encodes a fragment having protease activity.

Variant: The term "variant" means a polypeptide having protease activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

DETAILED DESCRIPTION OF THE INVENTION

The present invention relates to serine proteases belonging to family 53 and to processes of producing fermentation products, such as ethanol, from gelatinized as well as ungelatinized starch-containing material using a fermenting organism.

The inventors have found that when using a serine protease of family S53, particularly an endo-protease, such as S53 protease from *Meripilus, Trametes, Dichomitus, Polyporus, Lenzites, Ganoderma, Neolentinus, Lecanicillium, Talaromyces* or *Bacillus*, more particularly *Meripilus giganteus, Trametes versicolor, Dichomitus squalens, Polyporus arcularius, Lenzites betulinus, Ganoderma lucidum, Neolentinus lepideus, Lecanicillium* sp WMM742, *Talaromyces proteolyticus* or *Bacillus* sp. 19138, in a process for producing ethanol from a starch-containing material, the ethanol yield was improved, when the S53 protease was present/or added during saccharification and/or fermentation of either gelatinized or ungelatinized starch.

The proteases used in a process of the invention are selected from the group consisting of:

(a) proteases belonging to the EC 3.4.21 enzyme group; and/or (b) proteases belonging to the EC 3.4.14 enzyme group; and/or (c) Serine proteases of the peptidase family S53 that comprises two different types of peptidases: tripeptidyl aminopeptidases (exo-type) and endo-peptidases; as described in 1993, *Biochem. J.* 290:205-218 and in MEROPS protease database, release, 9.4 (31 Jan. 2011) (www.merops.ac.uk). The database is described in Rawlings, N. D., Barrett, A. J. and Bateman, A., 2010, "MEROPS: the peptidase database", *Nucl. Acids Res.* 38: D227-D233.

For determining whether a given protease is a Serine protease, and a family S53 protease, reference is made to the above Handbook and the principles indicated therein. Such determination can be carried out for all types of proteases, be it naturally occurring or wild-type proteases; or genetically engineered or synthetic proteases.

Peptidase family S53 contains acid-acting endopeptidases and tripeptidyl-peptidases. The residues of the catalytic triad are Glu, Asp, Ser, and there is an additional acidic residue, Asp, in the oxyanion hole. The order of the residues is Glu, Asp, Asp, Ser. The Ser residue is the nucleophile equivalent to Ser in the Asp, His, Ser triad of subtilisin, and the Glu of the triad is a substitute for the general base, His, in subtilisin.

The peptidases of the S53 family tend to be most active at acidic pH (unlike the homologous subtilisins), and this can be attributed to the functional importance of carboxylic residues, notably Asp in the oxyanion hole. The amino acid sequences are not closely similar to those in family S8 (i.e. serine endopeptidase subtilisins and homologues), and this, taken together with the quite different active site residues and the resulting lower pH for maximal activity, provides for a substantial difference to that family. Protein folding of the peptidase unit for members of this family resembles that of subtilisin, having the clan type SB.

Proteases used in a process of the invention are serine proteases of the peptidase family S53.

The proteases used in a process of the invention are acidic proteases with a preference for hydrophobic amino acid residues such as Leu, Tyr, Phe and Met in the P1 position. The proteases have high activity on Suc-Ala-Ala-Pro-Leu-pNA and Suc-Ala-Ala-Pro-Phe-pNA with a broad pH range from 2-5 and retain more than 95% activity after being subjected for 2 hours to pH as low as 3.

In an embodiment, the protease activity is determined using assays described in the "Materials and Methods"-section below, such as the Kinetic Suc-AAPF-pNA assay, Protazyme AK assay, Kinetic Suc-AAPX-pNA assay and o-Phthaldialdehyde (OPA). For the Protazyme AK assay, insoluble Protazyme AK (Azurine-Crosslinked Casein) substrate liberates a blue colour when incubated with the protease and the colour is determined as a measurement of protease activity. For the Suc-AAPF-pNA assay, the colourless Suc-AAPF-pNA substrate liberates yellow paranitroaniline when incubated with the protease and the yellow colour is determined as a measurement of protease activity.

Polypeptides Having S53 Protease Activity

Polypeptides having protease activity, or proteases, are sometimes also designated peptidases, proteinases, peptide hydrolases, or proteolytic enzymes. Proteases may be of the exo-type that hydrolyse peptides starting at either end thereof, or of the endo-type that act internally in polypeptide chains (endopeptidases). Endopeptidases show activity on N- and C-terminally blocked peptide substrates that are relevant for the specificity of the protease in question. For the purpose of the present invention, particularly endoproteases of the S53 family are preferred.

The term "protease" is defined herein as an enzyme that hydrolyses peptide bonds. This definition of protease also applies to the protease-part of the terms "parent protease" and "protease variant," as used herein. The term "protease" includes any enzyme belonging to the EC 3.4 enzyme group (including each of the eighteen subclasses thereof). The EC number refers to Enzyme Nomenclature 1992 from NC-IUBMB, Academic Press, San Diego, Calif., including supplements 1-5 published in 1994, *Eur. J. Biochem.* 223: 1-5; 1995, *Eur. J. Biochem.* 232: 1-6; 1996, *Eur. J. Biochem.* 237: 1-5; 1997, *Eur. J. Biochem.* 250: 1-6; and 1999, Eur. J. *Biochem.* 264: 610-650 respectively. The nomenclature is regularly supplemented and updated; see e.g. the World Wide Web (WWW) at http://www.chem.qmw.ac.uk/iubmb/enzyme/index.html.

The peptidases of the S53 family tend to be most active at acidic pH (unlike the homologous subtilisins), and this can be attributed to the functional importance of carboxylic residues, notably Asp in the oxyanion hole. The amino acid sequences are not closely similar to those in family S8 (i.e. serine endopeptidase subtilisins and homologues), and this, taken together with the quite different active site residues and the resulting lower pH for maximal activity, provides for a substantial difference to that family. Protein folding of the peptidase unit for members of this family resembles that of subtilisin, having the clan type SB.

In an embodiment, the present invention relates to polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, which have protease activity. In one aspect, the polypeptides differ by up to 10 amino acids, e.g., 1, 2, 3, 4, 5, 6, 7, 8, 9, or 10, from the polypeptide of SEQ ID NO: 12.

In a particular embodiment the invention relates to polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 12.

In a particular embodiment the invention relates to polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 12.

In a particular embodiment the invention relates to polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 12.

In a particular embodiment the invention relates to polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 12.

In a particular embodiment the invention relates to polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 12.

In a particular embodiment the invention relates to polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 12.

In a particular embodiment the invention relates to polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 12.

In an embodiment, the present invention relates to polypeptides having a sequence identity to the polypeptide of SEQ ID NO: 15 of at least 92%, at least 93%, at least 94%, at least 95%, at least 96%, at least 97%, at least 98%, at least 99%, or 100%, which have protease activity. In one aspect, the polypeptides differ by up to 10 amino acids, e.g., 1, 2, 3, 4, 5, 6, 7, 8, 9, or 10, from the polypeptide of SEQ ID NO: 15.

In a particular embodiment the invention relates to polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 15.

In a particular embodiment the invention relates to polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 15.

In a particular embodiment the invention relates to polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 15.

In a particular embodiment the invention relates to polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 15.

In a particular embodiment the invention relates to polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 15.

In a particular embodiment the invention relates to polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 15.

In a particular embodiment the invention relates to polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 15.

In an embodiment, the present invention relates to polypeptides having a sequence identity to the polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, which have protease activity. In one aspect, the polypeptides differ by up to 10 amino acids, e.g., 1, 2, 3, 4, 5, 6, 7, 8, 9, or 10, from the polypeptide of SEQ ID NO: 27.

In a particular embodiment the invention relates to polypeptides having a sequence identity to the mature polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 27.

In a particular embodiment the invention relates to polypeptides having a sequence identity to the mature polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 27.

In a particular embodiment the invention relates to polypeptides having a sequence identity to the polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 27.

In a particular embodiment the invention relates to polypeptides having a sequence identity to the mature polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 27.

In a particular embodiment the invention relates to polypeptides having a sequence identity to the mature polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 27.

In a particular embodiment the invention relates to polypeptides having a sequence identity to the polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 27.

In a particular embodiment the invention relates to polypeptides having a sequence identity to the polypeptide of SEQ ID NO: 27 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 27.

In an embodiment, the present invention relates to polypeptides having a sequence identity to the polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, which have protease activity. In one aspect, the polypeptides differ by up to 10 amino acids, e.g., 1, 2, 3, 4, 5, 6, 7, 8, 9, or 10, from the polypeptide of SEQ ID NO: 31.

In a particular embodiment the invention relates to polypeptides having a sequence identity to the mature polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 31.

In a particular embodiment the invention relates to polypeptides having a sequence identity to the mature polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 31.

In a particular embodiment the invention relates to polypeptides having a sequence identity to the polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 31.

In a particular embodiment the invention relates to polypeptides having a sequence identity to the mature polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 31.

In a particular embodiment the invention relates to polypeptides having a sequence identity to the mature polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 31.

In a particular embodiment the invention relates to polypeptides having a sequence identity to the polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 31.

In a particular embodiment the invention relates to polypeptides having a sequence identity to the polypeptide of SEQ ID NO: 31 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 31.

In a particular embodiment the invention relates to polypeptides having a sequence identity to the polypeptide of amino acids 195 to 560 or amino acids 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 195 to 560 of SEQ ID NO: 38 or amino acids 190 to 560 of SEQ ID NO: 38.

In a particular embodiment the invention relates to polypeptides having a sequence identity to the polypeptide of amino acids 195 to 560 or amino acids 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 195 to 560 of SEQ ID NO: 38 or amino acids 190 to 560 of SEQ ID NO: 38.

In a particular embodiment the invention relates to polypeptides having a sequence identity to the polypeptide of amino acids 195 to 560 or amino acids 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 195 to 560 of SEQ ID NO: 38 or amino acids 190 to 560 of SEQ ID NO: 38.

In a particular embodiment the invention relates to polypeptides having a sequence identity to the polypeptide of amino acids 195 to 560 or amino acids 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 195 to 560 of SEQ ID NO: 38 or amino acids 190 to 560 of SEQ ID NO: 38 or amino acids 190 to 560 of SEQ ID NO: 38.

In a particular embodiment the invention relates to polypeptides having a sequence identity to the polypeptide of amino acids 195 to 560 or amino acids 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 195 to 560 of SEQ ID NO: 38 or amino acids 190 to 560 of SEQ ID NO: 38.

In a particular embodiment the invention relates to polypeptides having a sequence identity to the polypeptide of amino acids 195 to 560 or amino acids 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 195 to 560 of SEQ ID NO: 38 or amino acids 190 to 560 of SEQ ID NO: 38.

In a particular embodiment the invention relates to polypeptides having a sequence identity to the polypeptide of amino acids 195 to 560 or amino acids 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 195 to 560 of SEQ ID NO: 38 or amino acids 190 to 560 of SEQ ID NO: 38.

In a particular embodiment the invention relates to polypeptides having a sequence identity to the polypeptide of amino acids 226 to 647 or amino acids 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 226 to 647 SEQ ID NO: 39 or amino acids 221 to 647 of SEQ ID NO: 39.

In a particular embodiment the invention relates to polypeptides having a sequence identity to the polypeptide of amino acids 226 to 647 or amino acids 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 226 to 647 SEQ ID NO: 39 or amino acids 221 to 647 of SEQ ID NO: 39.

In a particular embodiment the invention relates to polypeptides having a sequence identity to the polypeptide of amino acids 226 to 647 or amino acids 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 226 to 647 SEQ ID NO: 39 or amino acids 221 to 647 of SEQ ID NO: 39.

In a particular embodiment the invention relates to polypeptides having a sequence identity to the polypeptide of amino acids 226 to 647 or amino acids 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 226 to 647 SEQ ID NO: 39 or amino acids 221 to 647 of SEQ ID NO: 39.

In a particular embodiment the invention relates to polypeptides having a sequence identity to the polypeptide of amino acids 226 to 647 or amino acids 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 226 to 647 SEQ ID NO: 39 or amino acids 221 to 647 of SEQ ID NO: 39.

In a particular embodiment the invention relates to polypeptides having a sequence identity to the polypeptide of amino acids 226 to 647 or amino acids 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 226 to 647 SEQ ID NO: 39 or amino acids 221 to 647 of SEQ ID NO: 39.

In a particular embodiment the invention relates to polypeptides having a sequence identity to the polypeptide of amino acids 226 to 647 or amino acids 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 226 to 647 SEQ ID NO: 39 or amino acids 221 to 647 of SEQ ID NO: 39.

In an embodiment, the polypeptide has been isolated. A polypeptide of the present invention preferably comprises or consists of the amino acid sequence of SEQ ID NO: 11 or an allelic variant thereof; or is a fragment thereof having protease activity. In another aspect, the polypeptide comprises or consists of the mature polypeptide of SEQ ID NO: 11. In another aspect, the polypeptide comprises or consists of amino acids 202 to 567 of SEQ ID NO: 11.

In an embodiment, the polypeptide has been isolated. A polypeptide of the present invention preferably comprises or consists of the amino acid sequence of SEQ ID NO: 14 or an allelic variant thereof; or is a fragment thereof having protease activity. In another aspect, the polypeptide comprises or consists of the mature polypeptide of SEQ ID NO: 14. In another aspect, the polypeptide comprises or consists of amino acids 200 to 565 of SEQ ID NO: 14.

In an embodiment, the polypeptide has been isolated. A polypeptide of the present invention preferably comprises or consists of the amino acid sequence of SEQ ID NO: 26 or an allelic variant thereof; or is a fragment thereof having protease activity. In another aspect, the polypeptide comprises or consists of the mature polypeptide of SEQ ID NO: 26. In another aspect, the polypeptide comprises or consists of amino acids 203 to 565 of SEQ ID NO: 26.

In an embodiment, the polypeptide has been isolated. A polypeptide of the present invention preferably comprises or consists of the amino acid sequence of SEQ ID NO: 38 or an allelic variant thereof; or is a fragment thereof having protease activity. In another aspect, the polypeptide comprises or consists of the mature polypeptide of SEQ ID NO: 38. In another aspect, the polypeptide comprises or consists of amino acids 195 to 560 of SEQ ID NO: 38.

In an embodiment, the polypeptide has been isolated. A polypeptide of the present invention preferably comprises or consists of the amino acid sequence of SEQ ID NO: 39 or an allelic variant thereof; or is a fragment thereof having protease activity. In another aspect, the polypeptide comprises or consists of the mature polypeptide of SEQ ID NO: 39. In another aspect, the polypeptide comprises or consists of amino acids 226 to 647 of SEQ ID NO: 39.

In an embodiment, the polypeptide has been isolated. A polypeptide of the present invention preferably comprises or consists of the amino acid sequence of SEQ ID NO: 30 or an allelic variant thereof; or is a fragment thereof having protease activity. In another aspect, the polypeptide comprises or consists of the mature polypeptide of SEQ ID NO: 30. In another aspect, the polypeptide comprises or consists of amino acids 209 to 639 of SEQ ID NO: 34. In another embodiment, the present invention relates to a polypeptide having protease activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 10, (ii) or the full-length complement of (i) (Sambrook et al., 1989, *Molecular Cloning, A Laboratory Manual,* 2d edition, Cold Spring Harbor, New York). In an embodiment, the polypeptide has been isolated.

In another embodiment, the present invention relates to a polypeptide having protease activity encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 13, (ii) or the full-length complement of (i) (Sambrook et al., 1989, *Molecular Cloning, A Laboratory Manual,* 2d edition, Cold Spring Harbor, New York). In an embodiment, the polypeptide has been isolated.

The polynucleotide of SEQ ID NO: 10, 13, 25, 29 or a subsequence thereof, as well as the polypeptide of SEQ ID NO: 11, 14, 26, 30 or a fragment thereof may be used to design nucleic acid probes to identify and clone DNA encoding polypeptides having protease activity from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin).

A genomic DNA or cDNA library prepared from such other strains may be screened for DNA that hybridizes with the probes described above and encodes a polypeptide having proteaseactivity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 4, 7, 10, 13 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, 4, 7, 10, 13; or (ii) the mature polypeptide coding sequence of SEQ ID NO: 1, 4, 7, 10, 13; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In another embodiment, the present invention relates to an polypeptide having protease activity encoded by a polynucleotide having a sequence identity to the mature polypeptide coding sequence of SEQ ID NO: 10, of at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having protease activity encoded by a polynucleotide having a sequence identity to the mature polypeptide coding sequence of SEQ ID NO: 13, of at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having protease activity encoded by a polynucleotide having a sequence identity to the mature polypeptide coding sequence of SEQ ID NO: 25, of at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to a polypeptide having protease activity encoded by a polynucleotide having a sequence identity to the mature polypeptide coding sequence of SEQ ID NO: 29, of at least 90%, at least 91%, at least 92%, at least 93%, at least 94%, at least 95%, at least 96%, at least 97%, at least 98%, at least 99%, or 100%. In a further embodiment, the polypeptide has been isolated.

In another embodiment, the present invention relates to variants of the polypeptide of SEQ ID NO: 12, 15, 27, 31 comprising a substitution, deletion, and/or insertion at one or more (e.g., several) positions. In an embodiment, the number of amino acid substitutions, deletions and/or insertions introduced into the polypeptide of SEQ ID NO: 12, 15, 27, 31 is up to 10, e.g., 1, 2, 3, 4, 5, 6, 7, 8, 9, or 10. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a polyhistidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant molecules are tested for [enzyme] activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Serine Protease Activity

In one aspect, the polypeptide is from a strain of the genus *Meripilus, Trametes, Dichomitus, Polyporus, Lenzites, Ganoderma, Neolentinus* or *Bacillus*, more particularly *Meripilus giganteus, Trametes versicolor, Dichomitus squalens, Polyporus arcularius, Lenzites betulinus, Ganoderma lucidum, Neolentinus lepideus,* or *Bacillus* sp. 19138.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Polynucleotides

The present invention also relates to polynucleotides encoding a polypeptide of the present invention, as described herein. In an embodiment, the polynucleotide has been isolated. The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of [Genus], or a related organism and thus, for example, may be an allelic or species variant of the polypeptide encoding region of the polynucleotide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. In a particular embodiment at least one control sequence is exogenous from at least one control sequence normally associated with the naturally occurring gene sequence encoding the S53 family proteases of the present invention.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof. Other promoters are described in U.S. Pat. No. 6,011,147.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* xylanase I, *Trichoderma reesei* xylanase II, *Trichoderma reesei* xylanase III, *Trichoderma reesei* beta-xylosidase, and *Trichoderma reesei* translation elongation factor.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of origins of replication useful in a filamentous fungal cell are AMA1 and ANS1 (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells (non-naturally occurring), comprising a polynucleotide of the present invention operably linked to one or more control sequences that direct the production of a polypeptide of the present invention. A nucleic acid construct or expression vector comprising a polynucleotide of the invention is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the *Fungi imperfecti* (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell. For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningii*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N.

and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides [edit according to the biological activity of the polypeptide]. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Enzyme Compositions

The present invention also relates to compositions comprising an S53 protease. Preferably, the compositions are enriched in such a polypeptide. The term "enriched" indicates that the pullulanase activity of the composition has been increased, e.g., with an enrichment factor of at least 1.1.

The compositions may comprise the S53 protease as the major enzymatic component, e.g., a mono-component composition. Alternatively, the compositions may comprise multiple enzymatic activities, such as the S53 protease and one or more (e.g., several) enzymes selected from the group consisting of hydrolase, isomerase, ligase, lyase, oxidoreductase, or transferase, e.g., an alpha-galactosidase, alpha-glucosidase, aminopeptidase, alpha-amylase, beta-amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, protease, ribonuclease, transglutaminase, or xylanase. In one embodiment the composition comprises a S53 protease and a carbohydrate-source generating enzyme and optionally an alpha-amylase. In one particular embodiment the composition comprises an S53 protease and a glucoamylase. Preferably the enzyme activities comprised in the composition are selected from the S53 protease and one or more enzymes selected from the group consisting of glucoamylase, alpha-amylase.

In one particular embodiment the S53 protease is selected from a protease derived from a strain of the genus *Menpilus, Trametes, Dichomitus, Polyporus, Lenzites, Ganoderma, Neolentinus* or *Bacillus*, more particularly *Meripilus giganteus, Trametes versicolor, Dichomitus squalens, Polyporus arcularius, Lenzites betulinus, Ganoderma lucidum, Neolentinus lepideus,* or *Bacillus* sp. 19138.

More particularly the S53 protease is selected from the group consisting of:

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 3.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 6.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 9.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 12.

a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 15.

a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 15.

a to polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 15.

a to polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 15.

a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 15.

a polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 15.

a polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 15.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 195 to 560 or 190 to 560 of SEQ ID NO: 38.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 195 to 560 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 226 to 647 or 221 to 647 of SEQ ID NO: 39.

In one particular embodiment the composition comprises an S53 protease, and a carbohydrate source generating enzyme selected from a glucoamylase, an alpha-glucosidase, a maltogenic amylase, or a beta-amylase.

In an embodiment the glucoamylase comprised in the composition is of fungal origin, preferably from a stain of *Aspergillus*, preferably *A. niger, A. awamori*, or *A. oryzae*; or a strain of *Trichoderma*, preferably *T. reesei* or a strain of *Talaromyces*, preferably *T. emersonii* or a strain of *Trametes*, preferably *T. cingulata*, or a strain of *Pycnoporus*, preferable *P. sanguineus*, or a strain of *Gloeophyllum*, such as *G. serpiarium* or *G. trabeum*, or a strain of the Nigrofomes.

In an embodiment the glucoamylase is derived from *Trametes*, such as a strain of *Trametes cingulata*, such as the one shown in SEQ ID NO: 17 herein, In an embodiment the glucoamylase is selected from the group consisting of
(i) a glucoamylase comprising the polypeptide of SEQ ID NO: 17 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 17 herein.

In an embodiment the glucoamylase is derived from *Talaromyces*, such as a strain of *Talaromyces emersonii*, such as the one shown in SEQ ID NO: 18 herein, In an embodiment the glucoamylase is selected from the group consisting of:
(i) a glucoamylase comprising the polypeptide of SEQ ID NO: 18 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576.

In an embodiment the glucoamylase is selected from the group consisting of
(i) a glucoamylase comprising the polypeptide of SEQ ID NO: 19 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 19 herein.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 20 herein.

In an embodiment the glucoamylase is derived from *Gloeophyllum serpiarium*, such as the one shown in SEQ ID NO: 20 herein. In an embodiment the glucoamylase is selected from the group consisting of:
(i) a glucoamylase comprising the polypeptide of SEQ ID NO: 20 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20 herein.

In another embodiment the glucoamylase is derived from *Gloeophyllum trabeum* such as the one shown in SEQ ID NO: 21 herein. In an embodiment the glucoamylase is selected from the group consisting of:
(i) a glucoamylase comprising the polypeptide of SEQ ID NO: 21 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 21 herein.

In an embodiment the glucoamylase is derived from strain of the genus *Nigrofomes*, in particular a strain of *Nigrofomes* sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont); AMIGASE™ and AMIGASE™ PLUS (from DSM); G-ZYME™ G900, G-ZYME™ and G990 ZR (from DuPont).

In addition to a glucoamylase the composition may further comprise an alpha-amylase. Particularly the alpha-amylase is an acid fungal alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

Preferably the acid fungal alpha-amylase is derived from the genus *Aspergillus*, especially a strain of *A. terreus, A. niger, A. oryzae, A. awamori,* or *Aspergillus kawachii,* or from the genus *Rhizomucor*, preferably a strain the *Rhizomucor pusillus*, or the genus *Meripilus*, preferably a strain of *Meripilus giganteus*.

In a preferred embodiment the alpha-amylase is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 16 herein, or a variant thereof.

In an embodiment the alpha-amylase is selected from the group consisting of
(i) an alpha-amylase comprising the polypeptide of SEQ ID NO: 16 herein;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16 herein.

In a preferred embodiment the alpha-amylase is a variant of the alpha-amylase shown in SEQ ID NO: 16 having at least one of the following substitutions or combinations of substitutions: D165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N: Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 16 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 16 herein, preferably having one or more of the following substitutions: G128D, D143N, preferably G128D+D143N (using SEQ ID NO: 16 for numbering), and wherein the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 16 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

The compositions may be prepared in accordance with methods known in the art and may be in the form of a liquid or a dry composition. For instance, the composition may be in the form of granulate or microgranulate. The variant may be stabilized in accordance with methods known in the art.

The compositions may be prepared in accordance with methods known in the art and may be in the form of a liquid or a dry composition. The compositions may be stabilized in accordance with methods known in the art.

The enzyme composition of the present invention may be in any form suitable for use, such as, for example, a crude fermentation broth with or without cells removed, a cell lysate with or without cellular debris, a semi-purified or purified enzyme composition, or a host cell, as a source of the enzymes.

The enzyme composition may be a dry powder or granulate, a non-dusting granulate, a liquid, a stabilized liquid, or a stabilized protected enzyme. Liquid enzyme compositions may, for instance, be stabilized by adding stabilizers such as a sugar, a sugar alcohol or another polyol, and/or lactic acid or another organic acid according to established processes.

Starch Processing

Native starch consists of microscopic granules, which are insoluble in water at room temperature. When aqueous starch slurry is heated, the granules swell and eventually burst, dispersing the starch molecules into the solution. At temperatures up to about 50° C. to 75° C. the swelling may be reversible. However, with higher temperatures an irreversible swelling called "gelatinization" begins. During this "gelatinization" process there is a dramatic increase in viscosity. Granular starch to be processed may be a highly refined starch quality, preferably at least 90%, at least 95%, at least 97% or at least 99.5% pure or it may be a more crude starch-containing materials comprising (e.g., milled) whole grains including non-starch fractions such as germ residues and fibers. The raw material, such as whole grains, may be reduced in particle size, e.g., by milling, in order to open up the structure and allowing for further processing. In dry milling whole kernels are milled and used. Wet milling gives a good separation of germ and meal (starch granules and protein) and is often applied at locations where the starch hydrolysate is used in the production of, e.g., syrups. Both dry and wet milling is well known in the art of starch processing and may be used in a process of the invention. Methods for reducing the particle size of the starch containing material are well known to those skilled in the art.

As the solids level is 30-40% in a typical industrial process, the starch has to be thinned or "liquefied" so that it can be suitably processed. This reduction in viscosity is primarily attained by enzymatic degradation in current commercial practice.

Liquefaction is carried out in the presence of an alpha-amylase, preferably a bacterial alpha-amylase and/or acid fungal alpha-amylase. In an embodiment, a phytase is also present during liquefaction. In an embodiment, viscosity reducing enzymes such as a xylanase and/or beta-glucanase is also present during liquefaction.

During liquefaction, the long-chained starch is degraded into branched and linear shorter units (maltodextrins) by an alpha-amylase. Liquefaction may be carried out as a three-step hot slurry process. The slurry is heated to between 60-95° C. (e.g., 70-90° C., such as 77-86° C., 80-85° C., 83-85° C.) and an alpha-amylase is added to initiate liquefaction (thinning).

The slurry may in an embodiment be jet-cooked at between 95-140° C., e.g., 105-125° C., for about 1-15 minutes, e.g., about 3-10 minutes, especially around 5 minutes. The slurry is then cooled to 60-95° C. and more alpha-amylase is added to obtain final hydrolysis (secondary liquefaction). The jet-cooking process is carried out at pH 4.5-6.5, typically at a pH between 5 and 6. The alpha-amylase may be added as a single dose, e.g., before jet cooking.

The liquefaction process is carried out at between 70-95° C., such as 80-90° C., such as around 85° C., for about 10 minutes to 5 hours, typically for 1-2 hours. The pH is between 4 and 7, such as between 4.5 and 5.5. In order to ensure optimal enzyme stability under these conditions, calcium may optionally be added (to provide 1-60 ppm free calcium ions, such as about 40 ppm free calcium ions). After such treatment, the liquefied starch will typically have a "dextrose equivalent" (DE) of 10-15.

Generally liquefaction and liquefaction conditions are well known in the art.

Alpha-amylases for use in liquefaction are preferably bacterial acid stable alpha-amylases. Particularly the alpha-amylase is from an *Exiguobacterium* sp. or a *Bacillus* sp. such as e.g., *Bacillus stearothermophilus* or *Bacillus licheniformis*.

In an embodiment the alpha-amylase is from the genus *Bacillus*, such as a strain of *Bacillus stearothermophilus*, in particular a variant of a *Bacillus stearothermophilus* alpha-amylase, such as the one shown in SEQ ID NO: 3 in WO 99/019467 or SEQ ID NO: 22 herein.

In an embodiment the *Bacillus stearothermophilus* alpha-amylase has a double deletion of two amino acids in the region from position 179 to 182, more particularly a double deletion at positions I181+G182, R179+G180, G180+I181, R179+I181, or G180+G182, preferably I181+G182, and optionally a N193F substitution, (using SEQ ID NO: 22 for numbering).

In an embodiment the *Bacillus stearothermophilus* alpha-amylase has a substitution at position S242, preferably S242Q substitution.

In an embodiment the *Bacillus stearothermophilus* alpha-amylase has a substitution at position E188, preferably E188P substitution.

In an embodiment the alpha-amylase is selected from the group of *Bacillus stearothermophilus* alpha-amylase variants with the following mutations:
I181*+G182*+N193F+E129V+K177L+R179E;
I181+G182*+N193F+V59A+Q89R+E129V+K177L+R179E+H208Y+K220P+N224L+Q254S;
I181*+G182*+N193F+V59A Q89R+E129V+K177L+R179E+Q254S+M284V; and
I181*+G182*+N193F+E129V+K177L+R179E+K220P+N224L+S242Q+Q254S (using SEQ ID NO: 22 for numbering).

In an embodiment the alpha-amylase variant has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 22.

It should be understood that when referring to *Bacillus stearothermophilus* alpha-amylase and variants thereof they are normally produced in truncated form. In particular, the truncation may be so that the *Bacillus stearothermophilus* alpha-amylase shown in SEQ ID NO: 3 in WO 99/19467 or SEQ ID NO: 22 herein, or variants thereof, are truncated in the C-terminal preferably to have around 490 amino acids, such as from 482-493 amino acids. Preferably the *Bacillus stearothermophilus* variant alpha-amylase is truncated, preferably after position 484 of SEQ ID NO: 22, particularly after position 485, particularly after position 486, particularly after position 487, particularly after position 488, particularly after position 489, particularly after position 490, particularly after position 491, particularly after position 492, more particularly after position 493.

Saccharification may be carried out using conditions well-known in the art with a carbohydrate-source generating enzyme, in particular a glucoamylase, or a beta-amylase and optionally a debranching enzyme, such as an isoamylase or a pullulanase. For instance, a full saccharification step may last from about 24 to about 72 hours. However, it is common to do a pre-saccharification of typically 40-90 minutes at a temperature between 30-65° C., typically about 60° C., followed by complete saccharification during fermentation in a simultaneous saccharification and fermentation (SSF) process. Saccharification is typically carried out at a temperature in the range of 20-75° C., e.g., 25-65° C. and 40-70° C., typically around 60° C., and at a pH between about 4 and 5, normally at about pH 4.5.

The saccharification and fermentation steps may be carried out either sequentially or simultaneously. In an embodiment, saccharification and fermentation are performed simultaneously (referred to as "SSF"). However, it is common to perform a pre-saccharification step for about 30 minutes to 2 hours (e.g., 30 to 90 minutes) at a temperature of 30 to 65° C., typically around 60° C. which is followed by a complete saccharification during fermentation referred to as simultaneous saccharification and fermentation (SSF). The pH is usually between 4.2-4.8, e.g., pH 4.5. In a simultaneous saccharification and fermentation (SSF) process, there is no holding stage for saccharification, rather, the yeast and enzymes are added together.

In a typical saccharification process, maltodextrins produced during liquefaction are converted into dextrose by adding a glucoamylase and a debranching enzyme, such as an isoamylase (U.S. Pat. No. 4,335,208) or a pullulanase. The temperature is lowered to 60° C., prior to the addition of the glucoamylase and debranching enzyme. The saccharification process proceeds for 24-72 hours. Prior to addition of the saccharifying enzymes, the pH is reduced to below 4.5, while maintaining a high temperature (above 95° C.), to inactivate the liquefying alpha-amylase. This process reduces the formation of short oligosaccharide called "panose precursors," which cannot be hydrolyzed properly by the debranching enzyme. Normally, about 0.2-0.5% of the saccharification product is the branched trisaccharide panose (Glc pal-6Glc pal-4Glc), which cannot be degraded by a pullulanase. If active amylase from the liquefaction remains present during saccharification (i.e., no denaturing), the amount of panose can be as high as 1-2%, which is highly undesirable since it lowers the saccharification yield significantly.

Other fermentation products may be fermented at conditions and temperatures well known to persons skilled in the art, suitable for the fermenting organism in question.

The fermentation product may be recovered by methods well known in the art, e.g., by distillation. Examples of carbohydrate-source generating enzymes are disclosed in the "Enzymes" section below.

In a particular embodiment, the process of the invention further comprises, prior to the conversion of a starch-containing material to sugars/dextrins the steps of:

(x) reducing the particle size of the starch-containing material; and (y) forming a slurry comprising the starch-containing material and water.

In an embodiment, the starch-containing material is milled to reduce the particle size. In an embodiment the particle size is reduced to between 0.05-3.0 mm, preferably 0.1-0.5 mm, or so that at least 30%, preferably at least 50%, more preferably at least 70%, even more preferably at least 90% of the starch-containing material fits through a sieve with a 0.05-3.0 mm screen, preferably 0.1-0.5 mm screen.

The aqueous slurry may contain from 10-55 wt. % dry solids (DS), preferably 25-45 wt. % dry solids (DS), more preferably 30-40 wt. % dry solids (DS) of starch-containing material.

Conventional starch-conversion processes, such as liquefaction and saccharification processes are described, e.g., in U.S. Pat. No. 3,912,590, EP 252730 and EP 063909, which are incorporated herein by reference.

In an embodiment, the conversion process degrading starch to lower molecular weight carbohydrate components such as sugars or fat replacers includes a debranching step.

In the case of converting starch into a sugar, the starch is depolymerized. Such a depolymerization process consists of, e.g., a pre-treatment step and two or three consecutive process steps, i.e., a liquefaction process, a saccharification process, and depending on the desired end-product, an optional isomerization process.

When the desired final sugar product is, e.g., high fructose syrup the dextrose syrup may be converted into fructose. After the saccharification process, the pH is increased to a value in the range of 6-8, e.g., pH 7.5, and the calcium is removed by ion exchange. The dextrose syrup is then converted into high fructose syrup using, e.g., an immobilized glucose isomerase.

Production of Fermentation Products

Fermentable sugars (e.g., dextrins, monosaccharides, particularly glucose) are produced from enzymatic saccharification. These fermentable sugars may be further purified and/or converted to useful sugar products. In addition, the sugars may be used as a fermentation feedstock in a microbial fermentation process for producing end-products, such as alcohol (e.g., ethanol, and butanol), organic acids (e.g., succinic acid, 3-HP and lactic acid), sugar alcohols (e.g., glycerol), ascorbic acid intermediates (e.g., gluconate, 2-keto-D-gluconate, 2,5-diketo-D-gluconate, and 2-keto-L-gulonic acid), amino acids (e.g., lysine), proteins (e.g., antibodies and fragment thereof).

In an embodiment, the fermentable sugars obtained during the liquefaction process steps are used to produce alcohol and particularly ethanol. In ethanol production, an SSF process is commonly used wherein the saccharifying enzymes and fermenting organisms (e.g., yeast) are added together and then carried out at a temperature of 30-40° C.

The organism used in fermentation will depend on the desired end-product. Typically, if ethanol is the desired end product yeast will be used as the fermenting organism. In some preferred embodiments, the ethanol-producing microorganism is a yeast and specifically *Saccharomyces* such as strains of *S. cerevisiae* (U.S. Pat. No. 4,316,956). A variety of *S. cerevisiae* are commercially available and these include but are not limited to FALI (Fleischmann's Yeast), SUPERSTART (Alltech), FERMIOL (DSM Specialties), RED STAR (Lesaffre) and Angel alcohol yeast (Angel Yeast Company, China). The amount of starter yeast employed in the methods is an amount effective to produce a commercially significant amount of ethanol in a suitable amount of time, (e.g., to produce at least 10% ethanol from a substrate having between 25-40% DS in less than 72 hours). Yeast cells are generally supplied in amounts of about $10^4$ to about $10^{12}$, and preferably from about $10^7$ to about $10^{10}$ viable yeast count per mL of fermentation broth. After yeast is added to the mash, it is typically subjected to fermentation for about 24-96 hours, e.g., 35-60 hours. The temperature is between about 26-34° C., typically at about 32° C., and the pH is from pH 3-6, e.g., around pH 4-5.

The fermentation may include, in addition to a fermenting microorganisms (e.g., yeast), nutrients, and additional enzymes, including phytases. The use of yeast in fermentation is well known in the art.

In further embodiments, use of appropriate fermenting microorganisms, as is known in the art, can result in fermentation end product including, e.g., glycerol, 1,3-propanediol, gluconate, 2-keto-D-gluconate, 2,5-diketo-D-gluconate, 2-keto-L-gulonic acid, succinic acid, lactic acid, amino acids, and derivatives thereof. More specifically when lactic acid is the desired end product, a *Lactobacillus* sp. (*L. casei*) may be used; when glycerol or 1,3-propanediol are the desired end-products *E. coli* may be used; and when 2-keto-D-gluconate, 2,5-diketo-D-gluconate, and 2-keto-L-gulonic acid are the desired end products, *Pantoea citrea* may be used as the fermenting microorganism. The above enumerated list are only examples and one skilled in the art will be aware of a number of fermenting microorganisms that may be used to obtain a desired end product.

Processes for Producing Fermentation Products from Un-Gelatinized Starch-Containing Material The invention relates to processes for producing fermentation products from starch-containing material without gelatinization (i.e., without cooking) of the starch-containing material (often referred to as a "raw starch hydrolysis" process). The fermentation product, such as ethanol, can be produced without liquefying the aqueous slurry containing the starch-containing material and water. In one embodiment a process of the invention includes saccharifying (e.g., milled) starch-containing material, e.g., granular starch, below the initial gelatinization temperature, preferably in the presence of alpha-amylase and/or carbohydrate-source generating enzyme(s) to produce sugars that can be fermented into the fermentation product by a suitable fermenting organism. In this embodiment the desired fermentation product, e.g., ethanol, is produced from un-gelatinized (i.e., uncooked), preferably milled, cereal grains, such as corn.

Accordingly, in one aspect the invention relates to processes for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a serine protease belonging to the S53 family. Saccharification and fermentation may also be separate. Thus in another aspect the invention relates to processes of producing fermentation products, comprising the following steps:

(i) saccharifying a starch-containing material at a temperature below the initial gelatinization temperature using a carbohydrate-source generating enzyme, e.g., a glucoamylase; and (ii) fermenting using a fermentation organism;

wherein step (i) is carried out using at least a glucoamylase, and a serine protease belonging to the S53 family.

Particularly the S53 family protease is an endo-protease.

In one particular embodiment the S53 protease is selected from a protease derived from a strain of the genus *Menripilus, Trametes, Dichomitus, Polyporus, Lenzites, Ganoderma, Neolentinus* or *Bacillus*, more particularly *Meripilus giganteus, Trametes versicolor, Dichomitus squalens, Polyporus arcularius, Lenzites betulinus, Ganoderma lucidum, Neolentinus lepideus,* or *Bacillus* sp. 19138.

More particularly the S53 protease is selected from the group consisting of:

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 3.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 6.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 9.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 12.

a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 15.

a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 15.

a to polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 15.

a to polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 15.

a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 15.

a polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 15.

a polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 15.

a polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 27.

a polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 27.

a to polypeptides having a sequence identity to the polypeptide of SEQ ID NO: 27 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 27.

a to polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 27.

a polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 27.

a polypeptides having a sequence identity to the polypeptide of SEQ ID NO: 27 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 27.

a polypeptides having a sequence identity to the polypeptide of SEQ ID NO: 27 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 27.

a polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 31.

a polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 31.

a to polypeptides having a sequence identity to the polypeptide of SEQ ID NO: 31 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 31.

a to polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 31.

a polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 31.

a polypeptides having a sequence identity to the polypeptide of SEQ ID NO: 31 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 31.

a polypeptides having a sequence identity to the polypeptide of SEQ ID NO: 31 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 31.

a polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 35.

a polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 35.

a to polypeptides having a sequence identity to the polypeptide of SEQ ID NO: 35 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 35.

a to polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 35.

a polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 35.

a polypeptides having a sequence identity to the polypeptide of SEQ ID NO: 35 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 35.

a polypeptides having a sequence identity to the polypeptide of SEQ ID NO: 35 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 35.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 195 to 560 or 190 to 560 of SEQ ID NO: 38.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 195 to 560 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 226 to 647 or 221 to 647 of SEQ ID NO: 39.

In one embodiment, an alpha amylase is also added in step (i). Steps (i) and (ii) may be performed simultaneously.

The fermentation product, e.g., ethanol, may optionally be recovered after fermentation, e.g., by distillation. Typically amylase(s), such as glucoamylase(s) and/or other carbohydrate-source generating enzymes, and/or alpha-amylase(s), is(are) present during fermentation. Examples of glucoamylases and other carbohydrate-source generating enzymes include raw starch hydrolyzing glucoamylases. Examples of alpha-amylase(s) include acid alpha-amylases such as acid fungal alpha-amylases. Examples of fermenting organisms include yeast, e.g., a strain of *Saccharomyces cerevisiae*. The term "initial gelatinization temperature" means the lowest temperature at which starch gelatinization commences. In general, starch heated in water begins to gelatinize between about 50° C. and 75° C.; the exact temperature of gelatinization depends on the specific starch and can readily be determined by the skilled artisan. Thus, the initial gelatinization temperature may vary according to the plant species, to the particular variety of the plant species as well as with the growth conditions. In the context of this invention the initial gelatinization temperature of a given starch-containing material may be determined as the temperature at which birefringence is lost in 5% of the starch granules using the method described by Gorinstein and Lii, 1992, *Starch/Stärke* 44(12): 461-466. Before initiating the process a slurry of starch-containing material, such as granular starch, having 10-55 w/w % dry solids (DS), preferably 25-45 w/w % dry solids, more preferably 30-40 w/w % dry solids of starch-containing material may be prepared. The slurry may include water and/or process waters, such as stillage (backset), scrubber water, evaporator condensate or distillate, side-stripper water from distillation, or process water from other fermentation product plants. Because the process of the invention is carried out below the initial gelatinization temperature, and thus no significant viscosity increase takes place, high levels of stillage may be used if desired. In an embodiment the aqueous slurry contains from about 1 to about 70 vol. %, preferably 15-60 vol. %, especially from about 30 to 50 vol. % water and/or process waters, such as stillage (backset), scrubber water, evaporator condensate or distillate, side-stripper water from distillation, or process water from other fermentation product plants, or combinations thereof, or the like. The starch-containing material may be prepared by reducing the particle size, preferably by dry or wet milling, to 0.05 to 3.0 mm, preferably 0.1-0.5 mm. After being subjected to a process of the invention at least 85%, at least 86%, at least 87%, at least 88%, at least 89%, at least 90%, at least 91%, at least 92%, at least 93%, at least 94%, at least 95%, at least 96%, at least 97%, at least 98%, or preferably at least 99% of the dry solids in the starch-containing material are converted into a soluble starch hydrolyzate. A process in this aspect of the invention is conducted at a temperature below the initial gelatinization temperature, which means that the temperature typically lies in the range between 30-75° C., preferably between 45-60° C. In a preferred embodiment the process carried at a temperature from 25° C. to 40° C., such as from 28° C. to 35° C., such as from 30° C. to 34° C., preferably around 32° C. In an embodiment the process is carried out so that the sugar level, such as glucose level, is kept at a low level, such as below 6 w/w %, such as below about 3 w/w %, such as below about 2 w/w %, such as below about 1 w/w %, such as below about 0.5 w/w %, or below 0.25 w/w %, such as below about 0.1 w/w %. Such low levels of sugar can be accomplished by simply employing adjusted quantities of enzyme and fermenting organism. A skilled person in the art can easily determine which doses/quantities of enzyme and fermenting organism to use. The employed quantities of enzyme and fermenting organism may also be selected to maintain low concentrations of maltose in the fermentation broth. For instance, the maltose level may be kept below about 0.5 w/w %, such as below about 0.2 w/w %. The process of the invention may be carried out at a pH from about 3 and 7, preferably from pH 3.5 to 6, or more preferably from pH 4 to 5. In an embodiment fermentation is ongoing for 6 to 120 hours, in particular 24 to 96 hours.

Processes for Producing Fermentation Products from Gelatinized Starch-Containing Material In this aspect, the invention relates to processes for producing fermentation products, especially ethanol, from starch-containing material, which process includes a liquefaction step and sequentially or simultaneously performed saccharification and fermentation steps. Consequently, the invention relates to a process for producing a fermentation product from starch-containing material comprising the steps of:

(a) liquefying starch-containing material in the presence of an alpha-amylase;

(b) saccharifying the liquefied material obtained in step (a) using a carbohydrate-source generating enzyme;

(c) fermenting using a fermenting organism;

wherein a serine protease belonging to family 53 is present during step b) or c).

Particularly the S53 family protease is an endo-protease.

In one particular embodiment the S53 protease is selected from a protease derived from a strain of the genus *Meripilus, Trametes, Dichomitus, Polyporus, Lenzites, Ganoderma, Neolentinus* or *Bacillus*, more particularly *Meripilus giganteus, Trametes versicolor, Dichomitus squalens, Polyporus arcularius, Lenzites betulinus, Ganoderma lucidum, Neolentinus lepideus*, or *Bacillus* sp. 19138.

More particularly the S53 protease is selected from the group consisting of:

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 3.

a polypeptides having a sequence identity to the mature polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 3.

a polypeptides having a sequence identity to the polypeptide of SEQ ID NO: 3 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 3.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 6.

a polypeptides having a sequence identity to the mature polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 6.

a polypeptides having a sequence identity to the polypeptide of SEQ ID NO: 6 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 6.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 9.

a polypeptides having a sequence identity to the mature polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 9.

a polypeptides having a sequence identity to the polypeptide of SEQ ID NO: 9 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 9.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 12.

a polypeptides having a sequence identity to the mature polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 12.

a polypeptides having a sequence identity to the polypeptide of SEQ ID NO: 12 of at least 85%, at least 90%, at least 91%, at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 12.

a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 15.
a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 15.
a to polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 15.
a to polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 15.
a polypeptides having a sequence identity to the mature polypeptide of SEQ ID NO: 15 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 15.
a polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 15.
a polypeptides having a sequence identity to the polypeptide of SEQ ID NO: 15 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 15.
a polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 27.
a polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 27.
a to polypeptides having a sequence identity to the polypeptide of SEQ ID NO: 27 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 27.
a to polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 27.
a polypeptides having a sequence identity to the mature polypeptide of SEQ ID NO: 27 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 27.
a polypeptides having a sequence identity to the polypeptide of SEQ ID NO: 27 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 27.
a polypeptides having a sequence identity to the polypeptide of SEQ ID NO: 27 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 27.
a polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 31.
a polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 31.
a to polypeptides having a sequence identity to the polypeptide of SEQ ID NO: 31 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 31.
a to polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 31.
a polypeptides having a sequence identity to the mature polypeptide of SEQ ID NO: 31 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 31.
a polypeptides having a sequence identity to the polypeptide of SEQ ID NO: 31 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 31.
a polypeptides having a sequence identity to the polypeptide of SEQ ID NO: 31 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 31.
a polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 70% of the protease activity of the polypeptide of SEQ ID NO: 35.
a polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 75% of the protease activity of the polypeptide of SEQ ID NO: 35.

a to polypeptides having a sequence identity to the polypeptide of SEQ ID NO: 35 of at least 92%, at least 93%, at least 94%, at least 95%, at least 96%, at least 97%, at least 98%, at least 99%, or 100%, and wherein the polypeptide has at least at least 80% of the protease activity of the mature polypeptide of SEQ ID NO: 35.

a to polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 85% of the protease activity of the polypeptide of SEQ ID NO: 35.

a polypeptides having a sequence identity to the mature polypeptide of SEQ ID NO: 35 of at least 92%, at least 93%, at least 94%, at least 95%, at least 96%, at least 97%, at least 98%, at least 99%, or 100%, and wherein the polypeptide has at least at least 90% of the protease activity of the polypeptide of SEQ ID NO: 35.

a polypeptides having a sequence identity to the polypeptide of SEQ ID NO: 35 of at least 92%, at least 93%, at least 94%, at least 95%, at least 96%, at least 97%, at least 98%, at least 99%, or 100%, and wherein the polypeptide has at least at least 95% of the protease activity of the polypeptide of SEQ ID NO: 35.

a polypeptides having a sequence identity to the polypeptide of SEQ ID NO: 35 of at least 92%, at least 93%, at least 94%, at least 95%, at least 96%, at least 97%, at least 98%, at least 99%, or 100%, and wherein the polypeptide has at least at least 100% of the protease activity of the polypeptide of SEQ ID NO: 35.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 195 to 560 or 190 to 560 of SEQ ID NO: 38.

a polypeptides having a sequence identity to the polypeptide of amino acids 195 to 560 or 190 to 560 of SEQ ID NO: 38 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 195 to 560 or 190 to 560 of SEQ ID NO: 38.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 70% of the protease activity of the polypeptide of amino acids 195 to 560 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 75% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 80% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 85% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 90% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 95% of the protease activity of the polypeptide of amino acids 226 to 647 or 221 to 647 of SEQ ID NO: 39.

a polypeptides having a sequence identity to the polypeptide of amino acids 226 to 647 or 221 to 647 of SEQ ID NO: 39 of at least 92%, at least 93%, at least 94%, at least 95%, at least 96%, at least 97%, at least 98%, at least 99%, or 100%, and wherein the polypeptide has at least at least 100% of the protease activity of the polypeptide of amino acids 226 to 647 or 221 to 647 of SEQ ID NO: 39.

The fermentation product, such as especially ethanol, may optionally be recovered after fermentation, e.g., by distillation. The fermenting organism is preferably yeast, preferably a strain of *Saccharomyces cerevisiae*. In a particular embodiment, the process of the invention further comprises, prior to step (a), the steps of:

x) reducing the particle size of the starch-containing material, preferably by milling (e.g., using a hammer mill);

y) forming a slurry comprising the starch-containing material and water.

In an embodiment, the particle size is smaller than a #7 screen, e.g., a #6 screen. A #7 screen is usually used in conventional prior art processes. The aqueous slurry may contain from 10-55, e.g., 25-45 and 30-40, w/w % dry solids (DS) of starch-containing material. The slurry is heated to above the gelatinization temperature and an alpha-amylase variant may be added to initiate liquefaction (thinning). The slurry may in an embodiment be jet-cooked to further gelatinize the slurry before being subjected to alpha-amylase in step (a). Liquefaction may in an embodiment be carried out as a three-step hot slurry process. The slurry is heated to between 60-95° C., preferably between 70-90° C., such as preferably between 80-85° C. at pH 4-6, preferably 4.5-5.5, and alpha-amylase variant, optionally together with a pullulanase and/or protease, preferably metalloprotease, are added to initiate liquefaction (thinning). In an embodiment the slurry may then be jet-cooked at a temperature between 95-140° C., preferably 100-135° C., such as 105-125° C., for about 1-15 minutes, preferably for about 3-10 minutes, especially around about 5 minutes. The slurry is cooled to 60-95° C. and more alpha-amylase variant and optionally pullulanase variant and/or protease, preferably metalloprotease, is(are) added to finalize hydrolysis (secondary liquefaction). The liquefaction process is usually carried out at pH 4.0-6, in particular at a pH from 4.5 to 5.5. Saccharification step (b) may be carried out using conditions well known in the art. For instance, a full saccharification process may last up to from about 24 to about 72 hours, however, it is common only to do a pre-saccharification of typically 40-90 minutes at a temperature between 30-65° C., typically about 60° C., followed by complete saccharification during fermentation in a simultaneous saccharification and fermentation process (SSF process). Saccharification is typically carried out at temperatures from 20-75° C., preferably from 40-70° C., typically around 60° C., and at a pH between 4 and 5, normally at about pH 4.5. The most widely used process to produce a fermentation product, especially ethanol, is a simultaneous saccharification and fermentation (SSF) process, in which there is no holding stage for the saccharification, meaning that a fermenting organism, such as yeast, and enzyme(s), may be added together. SSF may typically be carried out at a temperature from 25° C. to 40° C., such as from 28° C. to 35° C., such as from 30° C. to 34° C., preferably around about 32° C. In an embodiment fermentation is ongoing for 6 to 120 hours, in particular 24 to 96 hours.

Glucoamylase Present and/or Added in Saccharification and/or Fermentation

The carbohydrate-source generating enzyme present during saccharification may in one embodiment be a glucoamylase. A glucoamylase is present and/or added in saccharification and/or fermentation, preferably simultaneous saccharification and fermentation (SSF), in a process of the invention (i.e., saccharification and fermentation of ungelatinized or gelatinized starch material).

In an embodiment the glucoamylase present and/or added in saccharification and/or fermentation is of fungal origin, preferably from a stain of *Aspergillus*, preferably *A. niger, A. awamori*, or *A. oryzae*; or a strain of *Trichoderma*, preferably *T. reesei*; or a strain of Talaromyces, preferably *T. emersonii* or a strain of *Trametes*, preferably *T. cingulata*, or a strain of *Pycnoporus*, preferably *P. sanguineus*, or a strain of *Gloeophyllum*, such as *G. serpiarium* or *G. trabeum,* or a strain of the *Nigrofomes*.

In an embodiment the glucoamylase is derived from *Talaromyces*, such as a strain of *Talaromyces emersonii*, such as the one shown in SEQ ID NO: 18 herein;

In an embodiment the glucoamylase is selected from the group consisting of (i) a glucoamylase comprising the polypeptide of SEQ ID NO: 18 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18 herein.

In an embodiment the glucoamylase is derived from a strain of the genus *Pycnoporus*, in particular a strain of *Pycnoporus sanguineus* described in WO 2011/066576 (SEQ ID NOs 2, 4 or 6), such as the one shown as SEQ ID NO: 4 in WO 2011/066576.

In an embodiment the glucoamylase is derived from a strain of the genus *Gloeophyllum*, such as a strain of *Gloeophyllum sepiarium* or *Gloeophyllum trabeum*, in particular a strain of *Gloeophyllum* as described in WO 2011/068803 (SEQ ID NO: 2, 4, 6, 8, 10, 12, 14 or 16). In a preferred embodiment the glucoamylase is the *Gloeophyllum sepiarium* shown in SEQ ID NO: 2 in WO 2011/068803 or SEQ ID NO: 20 herein.

In an embodiment the glucoamylase is derived from *Gloeophyllum serpiarium*, such as the one shown in SEQ ID NO: 20 herein. In an embodiment the glucoamylase is selected from the group consisting of:

(i) a glucoamylase comprising the polypeptide of SEQ ID NO: 20 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20 herein.

In another embodiment the glucoamylase is derived from *Gloeophyllum trabeum* such as the one shown in SEQ ID NO: 21 herein. In an embodiment the glucoamylase is selected from the group consisting of:

(i) a glucoamylase comprising the polypeptide of SEQ ID NO: 21 herein;

(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 21 herein.

In an embodiment the glucoamylase is derived from a strain of the genus *Nigrofomes*, in particular a strain of *Nigrofomes* sp. disclosed in WO 2012/064351.

Glucoamylases may in an embodiment be added to the saccharification and/or fermentation in an amount of 0.0001-20 AGU/g DS, preferably 0.001-10 AGU/g DS, especially between 0.01-5 AGU/g DS, such as 0.1-2 AGU/g DS.

Commercially available compositions comprising glucoamylase include AMG 200L; AMG 300 L; SAN™ SUPER, SAN™ EXTRA L, SPIRIZYME™ PLUS, SPIRIZYME™ FUEL, SPIRIZYME™ B4U, SPIRIZYME™ ULTRA, SPIRIZYME™ EXCEL and AMG™ E (from Novozymes A/S); OPTIDEX™ 300, GC480, GC417 (from DuPont); AMIGASE™ and AMIGASE™ PLUS (from DSM); G-ZYME™ G900, G-ZYME™ and G990 ZR (from DuPont).

According to a preferred embodiment of the invention the glucoamylase is present and/or added in saccharification and/or fermentation in combination with an alpha-amylase. Examples of suitable alpha-amylase are described below.

Alpha-Amylase Present and/or Added in Saccharification and/or Fermentation

In an embodiment an alpha-amylase is present and/or added in saccharification and/or fermentation in the processes of the invention. In a preferred embodiment the alpha-amylase is of fungal or bacterial origin. In a preferred embodiment the alpha-amylase is a fungal acid stable alpha-amylase. A fungal acid stable alpha-amylase is an alpha-amylase that has activity in the pH range of 3.0 to 7.0 and preferably in the pH range from 3.5 to 6.5, including activity at a pH of about 4.0, 4.5, 5.0, 5.5, and 6.0.

In a preferred embodiment the alpha-amylase present and/or added in saccharification and/or fermentation is derived from a strain of the genus *Rhizomucor*, preferably a strain the *Rhizomucor pusillus*, such as one shown in SEQ ID NO: 3 in WO 2013/006756, such as a *Rhizomucor pusillus* alpha-amylase hybrid having an *Aspergillus niger* linker and starch-binding domain, such as the one shown in SEQ ID NO: 16 herein, or a variant thereof.

In an embodiment the alpha-amylase present and/or added in saccharification and/or fermentation is selected from the group consisting of (i) an alpha-amylase comprising the polypeptide of SEQ ID NO: 16 herein;

(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16 herein.

In a preferred embodiment the alpha-amylase is a variant of the alpha-amylase shown in SEQ ID NO: 16 having at least one of the following substitutions or combinations of substitutions: 165M; Y141W; Y141R; K136F; K192R; P224A; P224R; S123H+Y141W; G20S+Y141W; A76G+Y141W; G128D+Y141W; G128D+D143N; P219C+Y141W; N142D+D143N; Y141W+K192R; Y141W+D143N; Y141W+N383R; Y141W+P219C+A265C; Y141W+N142D+D143N; Y141W+K192R V410A; G128D+Y141W+D143N; Y141W+D143N+P219C; Y141W+D143N+K192R; G128D+D143N+K192R; Y141W+D143N+K192R+P219C; G128D+Y141W+D143N+K192R; or G128D+Y141W+D143N+K192R+P219C (using SEQ ID NO: 16 for numbering).

In an embodiment the alpha-amylase is derived from a *Rhizomucor pusillus* with an *Aspergillus niger* glucoamylase linker and starch-binding domain (SBD), preferably disclosed as SEQ ID NO: 16 herein, preferably having one or more of the following substitutions: G128D, D143N, preferably G128D+D143N (using SEQ ID NO: 16 for numbering), and wherein the alpha-amylase variant present and/or added in saccharification and/or fermentation has at least 75% identity preferably at least 80%, more preferably at least 85%, more preferably at least 90%, more preferably at least 91%, more preferably at least 92%, even more preferably at least 93%, most preferably at least 94%, and even most preferably at least 95%, such as even at least 96%, at least 97%, at least 98%, at least 99%, but less than 100% identity to the polypeptide of SEQ ID NO: 16 herein.

In a preferred embodiment the ratio between glucoamylase and alpha-amylase present and/or added during saccharification and/or fermentation may preferably be in the range from 500:1 to 1:1, such as from 250:1 to 1:1, such as from 100:1 to 1:1, such as from 100:2 to 100:50, such as from 100:3 to 100:70.

Starch-Containing Materials

Any suitable starch-containing starting material may be used in a process of the present invention. The starting material is generally selected based on the desired fermentation product. Examples of starch-containing starting materials, suitable for use in the processes of the present invention, include barley, beans, cassava, cereals, corn, milo, peas, potatoes, rice, rye, sago, sorghum, sweet potatoes, tapioca, wheat, and whole grains, or any mixture thereof. The starch-containing material may also be a waxy or non-waxy type of corn and barley. In a preferred embodiment the starch-containing material is corn. In a preferred embodiment the starch-containing material is wheat.

Fermentation Products

The term "fermentation product" means a product produced by a method or process including fermenting using a fermenting organism. Fermentation products include alcohols (e.g., ethanol, methanol, butanol); organic acids (e.g., citric acid, acetic acid, itaconic acid, lactic acid, succinic acid, gluconic acid); ketones (e.g., acetone); amino acids (e.g., glutamic acid); gases (e.g., $H_2$ and $CO_2$); antibiotics (e.g., penicillin and tetracycline); enzymes; vitamins (e.g., riboflavin, $B_{12}$, beta-carotene); and hormones. In a preferred embodiment the fermentation product is ethanol, e.g., fuel ethanol; drinking ethanol, i.e., potable neutral spirits; or industrial ethanol or products used in the consumable alcohol industry (e.g., beer and wine), dairy industry (e.g., fermented dairy products), leather industry and tobacco industry. Preferred beer types comprise ales, stouts, porters, lagers, bitters, malt liquors, happoushu, high-alcohol beer, low-alcohol beer, low-calorie beer or light beer. In an preferred embodiment the fermentation product is ethanol.

Starch Slurry Processing with Stillage

Milled starch-containing material is combined with water and recycled thin-stillage resulting in an aqueous slurry. The slurry can comprise between 15 to 55% ds w/w (e.g., 20 to 50%, 25 to 50%, 25 to 45%, 25 to 40%, 20 to 35% and 30-36% ds). In some embodiments, the recycled thin-stillage (backset) is in the range of about 10 to 70% v/v (e.g., 10 to 60%, 10 to 50%, 10 to 40%, 10 to 30%, 10 to 20%, 20 to 60%, 20 to 50%, 20 to 40% and also 20 to 30%).

Once the milled starch-containing material is combined with water and backset, the pH is not adjusted in the slurry. Further the pH is not adjusted after the addition of a phytase and optionally an alpha-amylase to the slurry. In an embodiment, the pH of the slurry will be in the range of about pH 4.5 to less than about 6.0 (e.g., pH 4.5 to 5.8, pH 4.5 to 5.6, pH 4.8 to 5.8, pH 5.0 to 5.8, pH 5.0 to 5.4, pH 5.2 to 5.5 and pH 5.2 to 5.9). The pH of the slurry may be between about pH 4.5 and 5.2 depending on the amount of thin stillage added to the slurry and the type of material comprising the thin stillage. For example, the pH of the thin stillage may be between pH 3.8 and pH 4.5.

During ethanol production, acids can be added to lower the pH in the beer well, to reduce the risk of microbial contamination prior to distillation.

In some embodiments, a phytase is added to the slurry. In other embodiments, in addition to phytase, an alpha-amylase is added to the slurry. In some embodiments, a phytase and alpha-amylase are added to the slurry sequentially. In other embodiments, a phytase and alpha-amylase are added simultaneously. In some embodiments, the slurry comprising a phytase and optionally, an alpha-amylase, are incubated (pretreated) for a period of about 5 minutes to about 8 hours (e.g., 5 minutes to 6 hours, 5 minutes to 4 hours, 5 minutes to 2 hours, and 15 minutes to 4 hours). In other embodiments, the slurry is incubated at a temperature in the range of about 40 to 115° C. (e.g., 45 to 80° C., 50 to 70° C., 50 to 75° C., 60 to 110° C., 60 to 95° C., 70 to 110° C., 70 to 85° C. and 77 to 86° C.).

In other embodiments, the slurry is incubated at a temperature of about 0 to about 30° C. (e.g., 0 to 25° C., 0 to 20° C., 0 to 15° C., 0 to 10° C. and 0 to 5° C.) below the starch gelatinization temperature of the starch-containing material. In some embodiments, the temperature is below about 68° C., below about 65° C., below about 62° C., below about 60° C. and below about 55° C. In some embodiments, the temperature is above about 45° C., above about 50° C., above about 55° C. and above about 60° C. In some embodiments, the incubation of the slurry comprising a phytase and an alpha-amylase at a temperature below the starch gelatinization temperature is referred to as a primary (1°) liquefaction.

In one embodiment, the milled starch-containing material is corn or milo. The slurry comprises 25 to 40% DS, the pH is in the range of 4.8 to 5.2, and the slurry is incubated with a phytase and optionally an alpha-amylase for 5 minutes to 2 hours, at a temperature range of 60 to 75° C.

In a further liquefaction step, the incubated or pretreated starch-containing material is exposed to an increase in temperature such as about 0 to about 45° C. above the starch gelatinization temperature of the starch-containing material (e.g., 70° C. to 120° C., 70° C. to 110° C., and 70° C. to 90° C.) for a period of time of about 2 minutes to about 6 hours (e.g., 2 minutes to 4 hours, 90 minutes, 140 minutes and 90 to 140 minutes) at a pH of about 4.0 to 5.5 more preferably between 1 hour to 2 hours. The temperature can be increased by a conventional high temperature jet cooking system for a short period of time, for example, for 1 to 15 minutes. Then the starch may be further hydrolyzed at a temperature ranging from about 75° C. to 95° C. (e.g., 80° C. to 90° C. and 80° C. to 85° C.) for a period of about 15 to 150 minutes (e.g., 30 to 120 minutes). In a preferred embodiment, the pH is not adjusted during these process steps and the pH of the liquefied mash is in the range of about pH 4.0 to pH 5.8 (e.g., pH 4.5 to 5.8, pH 4.8 to 5.4, and pH 5.0 to 5.2). In some embodiments, a second dose of thermostable alpha-amylase is added to the secondary liquefaction step, but in other embodiments there is no additional dosage of alpha-amylase.

The incubation and liquefaction steps may be followed by saccharification and fermentation steps well known in the art.

Distillation

Optionally, following fermentation, an alcohol (e.g., ethanol) may be extracted by, for example, distillation and optionally followed by one or more process steps.

In some embodiments, the yield of ethanol produced by the methods provided herein is at least 8%, at least 10%, at least 12%, at least 14%, at least 15%, at least 16%, at least 17% and at least 18% (v/v) and at least 23% v/v. The ethanol obtained according to the process provided herein may be used as, for example, fuel ethanol, drinking ethanol, i.e., potable neutral spirits, or industrial ethanol.

By-Products

Left over from the fermentation is the grain, which is typically used for animal feed either in liquid or dried form. In further embodiments, the end product may include the fermentation coproducts such as distiller's dried grains (DDG) and distillers dried grain plus solubles (DDGS), which may be used, for example, as an animal feed.

Further details on how to carry out liquefaction, saccharification, fermentation, distillation, and recovery of ethanol are well known to the skilled person.

According to the process provided herein, the saccharification and fermentation may be carried out simultaneously or separately.

Fermenting Organisms

The term "fermenting organism" refers to any organism, including bacterial and fungal organisms, such as yeast and filamentous fungi, suitable for producing a desired fermentation product. Suitable fermenting organisms are able to ferment, i.e., convert, fermentable sugars, such as arabinose, fructose, glucose, maltose, mannose, or xylose, directly or indirectly into the desired fermentation product.

Examples of fermenting organisms include fungal organisms such as yeast Preferred yeast include strains of *Saccharomyces*, in particular *Saccharomyces cerevisiae* or *Saccharomyces uvarum*, strains of *Pichia*, in particular *Pichia stipitis* such as *Pichia stipitis* CBS 5773 or *Pichia pastoris*, strains of *Candida*, in particular *Candida arabinofermentans, Candida boidinii, Candida diddensii, Candida shehatae, Candida sonorensis, Candida tropicalis*, or *Candida utilis*. Other fermenting organisms include strains of *Hansenula*, in particular *Hansenula anomala* or *Hansenula polymorpha*; strains of *Kluyveromyces*, in particular *Kluyveromyces fragilis* or *Kluyveromyces marxianus*; and strains of *Schizosaccharomyces*, in particular *Schizosaccharomyces pombe*.

Preferred bacterial fermenting organisms include strains of *Escherichia*, in particular *Escherichia coli*, strains of *Zymomonas*, in particular *Zymomonas mobilis*, strains of *Zymobacter*, in particular *Zymobactor palmae*, strains of *Klebsiella* in particular *Klebsiella oxytoca*, strains of *Leuconostoc*, in particular *Leuconostoc mesenteroides*, strains of *Clostridium*, in particular *Clostridium butyricum*, strains of *Enterobacter*, in particular *Enterobacter aerogenes*, and strains of *Thermoanaerobacter*, in particular *Thermoanaerobacter* BG1L1 (*Appl. Microbiol. Biotech.* 77: 61-86), *Thermoanarobacter ethanolicus, Thermoanaerobacter mathranii,* or *Thermoanaerobacter thermosaccharolyticum.* Strains of *Lactobacillus* are also envisioned as are strains of *Corynebacterium glutamicum* R, *Bacillus thermoglucosidaisus,* and *Geobacillus thermoglucosidasius*.

In an embodiment, the fermenting organism is a C6 sugar fermenting organism, such as a strain of, e.g., *Saccharomyces cerevisiae*.

In an embodiment, the fermenting organism is a C5 sugar fermenting organism, such as a strain of, e.g., *Saccharomyces cerevisiae*.

In one embodiment, the fermenting organism is added to the fermentation medium so that the viable fermenting organism, such as yeast, count per mL of fermentation medium is in the range from $10^5$ to $10^{12}$, preferably from $10^7$ to $10^{10}$, especially about $5 \times 10^7$.

Yeast is the preferred fermenting organism for ethanol fermentation. Preferred are strains of *Saccharomyces*, especially strains of the species *Saccharomyces cerevisiae*, preferably strains which are resistant towards high levels of ethanol, i.e., up to, e.g., about 10, 12, 15 or 20 vol. % or more ethanol.

In an embodiment, the C5 utilizing yeast is a *Saccharomyces cerevisea* strain disclosed in WO 2004/085627.

In an embodiment, the fermenting organism is a C5 eukaryotic microbial cell concerned in WO 2010/074577 (Nedalco).

In an embodiment, the fermenting organism is a transformed C5 eukaryotic cell capable of directly isomerize xylose to xylulose disclosed in US 2008/0014620.

In an embodiment, the fermenting organism is a C5 sugar fermentating cell disclosed in WO 2009/109633.

Commercially available yeast include LNF SA-1, LNF BG-1, LNF PE-2, and LNF CAT-1 (available from LNF Brazil), RED STAR™ and ETHANOL RED™ yeast (available from Fermentis/Lesaffre, USA), FALI (available from Fleischmann's Yeast, USA), SUPERSTART and THERMOSACC™ fresh yeast (available from Ethanol Technology, WI, USA), BIOFERM AFT and XR (available from NABC—North American Bioproducts Corporation, GA, USA), GERT STRAND (available from Gert Strand AB, Sweden), and FERMIOL (available from DSM Specialties).

The fermenting organism capable of producing a desired fermentation product from fermentable sugars is preferably grown under precise conditions at a particular growth rate. When the fermenting organism is introduced into/added to the fermentation medium the inoculated fermenting organism pass through a number of stages. Initially growth does not occur. This period is referred to as the "lag phase" and may be considered a period of adaptation. During the next phase referred to as the "exponential phase" the growth rate gradually increases. After a period of maximum growth the rate ceases and the fermenting organism enters "stationary phase". After a further period of time the fermenting organism enters the "death phase" where the number of viable cells declines.

Fermentation

The fermentation conditions are determined based on, e.g., the kind of plant material, the available fermentable sugars, the fermenting organism(s) and/or the desired fermentation product. One skilled in the art can easily determine suitable fermentation conditions. The fermentation may be carried out at conventionally used conditions. Preferred fermentation processes are anaerobic processes.

For example, fermentations may be carried out at temperatures as high as 75° C., e.g., between 40-70° C., such as between 50-60° C. However, bacteria with a significantly lower temperature optimum down to around room temperature (around 20° C.) are also known. Examples of suitable fermenting organisms can be found in the "Fermenting Organisms" section above.

For ethanol production using yeast, the fermentation may go on for 24 to 96 hours, in particular for 35 to 60 hours. In an embodiment the fermentation is carried out at a temperature between 20 to 40° C., preferably 26 to 34° C., in particular around 32° C. In an embodiment the pH is from pH 3 to 6, preferably around pH 4 to 5.

Other fermentation products may be fermented at temperatures known to the skilled person in the art to be suitable for the fermenting organism in question.

Fermentation is typically carried out at a pH in the range between 3 and 7, preferably from pH 3.5 to 6, such as around pH 5. Fermentations are typically ongoing for 6-96 hours.

The processes of the invention may be performed as a batch or as a continuous process. Fermentations may be conducted in an ultrafiltration system wherein the retentate is held under recirculation in the presence of solids, water, and the fermenting organism, and wherein the permeate is the desired fermentation product containing liquid. Equally contemplated are methods/processes conducted in continuous membrane reactors with ultrafiltration membranes and where the retentate is held under recirculation in presence of solids, water, and the fermenting organism(s) and where the permeate is the fermentation product containing liquid.

After fermentation the fermenting organism may be separated from the fermented slurry and recycled.

Fermentation Medium

The phrase "fermentation media" or "fermentation medium" refers to the environment in which fermentation is carried out and comprises the fermentation substrate, that is, the carbohydrate source that is metabolized by the fermenting organism(s).

The fermentation medium may comprise other nutrients and growth stimulator(s) for the fermenting organism(s). Nutrient and growth stimulators are widely used in the art of fermentation and include nitrogen sources, such as ammonia; vitamins and minerals, or combinations thereof.

Recovery

Subsequent to fermentation, the fermentation product may be separated from the fermentation medium. The fermentation medium may be distilled to extract the desired fermentation product or the desired fermentation product may be extracted from the fermentation medium by micro or membrane filtration techniques. Alternatively, the fermentation product may be recovered by stripping. Methods for recovery are well known in the art.

The present invention is further described by the following numbered embodiments:

Embodiment 1

A process for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a serine protease belonging to the S53 family.

Embodiment 2

A process for producing a fermentation product from starch-containing material comprising the steps of
(a) liquefying starch-containing material in the presence of an alpha-amylase;
(b) saccharifying the liquefied material obtained in step (a) using a carbohydrate-source generating enzyme;
(c) fermenting using a fermenting organism;
wherein a serine protease belonging to family 53 is present during step b) and/or c).

Embodiment 3

The process of embodiment 1 or 2, wherein the S53 protease is derived from a strain of the genus *Meripilus*,

*Trametes, Dichomitus, Polyporus, Lenzites, Ganoderma, Neolentinus, Lecanicillium, Talaromyces* or *Bacillus*, more particularly *Meripilus giganteus, Trametes versicolor, Dichomitus squalens, Polyporus arcularius, Lenzites betulinus, Ganoderma lucidum, Neolentinus lepideus, Lecanicillium* sp WMM742, *Talaromyces proteolyticus* or *Bacillus* sp. 19138.

Embodiment 4

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 3;
 (b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 1.

Embodiment 5

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 6;
 (b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 4.

Embodiment 6

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 9;
 (b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 7.

Embodiment 7

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 12;
 (b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 10.

Embodiment 8

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 15;
 (b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 13.

Embodiment 9

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 26;
 (c) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 25.

Embodiment 10

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 30;
 (b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 29.

Embodiment 11

The process of embodiments 1 or 2, wherein the S53 protease is a polypeptide having serine protease activity, selected from the group consisting of:
 (a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 34;
 (b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 33.

Embodiment 12

The process of embodiments 1 or 2, wherein the S53 protease is a polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 38, such as amino acids 195 to 560 of SEQ ID NO: 38.

Embodiment 13

The process of embodiments 1 or 2, wherein the S53 protease is a polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 39, such as amino acids 226 to 649 of SEQ ID NO: 39.

Embodiment 14

The process of any of embodiments 1-13, wherein an alpha-amylase is present or added during saccharification and/or fermentation.

Embodiment 15

The process of embodiment 14, wherein the alpha-amylase is an acid alpha-amylase, preferably an acid fungal alpha-amylase.

Embodiment 16

The process of embodiment 15, wherein the alpha-amylase is a derived from the genus *Aspergillus*, especially a strain of *A. terreus, A. niger, A. oryzae, A. awamori,* or Aspergillus *kawachii*, or of the genus *Rhizomucor*, preferably a strain the *Rhizomucor pusillus*, or the genus *Meripilus*, preferably a strain of *Meripilus giganteus*.

Embodiment 17

The process according to embodiment 16, wherein the alpha-amylase present in saccharification and/or fermentation is derived from a strain of the genus *Rhizomucor*, preferably a strain of *Rhizomucor pusillus*, such as a *Rhizomucor pusillus* alpha-amylase hybrid having an *Aspergillus niger* linker and starch-bonding domain, such as the one shown in SEQ ID NO: 16.

Embodiment 18

The process of embodiment 17, wherein the alpha-amylase present in saccharification and/or fermentation is selected from the group consisting of:
(i) an alpha-amylase comprising the polypeptide of SEQ ID NO: 16;
(ii) an alpha-amylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 16.

Embodiment 19

The process of embodiment 18, wherein the alpha-amylase is derived from a *Rhizomucor pusillus* with an *Aspergillus niger* glucoamylase linker and starch-binding domain (SBD), preferably disclosed as SEQ ID NO: 16, preferably having one or more of the following substitutions: G128D, D143N, preferably G128D+D143N.

Embodiment 20

The process of any of embodiments 14-19, wherein the alpha-amylase is present in an amount of 0.001 to 10 AFAU/g DS, preferably 0.01 to 5 AFAU/g DS, especially 0.3 to 2 AFAU/g DS or 0.001 to 1 FAU-F/g DS, preferably 0.01 to 1 FAU-F/g DS.

Embodiment 21

The process of any of embodiments 1-20, wherein the carbohydrate-source generating enzyme is selected from the group consisting of glucoamylase, alpha-glucosidase, maltogenic amylase, and beta-amylase.

Embodiment 22

The process of any of embodiments 1-21, wherein the carbohydrase-source generating enzyme is glucoamylase and is present in an amount of 0.001 to 10 AGU/g DS, preferably from 0.01 to 5 AGU/g DS, especially 0.1 to 0.5 AGU/g DS.

Embodiment 23

The process of any of embodiments 14-22, wherein the alpha-amylase and glucoamylase is added in a ratio of between 0.1 and 100 AGU/FAU-F, preferably 2 and 50 AGU/FAU-F, especially between 10 and 40 AGU/FAU-F when steps (a) and (b) are carried out simultaneously.

Embodiment 24

The process of embodiment 21-23, wherein the glucoamylase is derived from a strain of *Aspergillus*, preferably *Aspergillus niger* or *Aspergillus awamori*, a strain of *Talaromyces*, especially *Talaromyces emersonii*, or a strain of *Athelia*, especially *Athelia rolfsii*; a strain of *Trametes*, preferably *Trametes cingulata*; a strain of the genus *Gloeophyllum*, e.g., a strain of *Gloeophyllum sepiarium* or *Gloeophyllum trabeum*; a strain of the genus *Pycnoporus*, e.g., a strain of *Pycnoporus sanguineus*, or a mixture thereof.

Embodiment 25

The process of embodiment 24, wherein the glucoamylase is derived from *Trametes*, such as a strain of *Trametes cingulata*, such as the one shown in SEQ ID NO: 17.

Embodiment 26

The process of embodiment 25, wherein the glucoamylase is selected from the group consisting of:

(i) a glucoamylase comprising the polypeptide of SEQ ID NO: 17;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 17.

Embodiment 27

The process of embodiment 24, wherein the glucoamylase is derived from *Talaromyces*, such as a strain of *Talaromyces emersonii*, such as the one shown in SEQ ID NO: 18.

Embodiment 28

The process of embodiment 27, wherein the glucoamylase is selected from the group consisting of:
(i) a glucoamylase comprising the polypeptide of SEQ ID NO: 18;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 18.

Embodiment 29

The process of embodiment 24, wherein the glucoamylase is derived from a strain of the genus *Pycnoporus*, such as a strain of *Pycnoporus sanguineus* such as the one shown in SEQ ID NO: 19.

Embodiment 30

The process of embodiment 29, wherein the glucoamylase is selected from the group consisting of:
(i) a glucoamylase comprising the polypeptide of SEQ ID NO: 19;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 19.

Embodiment 31

The process of embodiment 24, wherein the glucoamylase is derived from a strain of the genus *Gloeophyllum*, such as a strain of *Gloeophyllum sepiarium* shown in SEQ ID NO: 20.

Embodiment 32

The process of embodiment 3, wherein the glucoamylase is selected from the group consisting of:
(i) a glucoamylase comprising the polypeptide of SEQ ID NO: 20 herein;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 20 herein.

Embodiment 33

The process of embodiment 24, wherein the glucoamylase is derived from a strain of the genus *Gloeophyllum*, such as a strain of *Gloeophyllum trabeum* such as the one shown in SEQ ID NO: 21.

Embodiment 34

The process of embodiment 33, wherein the glucoamylase is selected from the group consisting of:
(i) a glucoamylase comprising the polypeptide of SEQ ID NO: 21;
(ii) a glucoamylase comprising an amino acid sequence having at least 60%, at least 70%, e.g., at least 75%, at least 80%, at least 85%, at least 90%, at least 91%, at least 92%, at least 93%, at least 94%, at least 95%, at least 96%, at least 97%, at least 98%, or at least 99% identity to the polypeptide of SEQ ID NO: 21.

Embodiment 35

The process of any of embodiments 1-34, wherein the fermentation product is recovered after fermentation.

Embodiment 36

The process of any of embodiments 1-35, wherein the fermentation product is an alcohol, preferably ethanol, especially fuel ethanol, potable ethanol and/or industrial ethanol.

Embodiment 37

The process of any of embodiments 1-36, wherein the fermenting organism is yeast, preferably a strain of *Saccharomyces*, especially a strain of *Saccharomyces cerevisae*.

Embodiment 38

The process of any of embodiments 1, wherein the starch-containing material is granular starch.

Embodiment 39

The process of any of embodiments 1-35, wherein the starch-containing material is derived from whole grain.

Embodiment 40

The process of any of embodiments 1-37, wherein the starch-containing material is derived from corn, wheat, barley, rye, milo, sago, cassava, tapioca, sorghum, rice or potatoes.

Embodiment 41

The process of any of embodiments 1-40, wherein fermentation is carried out at a pH in the range between 3 and 7, preferably from 3.5 to 6, or more preferably from 4 to 5.

Embodiment 42

The process of any of embodiments 1-41, wherein the process is carried out for between 1 to 96 hours, preferably is from 6 to 72 hours.

Embodiment 43

The process of any of embodiments 1-42, wherein the dry solid content of the starch-containing material is in the range from 20-55 w/w-%, preferably 25-40 w/w-%, more preferably 30-35 w/w-%.

Embodiment 44

The process of any of embodiments 1-43, wherein the starch-containing material is prepared by reducing the particle size of starch-containing material to a particle size of 0.1-0.5 mm.

Embodiment 45

The process of any of embodiments 1-44, wherein the temperature during simultaneous saccharification and fermentation is between 25° C. and 40° C., such as between 28° C. and 35° C., such as between 30° C. and 34° C., such as around 32° C.

Embodiment 46

The process of any of embodiments 2-45, wherein step (a) is carried out at pH 4.0-6.5, preferably at a pH from 4.5 to 5.5 Embodiment 47. The process of embodiment 2, wherein the step (b) and (c) are carried out sequentially or simultaneously (i.e., SSF process).

Embodiment 48

The process of embodiment 2, further comprising, prior to the step (a), the steps of:
x) reducing the particle size of starch-containing material;
y) forming a slurry comprising the starch-containing material and water.

Embodiment 49

The process of any of embodiments 2-48, wherein a pullulanase is present i) during fermentation, and/or ii) before, during, and/or after liquefaction.

Embodiment 50

A composition comprising a S53 protease and a carbohydrate-source generating enzyme and optionally an alpha-amylase.

Embodiment 51

The composition of embodiment 50, wherein the S53 protease is derived from a strain of the genus *Menpilus*, *Trametes*, *Dichomitus*, *Polyporus*, *Lenzites*, *Ganoderma*, *Neolentinus*, *Lecanicillium*, *Talaromyces* or *Bacillus*, more particularly *Meripilus giganteus*, *Trametes versicolor*, *Dichomitus squalens*, *Polyporus arcularius*, *Lenzites betulinus*, *Ganoderma lucidum*, *Neolentinus lepideus*, *Lecanicillium* sp WMM742, *Talaromyces proteolyticus* or *Bacillus* sp. 19138.

Embodiment 52

The composition of any of embodiments 50-51, wherein the S53 protease is a polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 3;
(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 1.

Embodiment 53

The composition of any of embodiments 50-51, wherein the S53 protease is a polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 6;
(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 4.

Embodiment 54

The composition of any of embodiments 50-51, wherein the S53 protease is a polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 9;
(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 7.

Embodiment 55

The composition of any of embodiments 50-51, wherein the S53 protease is a polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 12;
(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 10.

Embodiment 56

The composition of any of embodiments 50-51, wherein the S53 protease is a polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 15;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 13.

Embodiment 57

The composition of any of embodiments 50-51, wherein the S53 protease is a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 26;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 25.

Embodiment 58

The composition of any of embodiments 50-51, wherein the S53 protease is a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 30;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 29.

Embodiment 59

The composition of any of embodiments 50-51, wherein the S53 protease is a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 34;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 33.

Embodiment 60

The composition of any of embodiments 50-51, wherein the S53 protease is a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 38, such as amino acids 195 to 560 or 190 to 560 of SEQ ID NO: 38.

Embodiment 61

The composition of any of embodiments 50-51, wherein the S53 protease is a polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 39, such as amino acids 226 to 647 or 221 to 647 of SEQ ID NO: 39.

Embodiment 62

The composition of any of embodiments 50-61, wherein the carbohydrate-source generating enzyme is selected from the group of glucoamylase, alpha-glucosidase, maltogenic amylase, and beta-amylase.

Embodiment 63

The composition of embodiment 62, wherein the carbohydrate-source generating enzyme is selected from the group of glucoamylases derived from a strain of *Aspergillus*, preferably *Aspergillus niger* or *Aspergillus awamori*, a strain of *Trichoderma*, especially *T. reesei*, a strain of *Talaromyces*, especially *Talaromyces emersonii*, or a strain of *Athelia*, especially *Athelia rolfsii*; a strain of *Trametes*, preferably *Trametes cingulata*; a strain of the genus *Gloeophyllum*, e.g., a strain of *Gloeophyllum sepiarum* or *Gloeophyllum trabeum*; a strain of the genus *Pycnoporus*, e.g., a strain of *Pycnoporus sanguineus*; or a mixture thereof.

Embodiment 64

The composition of any of embodiments 50-63, wherein the alpha-amylase is selected from the group of fungal alpha-amylases, preferably derived from the genus *Aspergillus*, especially a strain of *A. terreus, A. niger, A. oryzae, A. awamori*, or *Aspergillus kawachii*, or of the genus *Rhizomucor*, preferably a strain the *Rhizomucor pusillus*, or the genus *Meripilus*, preferably a strain of *Meripilus giganteus*.

Embodiment 65

A use of a serine protease, particularly a S53 protease, in a process of fermenting gelatinized and/or un-gelatinized starch-containing material into a fermentation product.

Embodiment 66

A polypeptide having serine protease activity, selected from the group consisting of:

(a) a polypeptide having at least 85%, at least 90%, at least 91%, at least 92%, at least 93%, at least 94%, 95%, at least 96%, at least 97%, at least 98%, at least 99%, or 100% sequence identity to the polypeptide of SEQ ID NO: 12;

(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 10.

Embodiment 67

A polypeptide having serine protease activity, selected from the group consisting of
(a) a polypeptide having at least 85%, at least 90%, at least 91%, at least 92%, at least 93%, at least 94%, 95%, at least 96%, at least 97%, at least 98%, at least 99%, or 100% sequence identity to the polypeptide of SEQ ID NO: 15;
(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 13.

Embodiment 68

A polypeptide having serine protease activity, selected from the group consisting of
(a) a polypeptide having at least 85%, at least 90%, at least 91%, at least 92%, at least 93%, at least 94%, 95%, at least 96%, at least 97%, at least 98%, at least 99%, or 100% sequence identity to the polypeptide of SEQ ID NO: 27;
(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 25.

Embodiment 69

A polypeptide having serine protease activity, selected from the group consisting of
(a) a polypeptide having at least 85%, at least 90%, at least 91%, at least 92%, at least 93%, at least 94%, 95%, at least 96%, at least 97%, at least 98%, at least 99%, or 100% sequence identity to the polypeptide of SEQ ID NO: 31;
(b) a polypeptide encoded by a polynucleotide having at least 85%, at least 90%, at least 91%, at least 92%, at least 93%, at least 94%, 95%, at least 96%, at least 97%, at least 98%, at least 99%, or 100% sequence identity to the mature polypeptide coding sequence of SEQ ID NO: 29.

Embodiment 70

A polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 38, such as amino acids 195 to 560 or 190 to 560 of SEQ ID NO: 38.

Embodiment 71

A polypeptide having serine protease activity, selected from the group consisting of:
(a) a polypeptide having at least 85%, at least 90%, at least 91%, at least 92%, at least 93%, at least 94%, 95%, at least 96%, at least 97%, at least 98%, at least 99%, or 100% sequence identity to the mature polypeptide of SEQ ID NO: 39, such as amino acids 226 to 647 or 221 to 647 of SEQ ID NO: 39.

Embodiment 72

The polypeptide of any of embodiments 66-71, comprising or consisting of SEQ ID NO: 12, SEQ ID NO: 15, SEQ ID NO: 27, or SEQ ID NO: 31, amino acids 195 to 560 or 190 to 560 of SEQ ID NO: 38, amino acids 226 to 647 or 221 to 647 of SEQ ID NO: 39.

Embodiment 73

The polypeptide of any of embodiments 66-72, which is a fragment of SEQ ID NO: 12, SEQ ID NO: 15, SEQ ID NO: 27, or SEQ ID NO: 31, wherein the fragment has protease activity.

Embodiment 74

A polynucleotide encoding the polypeptide of any of embodiments 66-73.

Embodiment 75

A nucleic acid construct or expression vector comprising the polynucleotide of embodiment 74 operably linked to one or more control sequences that direct the production of the polypeptide in an expression host.

Embodiment 76

A recombinant host cell comprising the polynucleotide of embodiment 74 operably linked to one or more control sequences that direct the production of the polypeptide.

Embodiment 77

The process according to any of the embodiments 1-2 or the composition according to embodiment 50, or the use according to embodiment 65, wherein the S53 protease is an endo-protease.

EXAMPLES

Enzyme Assays
Assays for Glucoamylase Activity
Glucoamylase Units, AGU

The Glucoamylase Unit (AGU) is defined as the amount of enzyme, which hydrolyses 1 micromole maltose per minute under the standard conditions (37° C., pH 4.3, substrate: maltose 100 mM, buffer acetate 0.1 M, reaction time 6 minutes as set out in the glucoamylase incubation below), thereby generating glucose.

| glucoamylase incubation: | |
|---|---|
| Substrate: | maltose 100 mM |
| Buffer: | acetate 0.1M |
| pH: | 4.30 ± 0.05 |
| Incubation temperature: | 37° C. ± 1 |
| Reaction time: | 6 minutes |
| Enzyme working range: | 0.5-4.0 AGU/mL |

The analysis principle is described by 3 reaction steps:
Step 1 is an Enzyme Reaction:
Glucoamylase (AMG), EC 3.2.1.3 (exo-alpha-1,4-glucan-glucohydrolase), hydrolyzes maltose to form alpha-D-glucose. After incubation, the reaction is stopped with NaOH.
Steps 2 and 3 Result in an Endpoint Reaction:
Glucose is phosphorylated by ATP, in a reaction catalyzed by hexokinase. The glucose-6-phosphate formed is oxidized to 6-phosphogluconate by glucose-6-phosphate dehydrogenase. In this same reaction, an equimolar amount of NAD+ is reduced to NADH with a resulting increase in absorbance at 340 nm. An autoanalyzer system such as Konelab 30 Analyzer (Thermo Fisher Scientific) may be used.

| Color reaction | |
|---|---|
| Tris | Approx. 35 mM |
| ATP | 0.7 mM |
| NAD+ | 0.7 mM |
| Mg2+ | 1.8 mM |
| Hexokinase | >850 U/L |
| Glucose-6-P-DH | >850 U/L |
| pH | approx. 7.8 |
| Temperature | 37.0° C. ± 1.0° C. |
| Reaction time | 420 sec |
| Wavelength | 340 nm |

Acid Alpha-Amylase Activity

When used according to the present invention the activity of an acid alpha-amylase may be measured in AFAU (Acid Fungal Alpha-amylase Units) or FAU-F.

Acid Alpha-Amylase Activity (AFAU)

Acid alpha-amylase activity may be measured in AFAU (Acid Fungal Alpha-amylase Units), which are determined relative to an enzyme standard. 1 AFAU is defined as the amount of enzyme which degrades 5.260 mg starch dry matter per hour under the below mentioned standard conditions.

Acid alpha-amylase, an endo-alpha-amylase (1,4-alpha-D-glucan-glucanohydrolase, E.C. 3.2.1.1) hydrolyzes alpha-1,4-glucosidic bonds in the inner regions of the starch molecule to form dextrins and oligosaccharides with different chain lengths. The intensity of color formed with iodine is directly proportional to the concentration of starch. Amylase activity is determined using reverse colorimetry as a reduction in the concentration of starch under the specified analytical conditions.

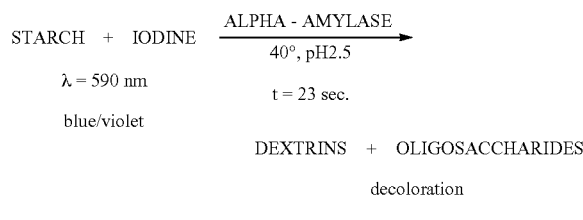

Standard Conditions/Reaction Conditions:
Substrate: Soluble starch, approx. 0.17 g/L
Buffer: Citrate, approx. 0.03 M
Iodine (I2): 0.03 g/L
$CaCl_2$: 1.85 mM
pH: 2.50±0.05
Incubation 40° C.
Temperature:
Reaction time: 23 seconds
Wavelength: 590 nm
Enzyme 0.025 AFAU/mL
Concentration:
Enzyme working 0.01-0.04 AFAU/mL
Range:

A folder EB-SM-0259.02/01 describing this analytical method in more detail is available upon request to Novozymes A/S, Denmark, which folder is hereby included by reference.

Determination of FAU-F

FAU-F Fungal Alpha-Amylase Units (Eungamyl) is measured relative to an enzyme standard of a declared strength.

| Reaction conditions | |
|---|---|
| Temperature | 37° C. |
| pH | 7.15 |
| Wavelength | 405 nm |
| Reaction time | 5 min |
| Measuring time | 2 min |

A folder (EB-SM-0216.02) describing this standard method in more detail is available on request from Novozymes A/S, Denmark, which folder is hereby included by reference.

Enzymes

Glucoamylase blend A: Blend comprising *Talaromyces emersonii* glucoamylase disclosed as SEQ ID NO: 34 in WO99/28448 and SEQ ID NO: 18 herein, *Trametes cingulata* glucoamylase disclosed as SEQ ID NO: 2 in WO 06/69289 and SEQ ID NO: 17, and *Rhizomucor pusillus* alpha-amylase with *Aspergillus niger* glucoamylase linker and starch binding domain (SBD) disclosed in SEQ ID NO: 16 herein having the following substitutions G128D+D143N using SEQ ID NO: 16 for numbering (activity ratio in AGU:AGU:FAU-F is about 29:8:1).

Example 1 Use of S53 Proteases in Conventional EtOH Production

Industrially liquefied mash was prepared with 3 ppm penicillin added from a 1 g/L stock, pH adjusted to 5.0 using 40% v/v $H_2SO_4$. No extra urea was added to the mash. The dry solids content of both mash preparations were measured on a Mettler-Toledo HB43-S moisture balance. Approximately 5 g of each prepared mash was aliquoted into pre-weighed 15 mL flip top tubes (Fisher) with 1/64" holes drilled into the lid for venting. Mash sample was dosed with diluted Glucoamylase blend A (0.019 AGU/µL) to an enzyme concentration of 0.6 AGU/g DS, as calculated by the following equation.

$$Enz.dose(ml) = \frac{Finalenz.dose(AGU/gDS) \times Mash\ weight(g) \times Solidcontent(\%\ DS/100)}{Conc.enzyme(AGU/ml)}$$

Each treatment from 1 to 15 (Table 1) was performed with 3 replicates.

TABLE 1

Enzyme and dose for each treatments for both 0 and 200 ppm urea liquefied mashes.

| | Protease | Dose | Units | Enzyme Family |
|---|---|---|---|---|
| 1 | Control | 0 | µg/gDS | |
| 2 | AP025 | 2 | µg/gDS | M35 |
| 3 | AP025 | 5 | µg/gDS | M35 |
| 4 | PfuS | 2 | µg/gDS | S8 |
| 5 | PfuS | 5 | µg/gDS | S8 |
| 6 | SEQ ID NO: 3 | 2 | µg/gDS | S53 |
| 7 | SEQ ID NO: 3 | 5 | µg/gDS | S53 |
| 8 | SEQ ID NO: 9 | 2 | µg/gDS | S53 |
| 9 | SEQ ID NO: 9 | 5 | µg/gDS | S53 |
| 10 | SEQ ID NO: 6 | 2 | µg/gDS | S53 |
| 11 | SEQ ID NO: 6 | 5 | µg/gDS | S53 |

TABLE 1-continued

Enzyme and dose for each treatments for
both 0 and 200 ppm urea liquefied mashes.

|    | Protease     | Dose | Units  | Enzyme Family |
|----|--------------|------|--------|---------------|
| 12 | SEQ ID NO: 15 | 2    | μg/gDS | S53           |
| 13 | SEQ ID NO: 15 | 5    | μg/gDS | S53           |
| 14 | SEQ ID NO: 12 | 2    | μg/gDS | S53           |
| 15 | SEQ ID NO: 12 | 5    | μg/gDS | S53           |

Two prior art proteases were included for comparison. AP025 is a metallo protease from *Thermoascus aurantiacus* disclosed as SEQ ID NO: 36, and PfuS is a serine protease from *Pyrococcus furiosus* disclosed as SEQ ID NO: 37.

Water was dosed into each sample such that the total added volume of enzyme and water was equal across each sample. Ethanol Red Star yeast was rehydrated by weighing 2.75 g of yeast placed in 50 mL of 32° C. tap water for 30 minutes. All samples were dosed with 100 μL of yeast solution, vortexed, and placed in a water bath set at 32° C. After 54 hours of fermentation, each sample was dosed with 50 μL of 40% sulfuric acid, vortexed, and centrifuged for 10 minutes at 3000×g then filtered into HPLC vials through 0.45 μm filters (Whatman). Samples were analyzed on an Agilent 1100/1200 series with Chemstation software. A Bio-Rad HPX-87H Ion Exclusion column 300 mm×7.8 mm with a cation H guard cartridge. Samples were run in the presence of 5 mM $H_2SO_4$ mobile phase at a flow rate of 0.6 ml/min at 65° C. The RI detector temperature was set at 55° C. The method quantifies several analytes using calibration standards for dextrins (DP4+), maltotriose, maltose, glucose, fructose, acetic acid, lactic acid, glycerol and ethanol. A 4 point calibration including the origin is used. Results are displayed in Table 2 (Control=no enzyme).

TABLE 2

Ethanol titer and percent change compared to the control
sample after 54 hours of fermentation with no urea and
with the addition of protease in either 2.0 or 5.0 μg ep/g
DS doses, Control = no protease enzyme addition.

|                      | 54 hr SSF |                  |
|----------------------|-----------|------------------|
| Sample (μg ep/g DS)  | EtOH (g/L) | % Change to Control |
| Control              | 108.6     |                  |
| AP025 (2)            | 119.7     | 10.3%            |
| AP025 (5)            | 127.1     | 17.1%            |
| PfuS (2)             | 113.2     | 4.3%             |
| PfuS (5)             | 121.2     | 11.6%            |
| SEQ ID NO: 3 (2)     | 132.5     | 22.1%            |
| SEQ ID NO: 3 (5)     | 136.2     | 25.4%            |
| SEQ ID NO: 9 (2)     | 132.6     | 22.2%            |
| SEQ ID NO: 9 (5)     | 137.4     | 26.5%            |
| SEQ ID NO: 6 (2)     | 126.9     | 16.9%            |
| SEQ ID NO: 6 (5)     | 130.2     | 20.0%            |
| SEQ ID NO: 15 (2)    | 129.7     | 19.4%            |
| SEQ ID NO: 15 (5)    | 134.3     | 23.7%            |
| SEQ ID NO: 12 (2)    | 130.1     | 19.8%            |
| SEQ ID NO: 12 (5)    | 132.5     | 22.1%            |

Conclusions

Addition of S53 proteases SEQ ID NO: 3, SEQ ID NO: 6, SEQ ID NO: 9, SEQ ID NO:12, SEQ ID NO: 15 was found to increase ethanol yield over other protease families on the fermentation of corn to ethanol at identical doses of either 2 or 5 μg ep/g DS.

Example 2: Use of S53 Proteases in Conventional EtOH Production

Industrially liquefied mash was prepared with the addition of 200 ppm urea added from a 200 g/L stock, 3 ppm penicillin added from a 1 g/L stock, and adjusted to pH 5.0 using 40% v/v $H_2SO_4$. The dry solids content of both mash preparations were measured on a Mettler-Toledo HB43-S moisture balance. Approximately 5 g of each prepared mash was aliquoted into pre-weighed 15 mL flip top tubes (Fisher) with 1/64" holes drilled into the lid for venting. Mash sample was dosed with diluted Glucoamylase blend A (0.019 AGU/μL) to an enzyme concentration of 0.6 AGU/g DS, as calculated by the following equation.

$$Enz.dose(\text{ml}) = \frac{Finalenz \cdot dose(AGU/gDS) \times \text{Mash weight}(g) \times Solidcontent(\% \ DS /100)}{Conc.enzyme(AGU/\text{ml})}$$

Each treatment from 1 to 15 (Table 3) was performed with 3 replicates.

TABLE 3

Enzyme and dose for each treatment
200 ppm urea liquefied mashes.

|    | Protease     | Dose | Units  | Enzyme Family |
|----|--------------|------|--------|---------------|
| 1  | Control      | 0    | μg/gDS |               |
| 2  | AP025        | 2    | μg/gDS | M35           |
| 3  | AP025        | 5    | μg/gDS | M35           |
| 4  | PfuS         | 2    | μg/gDS | S8            |
| 5  | PfuS         | 5    | μg/gDS | S8            |
| 6  | SEQ ID NO: 3 | 2    | μg/gDS | S53           |
| 7  | SEQ ID NO: 3 | 5    | μg/gDS | S53           |
| 8  | SEQ ID NO: 9 | 2    | μg/gDS | S53           |
| 9  | SEQ ID NO: 9 | 5    | μg/gDS | S53           |
| 10 | SEQ ID NO: 6 | 2    | μg/gDS | S53           |
| 11 | SEQ ID NO: 6 | 5    | μg/gDS | S53           |
| 12 | SEQ ID NO: 15 | 2   | μg/gDS | S53           |
| 13 | SEQ ID NO: 15 | 5   | μg/gDS | S53           |
| 14 | SEQ ID NO: 12 | 2   | μg/gDS | S53           |
| 15 | SEQ ID NO: 12 | 5   | μg/gDS | S53           |

Two prior art proteases were included for comparison. AP025 is a metallo protease from *Thermoascus aurantiacus* disclosed herein as SEQ ID NO: 36, and PfuS is a serine protease from *Pyrococcus furiosus* disclosed herein as SEQ ID NO: 37.

Water was dosed into each sample such that the total added volume of enzyme and water was equal across each sample. Ethanol Red Star yeast was rehydrated by weighing 2.75 g of yeast placed in 50 mL of 32° C. tap water for 30 minutes. All samples were dosed with 100 μL of yeast solution, vortexed, and placed in a water bath set at 32° C. After 54 hours of fermentation, each sample was dosed with 50 μL of 40% sulfuric acid, vortexed, and centrifuged for 10 minutes at 3000×g then filtered into HPLC vials through 0.45 μm filters (Whatman). Samples were analyzed on an Agilent 1100/1200 series with Chemstation software. A Bio-Rad HPX-87H Ion Exclusion column 300 mm×7.8 mm with a cation H guard cartridge. Samples were run in the presence of 5 mM $H_2SO_4$ mobile phase at a flow rate of 0.6 ml/min at 65° C. The RI detector temperature was set at 55° C. The method quantifies several analytes using calibration standards for dextrins (DP4+), maltotriose, maltose, glucose, fructose, acetic acid, lactic acid, glycerol and ethanol.

A 4 point calibration including the origin is used. Results are displayed in Table 4 (Control=no enzyme).

TABLE 4

Ethanol titer and percent change compared to the control sample after 54 hours of fermentation with 200 ppm added urea and with the addition of protease in either 2.0 or 5.0 μg ep/g DS doses, Control = no protease enzyme addition.

| Sample (μg ep/g DS) | 54 hrs SSF | |
|---|---|---|
| | EtOH (g/L) | % Change to Control |
| Control | 122.7 | |
| AP025 (2) | 131.7 | 7.3% |
| AP025 (5) | 134.4 | 9.5% |
| PfuS (2) | 127.8 | 4.2% |
| PfuS (5) | 132.0 | 7.6% |
| SEQ ID NO: 3 (2) | 139.6 | 13.8% |
| SEQ ID NO: 3 (5) | 142.0 | 15.8% |
| SEQ ID NO: 9 (2) | 137.6 | 12.2% |
| SEQ ID NO: 9 (5) | 141.1 | 15.1% |
| SEQ ID NO: 6 (2) | 133.0 | 8.4% |
| SEQ ID NO: 6 (5) | 137.1 | 11.8% |
| SEQ ID NO: 15 (2) | 135.9 | 10.8% |
| SEQ ID NO: 15 (5) | 140.8 | 14.8% |
| SEQ ID NO: 12 (2) | 137.3 | 11.9% |
| SEQ ID NO: 12 (5) | 140.6 | 14.6% |

Conclusion

Addition of S53 proteases SEQ ID NO: 3, SEQ ID NO: 6, SEQ ID NO: 9, SEQ ID NO:12, SEQ ID NO: 15 were shown to increase ethanol yield over other protease families on the fermentation of corn to ethanol.

Example 3: Use of S53 Proteases in Raw Starch Hydrolysis and Fermentation

Milled corn at a dry solids level of 34.51% was supplemented with 3 ppm lactrol and 200 ppm urea. The slurry was adjusted to pH 4.5 with 40% $H_2SO_4$. Approximately 70 g of this slurry was added to 125 mL tubes Wheaton flasks that had 1/16" holes drilled in the caps for venting. Each flask was dosed with enzymes according to Table 5, followed by 450 μL rehydrated yeast per jar of slurry (5.5 g Fermentis Ethanol Red yeast in 100 mL $H_2O$, incubated for 30 min at 32° C.). The glucoamylase used is a wild type glucoamylase derived from *Pycnoporus sanguineus* and shown in SEQ ID NO: 19 denoted PsAMG, and the alpha-amylase used is a variant *Rhizomucor pusillus* alpha-amylase with *Aspergillus niger* glucoamylase linker and starch binding domain (SBD) disclosed in SEQ ID NO: 16 herein having the following substitutions G128D+D143N using SEQ ID NO: 16 for numbering and denoted PE096. A prior art proteases, AP025, was included for comparison. AP025 is a metallo protease from *Thermoascus aurantiacus* and is disclosed in WO2003/048353 and in SEQ ID NO: 36 herein.

Water was dosed into each sample such that the total added volume of enzyme and water was equal across each sample. Actual enzyme dosages were based on the exact weight of corn slurry in each tube according to the following formula:

$$Enz.dose(\mu L) = \frac{\text{Final } enz.dose(mg/g \ DS) \times \text{Mash weight}(g) \times \text{Dry solid content } (\% \ DS) \times 1000}{\text{Stock enzyme } conc. \ (mg/mL)}$$

Table 5 shows 7 different enzyme treatments that had two replicates per treatment.

| Gluco-Amylase | Dose | Units | Alpha-amylase | Dose | Units | Protease | Dose | Units |
|---|---|---|---|---|---|---|---|---|
| PsAMG | 0.50 | AGU/g DS | PE096 | 0.0313 | FAUF/g DS | | 0.0 | |
| PsAMG | 0.50 | AGU/g DS | PE096 | 0.0313 | FAUF/g DS | AP025 | 5.0 | μg/g DS |
| PsAMG | 0.50 | AGU/g DS | PE096 | 0.0313 | FAUF/g DS | SEQ ID NO: 3 | 5.0 | μg/g DS |
| PsAMG | 0.50 | AGU/g DS | PE096 | 0.0313 | FAUF/g DS | SEQ ID NO: 9 | 5.0 | μg/g DS |
| PsAMG | 0.50 | AGU/g DS | PE096 | 0.0313 | FAUF/g DS | SEQ ID NO: 6 | 5.0 | μg/g DS |
| PsAMG | 0.50 | AGU/g DS | PE096 | 0.0313 | FAUF/g DS | SEQ ID NO: 15 | 5.0 | μg/g DS |
| PsAMG | 0.50 | AGU/g DS | PE096 | 0.0313 | FAUF/g DS | SEQ ID NO: 12 | 5.0 | μg/g DS |

Flasks were swirled morning and evening. For sample collection, approx. 4 grams of mash was removed at 24, 48 and 72 hour time points. The HPLC preparation consisted of stopping the reaction by addition of 10 μL of 40% $H_2SO_4$ per gram mash (40 μL total), centrifuging for 10 min at 1462×g, and filtering through a 0.45 μm filters (Whatman). Samples were analyzed on an Agilent 1100/1200 series with Chemstation software. A Bio-Rad HPX-87H Ion Exclusion column 300 mm×7.8 mm with a cation H guard cartridge. Samples were run in the presence of 5 mM $H_2SO_4$ mobile phase at a flow rate of 0.6 ml/min at 65° C. The RI detector temperature was set at 55° C. The method quantifies several analytes using calibration standards for dextrins (DP4+), maltotriose, maltose, glucose, fructose, acetic acid, lactic acid, glycerol and ethanol. A 4 point calibration including the origin is used. Results are displayed in Table 6 below.

TABLE 6

Bar graph demonstrating Ethanol (g/L) yield and percent change from control is showfor each sample.

| | 24 hours | | 48 hours | | 72 hours | |
|---|---|---|---|---|---|---|
| Sample | EtOH (g/L) | % Change (0.5 PsAMG) | EtOH (g/L) | % Change (0.5 PsAMG) | EtOH (g/L) | % Change (0.5 PsAMG) |
| 0.5 PsAMG | 92.3 | 0.00% | 129.8 | 0.00% | 144.1 | 0.00% |
| 0.5 PsAMG + AP025 | 93.6 | 1.40% | 131.9 | 1.60% | 144.8 | 0.48% |
| 0.5 PsAMG + SEQ ID NO: 3 | 94.3 | 2.15% | 132.9 | 2.36% | 145.8 | 1.18% |
| 0.5 PsAMG + SEQ ID NO: 9 | 94.3 | 2.17% | 133.4 | 2.73% | 145.8 | 1.23% |
| 0.5 PsAMG + SEQ ID NO: 6 | 93.8 | 1.58% | 132.4 | 1.96% | 145.3 | 0.84% |
| 0.5 PsAMG + SEQ ID NO: 15 | 94.7 | 2.54% | 133.0 | 2.40% | 145.0 | 0.62% |
| 0.5 PsAMG + SEQ ID NO: 12 | 94.9 | 2.75% | 133.5 | 2.80% | 145.7 | 1.11% |

24 & 48 Hours

Data suggests that the use of the protease benefits early fermentations, increasing the kinetics by improving yeast metabolism.

The S53 proteases SEQ ID NO: 3, SEQ ID NO: 6, SEQ ID NO: 9, SEQ ID NO:12, SEQ ID NO: 15 outperform AP025.

72 Hours

The proteases SEQ ID NO: 3, SEQ ID NO: 6, SEQ ID NO: 9, SEQ ID NO:12, SEQ ID NO: 15 produced more ethanol compared to the control (0.5 PsAMG—no protease) and AP025.

Example 4: Use of S53 Proteases in Conventional EtOH Production

Industrially liquefied mash was prepared with the addition of 200 ppm urea added from a 200 g/L stock, 3 ppm penicillin added from a 1 g/L stock, and adjusted to pH 5.0 using 40% v/v $H_2SO_4$. The dry solids content of both mash preparations were measured on a Mettler-Toledo HB43-S moisture balance. Approximately 5 g of each prepared mash was aliquoted into pre-weighed 15 mL flip top tubes (Fisher) with 1/64" holes drilled into the lid for venting. Mash sample was dosed with diluted Glucoamylase blend A (0.019 AGU/µL) to an enzyme concentration of 0.6 AGU/g DS, as calculated by the following equation.

$$Enz.dose(ml) = \frac{Finalenz.dose(AGU/gDS) \times Mash\ weight(g) \times Solidcontent\ (\%\ DS/100)}{Conc.enzyme(AGU/ml)}$$

Each treatment from 1 to 6 (Table 1) was performed with 3 replicates.

TABLE 1

Enzyme and dose for each treatment 200 ppm urea liquefied mashes.

| | Protease | Dose | Units | Enzyme Family |
|---|---|---|---|---|
| 1 | Control | 0 | µg/gDS | |
| 2 | Mg proIII | 2.5 | µg/gDS | S53 |
| 3 | Mg proIII | 5 | µg/gDS | S53 |
| 4 | SEQ ID NO: 35 | 5 | µg/gDS | S53 |
| 5 | SEQ ID NO: 27 | 5 | µg/gDS | S53 |
| 6 | SEQ ID NO: 31 | 5 | µg/gDS | S53 |

One prior art proteases were included for comparison. Mg ProIII is S53 protease from *Meripilus giganteus* disclosed herein as SEQ ID NO: 3.

Water was dosed into each sample such that the total added volume of enzyme and water was equal across each sample. Ethanol Red Star yeast was rehydrated by weighing 2.75 g of yeast placed in 50 mL of 32° C. tap water for 30 minutes. All samples were dosed with 100 µL of yeast solution, vortexed, and placed in a water bath set at 32° C. After 54 hours of fermentation, each sample was dosed with 50 µL of 40% sulfuric acid, vortexed, and centrifuged for 10 minutes at 3000×g then filtered into HPLC vials through 0.45 µm filters (Whatman). Samples were analyzed on an Agilent 1100/1200 series with Chemstation software. A Bio-Rad HPX-87H Ion Exclusion column 300 mm×7.8 mm with a cation H guard cartridge. Samples were run in the presence of 5 mM $H_2SO_4$ mobile phase at a flow rate of 0.6 ml/min at 65° C. The RI detector temperature was set at 55° C. The method quantifies several analytes using calibration standards for dextrins (DP4+), maltotriose, maltose, glucose, fructose, acetic acid, lactic acid, glycerol and ethanol. A 4 point calibration including the origin is used. Results are displayed in Table 2 (Control=no enzyme).

TABLE 2

Ethanol titer and percent change compared to the control sample after 54 hours of fermentation with 200 ppm added urea and with the addition of protease in either 2.5 or 5.0 µg ep/g DS doses, Control = no protease enzyme addition.

| | 54 hrs SSF | |
|---|---|---|
| Sample (µg ep/g DS) | EtOH (g/L) | % Change to Control |
| Control | 101.54 | |
| Mg ProIII(2.5) | 120.42 | 18.6% |
| Mg ProIII(5) | 121.90 | 20.1% |
| SEQ ID NO: 35 (5) | 120.94 | 19.1% |
| SEQ ID NO: 27 (5) | 119.06 | 17.3% |
| SEQ ID NO: 31 (5) | 121.39 | 19.5% |

Conclusion

Addition of S53 proteases from *Bacillus* sp. 19138 (SEQ ID NO: 35), *Ganoderma lucidum* (SEQ ID NO: 27), and *Neolentinus lepideus* (SEQ ID NO: 31), were shown to increase ethanol yield over other protease families on the fermentation of corn to ethanol.

In a similar setup two additional S53 proteases, one from *Lecanicillium* sp. WMM742 (SEQ ID NO: 38) and another from *Talaromyces proteolyticus* (SEQ ID NO: 39) were tested as described above. The results and the dosing is shown in Table 3 below.

TABLE 3

Ethanol titer and percent change compared to the control sample after 54 hours of fermentation with 200 ppm added urea and with the addition of protease in either 2.5 or 5.0 μg ep/g DS doses, Control = no protease enzyme addition.

| Sample (μg ep/g DS) | 54 hrs SSF | |
|---|---|---|
| | EtOH (g/L) | % Change to Control |
| Control | 77.45 | |
| Mg ProIII(2.5) | 105.45 | 36.15% |
| Mg ProIII(5) | 110.13 | 42.19% |
| Amino acids 195 to 560 of SEQ ID NO: 38 (5) | 114.63 | 48.01% |
| Amino acids 226 to 647 of SEQ ID NO: 39 (5) | 112.49 | 45.24% |

Conclusion

Addition of S53 proteases from *Lecanicillium* sp. WMM742 (SEQ ID NO: 38) and from *Talaromyces proteolyticus* (SEQ ID NO: 39), were shown to increase ethanol yield compared to the MgProIII protease control in the fermentation of corn to ethanol.

Example 5: Cloning and Expression of S53 Proteases Used in the Examples

WO2014/037438 discloses cloning and expression of serine proteases, S53, derived from *Meripilus giganteus*, *Trametes versicolor*, and *Dichomitus squalens*.

Cloning and Expression of a S53 Protease from *Polyporus arcularius*:

Gene

The genomic DNA sequence of a S53 protease polypeptide was identified in the complete genome of *Polyporus arcularius* which was recently made public available on the JGI Genome Portal (The Genome Portal of the Department of Energy Joint Genome Institute. Grigoriev I V, Nordberg H, Shabalov I, Aerts A, Cantor M, Goodstein D, Kuo A, Minovitsky S, Nikitin R, Ohm R A, Otillar R, Poliakov A, Ratnere I, Riley R, Smirnova T, Rokhsar D, Dubchak I. Nucleic Acids Res. 2012 January; 40(Database issue):D26-32). The genomic DNA sequence of 1943 nucleotides contains 4 introns of 68 bp (nucleotides 262 to 329), 61 bp (nucleotides 933 to 993), 55 bp (nucleotides 1194 to 1248), and 55 bp (nucleotides 1387 to 1441). The genomic DNA fragment encodes a polypeptide of 567 amino acids. A synthetic gene without introns designed to encode the *Polyporus arcularius* S53 protease and codon optimized for expression in *Aspergillus oryzae* was purchased from GeneArt (Invitrogen) and shown as SEQ ID NO: 23.

Expression Vector

The *Aspergillus* expression vector pDau109 (WO 2005/042735) consists of an expression cassette based on the partly duplicated *Aspergillus niger* neutral amylase II (NA2) promoter fused to the *Aspergillus nidulans* triose phosphate isomerase non translated leader sequence (Pna2/tpl) and the *Aspergillus niger* amyloglycosidase terminator (Tamg). Also present on the vector is the *Aspergillus* selective marker amdS from *Aspergillus nidulans* enabling growth on acetamide as sole nitrogen source and the amplicillin resistance gene (beta lactamase) allowing for facile selection for positive recombinant *E. coli* clones using commercially available and highly competent strains on commonly used LB ampicillin plates. pDau109 contains a multiple cloning site situated between the promoter region and terminator, allowing for insertion of the gene of interest in front of the promoter region.

Expression Cloning

The synthetic gene encoding the *Polyporus arcularius* S53 protease was cloned into the pDau109 *Aspergillus* expression vector using the unique restriction sites BamHI and HindIII and transformed into *E. coli* (Top10, Invitrogen). Expression plasmids containing the insert were purified from the *E. coli* transformants, and sequenced with vector primers and gene specific primers in order to determine a representative plasmid expression clone that was free of PCR errors. The plasmid expression done was transformed into *A. oryzae* and a recombinant *A. oryzae* clone containing the integrated expression construct were grown in liquid culture. The enzyme containing supernatant was sterile filtered and used for further characterization.

Cloning and Expression of a S53 Protease from *Lenzites Betulinus*:

Gene

A fungal strain was isolated and based on both morphological and molecular characterization (ITS sequencing) classified as *Lenzites betulinus*. The *Lenzites betulinus* strain was annotated as *Lenzites betulinus* strain NN042749 (environmental sample collected in Denmark 24 Jul. 2013) and fully genome sequenced. The genomic DNA sequence of a S53 protease polypeptide encoding sequence was identified in the genome of *Lenzites betulinus* strain NN042749. The genomic DNA sequence of 2093 nucleotides contains 7 introns of 59 bp (nucleotides 259 to 317), 52 bp (nucleotides 584 to 635), 61 bp (nucleotides 859 to 919), 55 bp (nucleotides 1031 to 1085), 53 bp (nucleotides 1286 to 1338), 56 bp (nucleotides 1477 to 1532), and 59 bp (nucleotides 1978 to 2036). The genomic DNA fragment encodes a polypeptide of 565 amino acids. A synthetic gene without introns designed to encode the *Lenzites betulinus* S53 protease and codon optimized for expression in *Aspergillus oryzae* was purchased from GeneArt (Invitrogen) and shown in SEQ ID NO: 24.

Expression Vector

The *Aspergillus* expression vector pDau109 (WO 2005/042735) consists of an expression cassette based on the partly duplicated *Aspergillus niger* neutral amylase II (NA2) promoter fused to the *Aspergillus nidulans* those phosphate isomerase non translated leader sequence (Pna2/tpl) and the *Aspergillus niger* amyloglycosidase terminator (Tamg). Also present on the vector is the *Aspergillus* selective marker amdS from *Aspergillus nidulans* enabling growth on acetamide as sole nitrogen source and the amplicillin resistance gene (beta lactamase) allowing for facile selection for positive recombinant *E. coli* clones using commercially available and highly competent strains on commonly used LB ampicillin plates. pDau109 contains a multiple cloning site situated between the promoter region and terminator, allowing for insertion of the gene of interest in front of the promoter region.

Expression Cloning

The synthetic gene encoding the *Lenzites betulinus* S53 protease was cloned into the pDau109 *Aspergillus* expression vector using the unique restriction sites BamHI and HindIII and transformed into *E. coli* (Top10, Invitrogen). Expression plasmids containing the insert were purified from the *E. coli* transformants, and sequenced with vector primers and gene specific primers in order to determine a representative plasmid expression clone that was free of PCR errors. The plasmid expression clone was transformed into *A. oryzae* and a recombinant *A. oryzae* clone containing the integrated expression construct were grown in liquid culture. The enzyme containing supernatant was sterile filtered and used for further characterization.

Cloning and Expression of a S53 Protease from *Ganoderma lucidum* Xiananoa No. 1 Disclosed as SEQ ID NO: 25
Gene The genomic DNA sequence of a S53 protease polypeptide was identified in the complete genome of *Ganoderma lucidum* which was published by Liu D., Gong J., Dai W., Kang X., Huang Z., Zhang H. M., Liu W., Liu L., Ma J., Xia Z., Chen Y., Chen Y., Wang D., Ni P., Guo A. Y., Xiong X. (2012). The Genome of *Ganderma lucidum* Provide Insights into Triterpense Biosynthesis and Wood Degradation. PLoS ONE, 7(5), e36146. http://doi.org/10.1371/journal.pone.0036146. The genomic DNA sequence and deduced amino acid sequence of the *Ganoderma lucidum* S53 protease polypeptide encoding sequence are shown in SEQ ID NO: 25 and SEQ ID NO: 26, respectively. The genomic DNA sequence of 1880 nucleotides contains 3 introns of 66 bp (nucleotides 259 to 324), 64 bp (nucleotides 820 to 883), and 52 bp (nucleotides 1192 to 1243). The genomic DNA fragment encodes a polypeptide of 565 amino acids. A synthetic gene without introns designed to encode the *Ganoderma lucidum* S53 protease and codon optimized for expression in *Aspergillus oryzae* was purchased from GeneArt (Invitrogen) SEQ ID NO: 28.
Expression Vector The *Aspergillus* expression vector pDau109 (WO 2005/042735) consists of an expression cassette based on the partly duplicated *Aspergillus niger* neutral amylase II (NA2) promoter fused to the *Aspergillus nidulans* triose phosphate isomerase non translated leader sequence (Pna2/tpl) and the *Aspergillus niger* amyloglycosidase terminator (Tamg). Also present on the vector is the *Aspergillus* selective marker amdS from *Aspergillus nidulans* enabling growth on acetamide as sole nitrogen source and the amplicillin resistance gene (beta lactamase) allowing for facile selection for positive recombinant *E. coli* clones using commercially available and highly competent strains on commonly used LB ampicillin plates. pDau109 contains a multiple cloning site situated between the promoter region and terminator, allowing for insertion of the gene of interest in front of the promoter region.
Expression Cloning The synthetic gene encoding the *Ganoderma lucidum* S53 protease (SEQ ID NO: 28) was cloned into the pDau109 *Aspergillus* expression vector using the unique restriction sites BamHI and HindIII and transformed into *E. coli* (Top10, Invitrogen). Expression plasmids containing the insert were purified from the *E. coli* transformants, and sequenced with vector primers and gene specific primers in order to determine a representative plasmid expression clone that was free of PCR errors. The plasmid expression clone was transformed into *A. oryzae* and a recombinant *A. oryzae* clone containing the integrated expression construct were grown in liquid culture. The enzyme containing supernatant was sterile filtered and used for further characterization.
Cloning and Expression of a S53 Protease from *Neolentinus lepideus* Disclosed as SEQ ID NO: 29
Gene A fungal strain was isolated and based on both morphological and molecular characterization (ITS sequencing) classified as *Neolentinus lepideus*. The *Neolentinus lepideus* strain was annotated as *Neolentinus lepideus* strain NN055916 (environmental sample NN055916 collected in Denmark 14 Jul. 2008) and fully genome sequenced. The genomic DNA sequence of a S53 protease polypeptide encoding sequence was identified in the genome of *Neolentinus lepideus* strain NN055916 and the genomic DNA sequence and deduced amino acid sequence are shown in SEQ ID NO: 29 and SEQ ID NO: 30, respectively. The genomic DNA sequence of 2048 nucleotides contains 6 introns of 56 bp (nucleotides 262 to 317), 60 bp (nucleotides 584 to 643), 68 bp (nucleotides 972 to 1039), 53 bp (nucleotides 1240 to 1292), 53 bp (nucleotides 1434 to 1486), and 60 bp (nucleotides 1876 to 1935). The genomic DNA fragment encodes a polypeptide of 565 amino acids. A synthetic gene without introns designed to encode the *Neolentinus lepideus* S53 protease and codon optimized for expression in *Aspergillus oryzae* was purchased from GeneArt (Invitrogen) SEQ ID NO: 32.
Expression Vector The *Aspergillus* expression vector pDau109 (WO 2005/042735) consists of an expression cassette based on the partly duplicated *Aspergillus niger* neutral amylase II (NA2) promoter fused to the *Aspergillus nidulans* triose phosphate isomerase non translated leader sequence (Pna2/tpl) and the *Aspergillus niger* amyloglycosidase terminator (Tamg). Also present on the vector is the *Aspergillus* selective marker amdS from *Aspergillus nidulans* enabling growth on acetamide as sole nitrogen source and the ampicillin resistance gene (beta lactamase) allowing for facile selection for positive recombinant *E. coli* clones using commercially available and highly competent strains on commonly used LB ampicillin plates. pDau109 contains a multiple cloning site situated between the promoter region and terminator, allowing for insertion of the gene of interest in front of the promoter region.
Expression Cloning The synthetic gene encoding the *Neolentinus lepideus* S53 protease (SEQ ID NO: 32) was cloned into the pDau109 *Aspergillus* expression vector using the unique restriction sites BamHI and HindIII and transformed into *E. coli* (Top10, Invitrogen). Expression plasmids containing the insert were purified from the *E. coli* transformants, and sequenced with vector primers and gene specific primers in order to determine a representative plasmid expression clone that was free of PCR errors. The plasmid expression clone was transformed into *A. oryzae* and a recombinant *A. oryzae* clone containing the integrated expression construct were grown in liquid culture. The enzyme containing supernatant was sterile filtered and used for further characterization.

Example 6: Determination of Protease Activity for Proteases Disclosed as SEQ ID NO: 12, SEQ ID NO: 15, SEQ ID NO: 27, and SEQ ID NO: 31

A kinetic Suc-AAPL-pNA assay was used for obtaining the pH-activity profile.

An endpoint Suc-AAPL-pNA assay was used for obtaining the pH-stability profile and the temperature profile at pH 4.0. For the pH-stability profile the protease was diluted 7× in the assay buffers and incubated for 2 hours at 37° C. After incubation the protease samples were transferred to the same pH, before assay for residual activity, by dilution in the pH 4 Assay buffer.
Assays
Protease Assays
Kinetic Suc-AAPL-pNA Assay for pH-Activity Profile:
pNA substrate: Suc-AAPL-pNA (Bachem L-1390).
Temperature: Room temperature (25° C.)
Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

20 µl protease (diluted in 0.01% Triton X-100) was mixed with 100 µl assay buffer. The assay was started by adding 100 µl pNA substrate (50 mg dissolved in 1.0 ml DMSO and further diluted 45× with 0.01% Triton X-100). The increase in $OD_{40}$ was monitored as a measure of the protease activity.

End-Point Assay for Temperature Profile and for DH-Stability Profile:

pNA substrate: Suc-AAPL-pNA (Bachem L-1390).

Temperature: controlled.

Assay buffers: 100 mM succinic acid, 100 mM HEPES, 100 mM CHES, 100 mM CABS, 1 mM $CaCl_2$, 150 mM KCl, 0.01% Triton X-100 adjusted to pH-values 2.0, 3.0, 4.0, 5.0, 6.0, 7.0, 8.0, 9.0, 10.0, and 11.0 with HCl or NaOH.

200 µl pNA substrate (50 mg dissolved in 1.0 ml DMSO and further diluted 50× with the Assay buffers) were pipetted in an Eppendorf tube and placed on ice. 20 µl peptidase sample (diluted in 0.01% Triton X-100) was added. The assay was initiated by transferring the Eppendorf tube to an Eppendorf thermomixer, which was set to the assay temperature. The tube was incubated for 15 minutes (1 hour for pH-stability profile) on the Eppendorf thermomixer at its highest shaking rate (1400 rpm). The incubation was stopped by transferring the tube back to the ice bath and adding 600 µl 500 mM $H_3BO_3$/NaOH, pH 9.7. 200 µl supernatant was transferred to a microtiter plate. $OD_{405}$ was read as a measure of peptidase activity. A buffer blind was included in the assay (instead of enzyme).

Results:

The protease disclosed as SEQ ID NO: 12 (*Polyporus arcularius*) was shown to have optimum activity in the range from pH 3-4, a pH stability profile with an optimum at pH 3-6, and a temperature optimum at around 50° C., pH 4.

The protease disclosed as SEQ ID NO: 15 (*Lenzites betulinus*) was shown to have optimum activity at around pH 3, a pH stability profile with an optimum at pH 3-5, and a temperature optimum at around 50° C., pH 4.

The protease disclosed as SEQ ID NO: 27 (*Ganoderma lucidum* Xiangnong No. 1) was shown to have optimum activity around pH 4, a pH stability profile with an optimum at pH 4-5, and a temperature optimum at around 50° C., pH 4.

The protease disclosed as SEQ ID NO: 31 (*Neolentinus lepideus*) was shown to have optimum activity at pH 3-4, a pH stability profile with an optimum at pH 3-5, and a temperature optimum at around 50° C., pH 4.

Example 7: Determination of the N-Terminal of Mature Polypeptide

The mature sequence, based on EDMAN N-terminal sequencing data and Intact MS data was determined to be amino acids 202-567 of SEQ ID NO: 11 (disclosed herein as SEQ ID NO: 12).

The relative molecular weight as determined by SDS-PAGE was approx. $M_r$=48 kDa.

The mature sequence, based on EDMAN N-terminal sequencing data and Intact MS data was determined to be amino acids 200-565 of SEQ ID NO: 14 (disclosed herein as SEQ ID NO: 15).

The relative molecular weight as determined by SDS-PAGE was approx. $M_r$=43 kDa.

The invention claimed is:

1. A process for producing a fermentation product from starch-containing material comprising simultaneously saccharifying and fermenting starch-containing material using a carbohydrate-source generating enzymes and a fermenting organism at a temperature below the initial gelatinization temperature of said starch-containing material in the presence of a serine protease having at least 96% sequence identity to the mature polypeptide of SEQ ID NO: 3.

2. A process for producing a fermentation product from starch-containing material comprising the steps of:
   (a) liquefying starch-containing material in the presence of an alpha-amylase;
   (b) saccharifying the liquefied material obtained in step (a) using a carbohydrate-source generating enzyme;
   (c) fermenting using a fermenting organism;
wherein a serine protease having at least 85% sequence identity to the mature polypeptide of SEQ ID NO: 3 is present during step b) and/or c).

3. The process of claim 1, wherein the fermentation product is an alcohol.

4. The process of claim 1, wherein the fermentation product is ethanol.

5. The process of claim 1, wherein the fermentation product is fuel ethanol.

6. The process of claim 1, wherein the starch-containing material comprises granular starch.

7. The process of claim 1, wherein the starch-containing material comprises granular starch from corn.

8. The process of claim 2, wherein the fermentation product is an alcohol.

9. The process of claim 2, wherein the fermentation product is ethanol.

10. The process of claim 2, wherein the fermentation product is fuel ethanol.

11. The process of claim 2, wherein the starch-containing material is corn.

12. The process of claim 2, wherein liquefying step (a) is performed at a temperature between 70-95 degrees centigrade.

13. The process of claim 2, wherein liquefying step (a) is performed at a temperature between 80-90 degrees centigrade.

14. The process of claim 2, wherein liquefying step (a) is performed at a pH between 4 and 7.

15. The process of claim 2, wherein liquefying step (a) is performed at a pH between 4.5 and 5.5.

* * * * *

SEQUENCE LISTING

```
<160> NUMBER OF SEQ ID NOS: 39

<210> SEQ ID NO 1
<211> LENGTH: 1695
<212> TYPE: DNA
<213> ORGANISM: Meripilus giganteus

<400> SEQUENCE: 1
atggtcgcca ccagcttgct cgttgcctcc ctattcacgc tcgccctcgg cacgccgacg      60
ggtcgcaacc tcaagctgca cgaggcgcgc gaagaccttc tgccggttt ctcgctgcgc      120 ggcgccgcct cgcccgacac gacgctgaag ctccgcatcg cgctcgtgca gaacaacttc     180
gccgagctcg aagacaagct ctacgacgtc agcacaccgt ccagcgccaa ctacggcaac     240
cacctctcga aggaagaggt tgagcagtac attgctccgg ctcccgagag cgtgaaagcc     300
gtgaatgcct ggctcaccga aacggactc gacgcgcaca ccatttcgcc cgccggcgac      360
tggctcgcat tcgaggtccc cgtcagcaag gcgaatgagc tcttcgacgc cgacttctcc     420
gtgtttaccc acgatgagtc cggcctcgag gctatccgga cgctggccta ctccatccct     480
gctgagcttc agggacacct cgaccttgtt cacccccaccg tcacgttccc gaacccccaat   540 gcgcacctgc ccgtcgtgcg ctccacccag cccatccgga acctgaccgg acgtgctata    600
ccggcctctt gcgcgagcac catcacccct gcgtgcttgc aggccatcta cggtatcccc    660
accaccaagg ctactcagtc ctcgaacaag ctcgctgtca gcggcttcat cgaccagttt   720
gcgaacaagg ctgacctgaa gtcattcctg gcccagttcc gcaaagacat ctcatcctcc    780
acgactttct cgcttcagac tctcgatggt ggagagaacg accagagccc tagcgaggcg     840
ggtatcgagg ctaacttgga tatccagtac accgtcggcc tcgccacggg cgtccctacc     900
acgttcatct ccgtcggcga cgacttccag gatggcaact tggagggctt cctggacatc    960
```

```
atcaacttct tgctcggcga gagcaacccg ccgcaggtcc tcaccaccag ttacggccag    1020
aacgagaaca cgatctcggc caagcttgct aaccaacttt gcaatgcgta cgctcagctc    1080
ggcgcgcgcg gcacctctat cctcttcgcg tcgggtgatg gcggtgtgtc cggctcgcag    1140
tccgcgcact gcagcaattt tgtcccgaca ttccccctccg gctgcccctt catgacttcc    1200
gtcggcgcga cgcagggcgt cagccccgag actgccgccg ccttctcatc cggcggcttc    1260
tcgaacgtgt tcggcatccc gtcgtaccag gcttccgcgg tcagcggcta cctgtccgcg    1320
ctcggaagca cgaactcggg caagttcaac cgcagcggac gcggattccc cgacgtctcc    1380
acgcaaggcg tggacttcca gatcgtcagc ggcggccaga cgatcggcgt cgacggcacg    1440
agctgcgcca gcccgacgtt cgcgagcgtc atctcgctgg taaacgaccg cctcatcgcg    1500
gccggcaaga gcccgctcgg cttcctgaac cccttcctgt actcgtcggc gggcaaggcc    1560
gcgctcaacg acgtcacgag tggctcgaac cctggctgca gcacgaacgg cttccccgct    1620
aaggccggct gggacccggt cactggtctt ggcacgccca actttgccaa gctcctcacc    1680
gcggtcggcc tgtga                                                     1695
```

<210> SEQ ID NO 2
<211> LENGTH: 564
<212> TYPE: PRT
<213> ORGANISM: Meripilus giganteus

<400> SEQUENCE: 2

```
Met Val Ala Thr Ser Leu Leu Val Ala Ser Leu Phe Thr Leu Ala Leu
1               5                   10                  15

Gly Thr Pro Thr Gly Arg Asn Leu Lys Leu His Glu Ala Arg Glu Asp
            20                  25                  30

Leu Pro Ala Gly Phe Ser Leu Arg Gly Ala Ala Ser Pro Asp Thr Thr
        35                  40                  45

Leu Lys Leu Arg Ile Ala Leu Val Gln Asn Asn Phe Ala Glu Leu Glu
    50                  55                  60

Asp Lys Leu Tyr Asp Val Ser Thr Pro Ser Ser Ala Asn Tyr Gly Asn
65                  70                  75                  80

His Leu Ser Lys Glu Glu Val Glu Gln Tyr Ile Ala Pro Ala Pro Glu
                85                  90                  95

Ser Val Lys Ala Val Asn Ala Trp Leu Thr Glu Asn Gly Leu Asp Ala
            100                 105                 110

His Thr Ile Ser Pro Ala Gly Asp Trp Leu Ala Phe Glu Val Pro Val
        115                 120                 125

Ser Lys Ala Asn Glu Leu Phe Asp Ala Asp Phe Ser Val Phe Thr His
    130                 135                 140

Asp Glu Ser Gly Leu Glu Ala Ile Arg Thr Leu Ala Tyr Ser Ile Pro
145                 150                 155                 160

Ala Glu Leu Gln Gly His Leu Asp Leu Val His Pro Thr Val Thr Phe
                165                 170                 175

Pro Asn Pro Asn Ala His Leu Pro Val Val Arg Ser Thr Gln Pro Ile
            180                 185                 190

Arg Asn Leu Thr Gly Arg Ala Ile Pro Ala Ser Cys Ala Ser Thr Ile
        195                 200                 205

Thr Pro Ala Cys Leu Gln Ala Ile Tyr Gly Ile Pro Thr Thr Lys Ala
    210                 215                 220

Thr Gln Ser Ser Asn Lys Leu Ala Val Ser Gly Phe Ile Asp Gln Phe
225                 230                 235                 240
```

Ala Asn Lys Ala Asp Leu Lys Ser Phe Leu Ala Gln Phe Arg Lys Asp
            245                 250                 255

Ile Ser Ser Ser Thr Thr Phe Ser Leu Gln Thr Leu Asp Gly Gly Glu
            260                 265                 270

Asn Asp Gln Ser Pro Ser Glu Ala Gly Ile Glu Ala Asn Leu Asp Ile
            275                 280                 285

Gln Tyr Thr Val Gly Leu Ala Thr Gly Val Pro Thr Thr Phe Ile Ser
        290                 295                 300

Val Gly Asp Asp Phe Gln Asp Gly Asn Leu Glu Gly Phe Leu Asp Ile
305                 310                 315                 320

Ile Asn Phe Leu Leu Gly Glu Ser Asn Pro Pro Gln Val Leu Thr Thr
            325                 330                 335

Ser Tyr Gly Gln Asn Glu Asn Thr Ile Ser Ala Lys Leu Ala Asn Gln
            340                 345                 350

Leu Cys Asn Ala Tyr Ala Gln Leu Gly Ala Arg Gly Thr Ser Ile Leu
            355                 360                 365

Phe Ala Ser Gly Asp Gly Gly Val Ser Gly Ser Gln Ser Ala His Cys
            370                 375                 380

Ser Asn Phe Val Pro Thr Phe Pro Ser Gly Cys Pro Phe Met Thr Ser
385                 390                 395                 400

Val Gly Ala Thr Gln Gly Val Ser Pro Glu Thr Ala Ala Phe Ser
            405                 410                 415

Ser Gly Gly Phe Ser Asn Val Phe Gly Ile Pro Ser Tyr Gln Ala Ser
            420                 425                 430

Ala Val Ser Gly Tyr Leu Ser Ala Leu Gly Ser Thr Asn Ser Gly Lys
            435                 440                 445

Phe Asn Arg Ser Gly Arg Gly Phe Pro Asp Val Ser Thr Gln Gly Val
            450                 455                 460

Asp Phe Gln Ile Val Ser Gly Gly Gln Thr Ile Gly Val Asp Gly Thr
465                 470                 475                 480

Ser Cys Ala Ser Pro Thr Phe Ala Ser Val Ile Ser Leu Val Asn Asp
            485                 490                 495

Arg Leu Ile Ala Ala Gly Lys Ser Pro Leu Gly Phe Leu Asn Pro Phe
            500                 505                 510

Leu Tyr Ser Ser Ala Gly Lys Ala Ala Leu Asn Asp Val Thr Ser Gly
            515                 520                 525

Ser Asn Pro Gly Cys Ser Thr Asn Gly Phe Pro Ala Lys Ala Gly Trp
            530                 535                 540

Asp Pro Val Thr Gly Leu Gly Thr Pro Asn Phe Ala Lys Leu Leu Thr
545                 550                 555                 560

Ala Val Gly Leu

<210> SEQ ID NO 3
<211> LENGTH: 366
<212> TYPE: PRT
<213> ORGANISM: Meripilus giganteus

<400> SEQUENCE: 3

Ala Ile Pro Ala Ser Cys Ala Ser Thr Ile Thr Pro Ala Cys Leu Gln
1               5                   10                  15

Ala Ile Tyr Gly Ile Pro Thr Thr Lys Ala Thr Gln Ser Ser Asn Lys
            20                  25                  30

Leu Ala Val Ser Gly Phe Ile Asp Gln Phe Ala Asn Lys Ala Asp Leu
        35                  40                  45

Lys Ser Phe Leu Ala Gln Phe Arg Lys Asp Ile Ser Ser Thr Thr
50                  55                  60

Phe Ser Leu Gln Thr Leu Asp Gly Gly Glu Asn Asp Gln Ser Pro Ser
65                  70                  75                  80

Glu Ala Gly Ile Glu Ala Asn Leu Asp Ile Gln Tyr Thr Val Gly Leu
                85                  90                  95

Ala Thr Gly Val Pro Thr Thr Phe Ile Ser Val Gly Asp Asp Phe Gln
            100                 105                 110

Asp Gly Asn Leu Glu Gly Phe Leu Asp Ile Ile Asn Phe Leu Leu Gly
            115                 120                 125

Glu Ser Asn Pro Pro Gln Val Leu Thr Thr Ser Tyr Gly Gln Asn Glu
        130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ser Gly Ser Gln Ser Ala His Cys Ser Asn Phe Val Pro Thr
            180                 185                 190

Phe Pro Ser Gly Cys Pro Phe Met Thr Ser Val Gly Ala Thr Gln Gly
            195                 200                 205

Val Ser Pro Glu Thr Ala Ala Ala Phe Ser Ser Gly Gly Phe Ser Asn
210                 215                 220

Val Phe Gly Ile Pro Ser Tyr Gln Ala Ser Ala Val Ser Gly Tyr Leu
225                 230                 235                 240

Ser Ala Leu Gly Ser Thr Asn Ser Gly Lys Phe Asn Arg Ser Gly Arg
                245                 250                 255

Gly Phe Pro Asp Val Ser Thr Gln Gly Val Asp Phe Gln Ile Val Ser
            260                 265                 270

Gly Gly Gln Thr Ile Gly Val Asp Gly Thr Ser Cys Ala Ser Pro Thr
        275                 280                 285

Phe Ala Ser Val Ile Ser Leu Val Asn Asp Arg Leu Ile Ala Ala Gly
290                 295                 300

Lys Ser Pro Leu Gly Phe Leu Asn Pro Phe Leu Tyr Ser Ser Ala Gly
305                 310                 315                 320

Lys Ala Ala Leu Asn Asp Val Thr Ser Gly Ser Asn Pro Gly Cys Ser
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
        355                 360                 365

<210> SEQ ID NO 4
<211> LENGTH: 1698
<212> TYPE: DNA
<213> ORGANISM: Trametes versicolor

<400> SEQUENCE: 4
atggtcgcca ccagcttgct cgttgcctcc ctgttcacgc ttgtcctcgg caccccgacg      60
gctcgcaacc tcaagctgca tgagtctcgc gaggagatcc ccgccggctt ctcgctgagc     120
ggcgccgcct cgcccgacac gacgctgaag ctccgcctcg cgctcgttca gagcaacttc     180
gccgagcttg aggacaagct ctacgacgtc agcacccccgt cgagcgcgaa ctacggccag     240
cacctctcca aggaggaggt cgagcaactc gtcgctccca gtgccgcgtc tgtcgccgct     300

```
gtcaacgcct ggctcaccga gaacggtctc actgcgcaga ccatctcgcc ggccggcgat      360
tggttggcgt tcgaggtgcc cgtcagccag gccaacgagc tcttcgacgc cgacttctcc      420
gtgttcaccc acgacgaatc cggtctccag gctgtccgga ctctcgcgta ctccatcccc      480
gctgagctgc agggtcacct ggacctcgtc caccccacga tcacgttccc gaaccctaac      540
tcgcaccttc ccgtcgtgcg ctcgcccgtg aagcccattc agaacctcac ctcgcgcgcc      600
gtcccggctt cgtgcgctag caccatcacc cctgcgtgcc tgcaggcgct ctacggcatc      660
cccaccacca aggccaccca gtcctcgaac aagctcgctg tcagcggctt catcgaccag      720
ttcgccaact ccgccgactt gaagaccttc ctcggcaagt ccgcaccga catctcgtcg       780 tcgacgacct tcaccctcca gaccctcgac ggtggatcca acagccagtc cagcagccag      840
gctggtgttg aggctaactt ggacgtccag tacgctatcg gcatcgccac gggcgtccct      900
accaccttca tctccgtcgg tgacgacttc caggacggtg acctcgaggg cttcctcgac      960
atcatcaact tcctcctcaa cgaaagcgcg cccccgcagg tgctcacgac cagctacggc     1020
cagaacgaga acaccatctc cgccaagctt gccaaccaac tctgcaacgc atacgctcag     1080
ctcggcgcgc gtggcaccctc catcctcttc gcgtccggcg acggtggtgt tgccggctcg     1140
cagacctcca gctgcaccaa gttcctgccg accttcccct cgggctgccc cttcatgacc     1200
tccgtcggcg cgacgcaggg catcaacccg gagaccgccg ccgacttctc ctccggcggc     1260
ttctcaaacg tcttcgcccg ccctcgtac cagtctaccg ccgtcagcag ctacctgacc      1320
gcgctcggca gcaccaactc gggcaagttc aacacctccg ccgcgcgtt ccccgacatc      1380 gccacccagg gtgtcgactt cgagatcgtc gttggcggcc gcactgaggg cgtcgacggc     1440
actagctgcg ccagcccgac gcttgccgcg atcatctcgc tcctgaacga ccgcctcatc     1500
gcggccggca agagccccct tggcttcctc aaccccttcc tgtactcggc ggcgggcgcc     1560
gcggcactca ccgacatcac gtctggctcg aaccccggtt gcggcaccaa cggcttcccc     1620
gcgaaggctg gctgggaccc ggtcaccggt cttggcacgc ccaacttcgc caagctgctc     1680
actgctgttg gcctgtaa                                                   1698
```

<210> SEQ ID NO 5
<211> LENGTH: 565
<212> TYPE: PRT
<213> ORGANISM: Trametes versicolor

<400> SEQUENCE: 5

```
Met Val Ala Thr Ser Leu Leu Val Ala Ser Leu Phe Thr Leu Val Leu
1               5                   10                  15

Gly Thr Pro Thr Ala Arg Asn Leu Lys Leu His Glu Ser Arg Glu Glu
            20                  25                  30

Ile Pro Ala Gly Phe Ser Leu Ser Gly Ala Ala Ser Pro Asp Thr Thr
        35                  40                  45

Leu Lys Leu Arg Leu Ala Leu Val Gln Ser Asn Phe Ala Glu Leu Glu
    50                  55                  60

Asp Lys Leu Tyr Asp Val Ser Thr Pro Ser Ser Ala Asn Tyr Gly Gln
65                  70                  75                  80

His Leu Ser Lys Glu Glu Val Glu Gln Leu Val Ala Pro Ser Ala Ala
                85                  90                  95

Ser Val Ala Ala Val Asn Ala Trp Leu Thr Glu Asn Gly Leu Thr Ala
            100                 105                 110

Gln Thr Ile Ser Pro Ala Gly Asp Trp Leu Ala Phe Glu Val Pro Val
        115                 120                 125
```

```
Ser Gln Ala Asn Glu Leu Phe Asp Ala Asp Phe Ser Val Phe Thr His
    130                 135                 140
Asp Glu Ser Gly Leu Gln Ala Val Arg Thr Leu Ala Tyr Ser Ile Pro
145                 150                 155                 160
Ala Glu Leu Gln Gly His Leu Asp Leu Val His Pro Thr Ile Thr Phe
                    165                 170                 175
Pro Asn Pro Asn Ser His Leu Pro Val Val Arg Ser Pro Val Lys Pro
                180                 185                 190
Ile Gln Asn Leu Thr Ser Arg Ala Val Pro Ala Ser Cys Ala Ser Thr
    195                 200                 205
Ile Thr Pro Ala Cys Leu Gln Ala Leu Tyr Gly Ile Pro Thr Thr Lys
    210                 215                 220
Ala Thr Gln Ser Ser Asn Lys Leu Ala Val Ser Gly Phe Ile Asp Gln
225                 230                 235                 240
Phe Ala Asn Ser Ala Asp Leu Lys Thr Phe Leu Gly Lys Phe Arg Thr
                245                 250                 255
Asp Ile Ser Ser Ser Thr Thr Phe Thr Leu Gln Thr Leu Asp Gly Gly
                260                 265                 270
Ser Asn Ser Gln Ser Ser Ser Gln Ala Gly Val Glu Ala Asn Leu Asp
            275                 280                 285
Val Gln Tyr Ala Ile Gly Ile Ala Thr Gly Val Pro Thr Thr Phe Ile
    290                 295                 300
Ser Val Gly Asp Asp Phe Gln Asp Gly Asp Leu Glu Gly Phe Leu Asp
305                 310                 315                 320
Ile Ile Asn Phe Leu Leu Asn Glu Ser Ala Pro Pro Gln Val Leu Thr
                325                 330                 335
Thr Ser Tyr Gly Gln Asn Glu Asn Thr Ile Ser Ala Lys Leu Ala Asn
                340                 345                 350
Gln Leu Cys Asn Ala Tyr Ala Gln Leu Gly Ala Arg Gly Thr Ser Ile
            355                 360                 365
Leu Phe Ala Ser Gly Asp Gly Val Ala Gly Ser Gln Thr Ser Ser
    370                 375                 380
Cys Thr Lys Phe Leu Pro Thr Phe Pro Ser Gly Cys Pro Phe Met Thr
385                 390                 395                 400
Ser Val Gly Ala Thr Gln Gly Ile Asn Pro Glu Thr Ala Ala Asp Phe
                405                 410                 415
Ser Ser Gly Gly Phe Ser Asn Val Phe Ala Arg Pro Ser Tyr Gln Ser
                420                 425                 430
Thr Ala Val Ser Ser Tyr Leu Thr Ala Leu Gly Ser Thr Asn Ser Gly
            435                 440                 445
Lys Phe Asn Thr Ser Gly Arg Ala Phe Pro Asp Ile Ala Thr Gln Gly
    450                 455                 460
Val Asp Phe Glu Ile Val Val Gly Gly Arg Thr Glu Gly Val Asp Gly
465                 470                 475                 480
Thr Ser Cys Ala Ser Pro Thr Leu Ala Ala Ile Ile Ser Leu Leu Asn
                485                 490                 495
Asp Arg Leu Ile Ala Ala Gly Lys Ser Pro Leu Gly Phe Leu Asn Pro
                500                 505                 510
Phe Leu Tyr Ser Ala Ala Gly Ala Ala Ala Leu Thr Asp Ile Thr Ser
            515                 520                 525
Gly Ser Asn Pro Gly Cys Gly Thr Asn Gly Phe Pro Ala Lys Ala Gly
    530                 535                 540
```

Trp Asp Pro Val Thr Gly Leu Gly Thr Pro Asn Phe Ala Lys Leu Leu
545                 550                 555                 560

Thr Ala Val Gly Leu
                565

<210> SEQ ID NO 6
<211> LENGTH: 366
<212> TYPE: PRT
<213> ORGANISM: Trametes versicolor

<400> SEQUENCE: 6

Ala Val Pro Ala Ser Cys Ala Ser Thr Ile Thr Pro Ala Cys Leu Gln
1               5                   10                  15

Ala Leu Tyr Gly Ile Pro Thr Thr Lys Ala Thr Gln Ser Ser Asn Lys
            20                  25                  30

Leu Ala Val Ser Gly Phe Ile Asp Gln Phe Ala Asn Ser Ala Asp Leu
        35                  40                  45

Lys Thr Phe Leu Gly Lys Phe Arg Thr Asp Ile Ser Ser Ser Thr Thr
50                  55                  60

Phe Thr Leu Gln Thr Leu Asp Gly Gly Ser Asn Ser Gln Ser Ser
65                  70                  75                  80

Gln Ala Gly Val Glu Ala Asn Leu Asp Val Gln Tyr Ala Ile Gly Ile
                85                  90                  95

Ala Thr Gly Val Pro Thr Thr Phe Ile Ser Val Gly Asp Asp Phe Gln
            100                 105                 110

Asp Gly Asp Leu Glu Gly Phe Leu Asp Ile Ile Asn Phe Leu Leu Asn
        115                 120                 125

Glu Ser Ala Pro Pro Gln Val Leu Thr Thr Ser Tyr Gly Gln Asn Glu
130                 135                 140

Asn Thr Ile Ser Ala Lys Leu Ala Asn Gln Leu Cys Asn Ala Tyr Ala
145                 150                 155                 160

Gln Leu Gly Ala Arg Gly Thr Ser Ile Leu Phe Ala Ser Gly Asp Gly
                165                 170                 175

Gly Val Ala Gly Ser Gln Thr Ser Ser Cys Thr Lys Phe Leu Pro Thr
            180                 185                 190

Phe Pro Ser Gly Cys Pro Phe Met Thr Ser Val Gly Ala Thr Gln Gly
        195                 200                 205

Ile Asn Pro Glu Thr Ala Ala Asp Phe Ser Ser Gly Gly Phe Ser Asn
210                 215                 220

Val Phe Ala Arg Pro Ser Tyr Gln Ser Thr Ala Val Ser Ser Tyr Leu
225                 230                 235                 240

Thr Ala Leu Gly Ser Thr Asn Ser Gly Lys Phe Asn Thr Ser Gly Arg
                245                 250                 255

Ala Phe Pro Asp Ile Ala Thr Gln Gly Val Asp Phe Glu Ile Val Val
            260                 265                 270

Gly Gly Arg Thr Glu Gly Val Asp Gly Thr Ser Cys Ala Ser Pro Thr
        275                 280                 285

Leu Ala Ala Ile Ile Ser Leu Leu Asn Asp Arg Leu Ile Ala Ala Gly
290                 295                 300

Lys Ser Pro Leu Gly Phe Leu Asn Pro Phe Leu Tyr Ser Ala Ala Gly
305                 310                 315                 320

Ala Ala Ala Leu Thr Asp Ile Thr Ser Gly Ser Asn Pro Gly Cys Gly
                325                 330                 335

Thr Asn Gly Phe Pro Ala Lys Ala Gly Trp Asp Pro Val Thr Gly Leu
            340                 345                 350

Gly Thr Pro Asn Phe Ala Lys Leu Leu Thr Ala Val Gly Leu
    355                 360                 365

<210> SEQ ID NO 7
<211> LENGTH: 1704
<212> TYPE: DNA
<213> ORGANISM: Dichomitus squalens

<400> SEQUENCE: 7

```
atggttgcct ccggcttgtt cctcgcatcg ctcatcgctc tcgccttggg caagcccacc      60
gcccgcaacc tcaagctgca cgagtctcgc cccagcgccc cgaacggatt ctcgctcgta     120
ggctctgcgg actccaaccg gactctgaag ctgcgtcttg ctcttgccga gagcaacttc     180
tctgagcttg agcgcaagct gtatgatgtc agcacgccga agagtgctaa ctacggcaag     240
cacctctcca aggcggaggt acagcagctt gttgctcctg ggcaggacag catcgacgct     300
gtcaatgctt ggctgaagga gaacgacatc actgcgaaga cgatctcctc tactggcgag     360
tggatctcct tcgaggttcc tgtcagcaag gcgaacgatc tcttcgacgc cgacttctct     420
gtcttcaagc acgatgacac cggcgtggag gcgatccgca cccttcgta ctctattccg      480
gcagagcttc agggccacct cgatctcgtc caccctacgg tgacattccc taatccgtac     540
agccacctcc cggtcttcca gtcgcccgtc aagaagacgg ctgaaatcca gaacttcacc     600
gccggtgcta tccctcgtc gtgttcgagc acgatcactc ctgcttgtct tcaggccatc      660
tacaacatcc taccacagc tgcgaccgag tcgtcaaacc agctgggtgt gactggcttt      720
atcgaccagt acgccaacaa gaaagacctc aagactttct tgaagaagta ccgcaccgac     780
atctcttcga gcaccacctt caccctgcag accctcgatg gcggttccaa ctcgcagacg     840
ggtagcaagg ccggtgtcga ggctaacctc gacattcagt acactgtcgg cgttgccact     900
ggtgtcccga ctacctttat ctccgttgga gatgacttcc aggacggtga cctcgagggc     960
ttcctcgatg tcatcaacgc cctcctcgat gaggacgctc ctccttcggt cttgacgact    1020
tcatatggcc aggacgagag taccatctct cgtgccctcg cagttaaact ctgtaacgcg    1080
tatgctcagc ttggtgctcg tggtgttcct atcctcttcg cctcgggtga cggtggtgtc    1140
tccggctcgc agtctgccag ctgctccaaa tttgttccta ccttcccatc cggctgcccc    1200
tacatgacct ccgtcggcgc caccagggt gtaaacccg agaccgcggc tgacttctcc     1260
tccggcggct tctccaacta ctggggcgtc ccggactacc agagcgacgc tgtcagcacc    1320
tacctctccg cgctcggcaa gacgaactcc ggcaagtaca acgcctccgg ccgtggtttc    1380
cctgatgtgt ctacccaagg tgtgagcttc gaggtcgtcg tcgatggctc cgtagaggcg    1440
gtcgacggta cctcctgcgc gtcccccacg ttcgcgtcca tcatttccct cgtcaacgac    1500
aagctcgtcg cggcaggcaa gagtccgctc ggcttcctca acccttcct atactctgac     1560
ggcgtcgccg ccctcaacga catcacgtca ggctccaacc ctggctgcaa caccaacggc    1620
ttccctgcga agaagggttg ggaccctgtt actggtcttg gtaccctga cttcaagaag     1680
ctcctcaccg cagtcggcct gtga                                           1704
```

<210> SEQ ID NO 8
<211> LENGTH: 567
<212> TYPE: PRT
<213> ORGANISM: Dichomitus squalens

<400> SEQUENCE: 8

Met Val Ala Ser Gly Leu Phe Leu Ala Ser Leu Ile Ala Leu Ala Leu

```
1               5                   10                  15
Gly Lys Pro Thr Ala Arg Asn Leu Lys Leu His Glu Ser Arg Pro Ser
                20                  25                  30

Ala Pro Asn Gly Phe Ser Leu Val Gly Ser Ala Asp Ser Asn Arg Thr
                35                  40                  45

Leu Lys Leu Arg Leu Ala Leu Ala Glu Ser Asn Phe Ser Glu Leu Glu
    50                  55                  60

Arg Lys Leu Tyr Asp Val Ser Thr Pro Lys Ser Ala Asn Tyr Gly Lys
65                  70                  75                  80

His Leu Ser Lys Ala Glu Val Gln Gln Leu Val Ala Pro Gly Gln Asp
                85                  90                  95

Ser Ile Asp Ala Val Asn Ala Trp Leu Lys Glu Asn Asp Ile Thr Ala
                100                 105                 110

Lys Thr Ile Ser Ser Thr Gly Glu Trp Ile Ser Phe Glu Val Pro Val
                115                 120                 125

Ser Lys Ala Asn Asp Leu Phe Asp Ala Asp Phe Ser Val Phe Lys His
                130                 135                 140

Asp Asp Thr Gly Val Glu Ala Ile Arg Thr Leu Ser Tyr Ser Ile Pro
145                 150                 155                 160

Ala Glu Leu Gln Gly His Leu Asp Leu Val His Pro Thr Val Thr Phe
                165                 170                 175

Pro Asn Pro Tyr Ser His Leu Pro Val Phe Gln Ser Pro Val Lys Lys
                180                 185                 190

Thr Ala Glu Ile Gln Asn Phe Thr Ala Gly Ala Ile Pro Ser Ser Cys
                195                 200                 205

Ser Ser Thr Ile Thr Pro Ala Cys Leu Gln Ala Ile Tyr Asn Ile Pro
210                 215                 220

Thr Thr Ala Ala Thr Glu Ser Ser Asn Gln Leu Gly Val Thr Gly Phe
225                 230                 235                 240

Ile Asp Gln Tyr Ala Asn Lys Lys Asp Leu Lys Thr Phe Leu Lys Lys
                245                 250                 255

Tyr Arg Thr Asp Ile Ser Ser Ser Thr Thr Phe Thr Leu Gln Thr Leu
                260                 265                 270

Asp Gly Gly Ser Asn Ser Gln Thr Gly Ser Lys Ala Gly Val Glu Ala
                275                 280                 285

Asn Leu Asp Ile Gln Tyr Thr Val Gly Val Ala Thr Gly Val Pro Thr
                290                 295                 300

Thr Phe Ile Ser Val Gly Asp Asp Phe Gln Asp Gly Asp Leu Glu Gly
305                 310                 315                 320

Phe Leu Asp Val Ile Asn Ala Leu Leu Asp Glu Asp Ala Pro Pro Ser
                325                 330                 335

Val Leu Thr Thr Ser Tyr Gly Gln Asp Glu Ser Thr Ile Ser Arg Ala
                340                 345                 350

Leu Ala Val Lys Leu Cys Asn Ala Tyr Ala Gln Leu Gly Ala Arg Gly
                355                 360                 365

Val Ser Ile Leu Phe Ala Ser Gly Asp Gly Gly Val Ser Gly Ser Gln
                370                 375                 380

Ser Ala Ser Cys Ser Lys Phe Val Pro Thr Phe Pro Ser Gly Cys Pro
385                 390                 395                 400

Tyr Met Thr Ser Val Gly Ala Thr Gln Gly Val Asn Pro Glu Thr Ala
                405                 410                 415

Ala Asp Phe Ser Ser Gly Gly Phe Ser Asn Tyr Trp Gly Val Pro Asp
                420                 425                 430
```

```
Tyr Gln Ser Asp Ala Val Ser Thr Tyr Leu Ser Ala Leu Gly Lys Thr
            435                 440                 445

Asn Ser Gly Lys Tyr Asn Ala Ser Gly Arg Gly Phe Pro Asp Val Ser
        450                 455                 460

Thr Gln Gly Val Ser Phe Glu Val Val Asp Gly Ser Val Glu Ala
465                 470                 475                 480

Val Asp Gly Thr Ser Cys Ala Ser Pro Thr Phe Ala Ser Ile Ile Ser
                485                 490                 495

Leu Val Asn Asp Lys Leu Val Ala Ala Gly Lys Ser Pro Leu Gly Phe
                500                 505                 510

Leu Asn Pro Phe Leu Tyr Ser Asp Gly Val Ala Ala Leu Asn Asp Ile
                515                 520                 525

Thr Ser Gly Ser Asn Pro Gly Cys Asn Thr Asn Gly Phe Pro Ala Lys
                530                 535                 540

Lys Gly Trp Asp Pro Val Thr Gly Leu Gly Thr Pro Asp Phe Lys Lys
545                 550                 555                 560

Leu Leu Thr Ala Val Gly Leu
                565

<210> SEQ ID NO 9
<211> LENGTH: 365
<212> TYPE: PRT
<213> ORGANISM: Dichomitus squalens

<400> SEQUENCE: 9

Ala Ile Pro Ser Ser Cys Ser Ser Thr Ile Thr Pro Ala Cys Leu Gln
1               5                   10                  15

Ala Ile Tyr Asn Ile Pro Thr Thr Ala Ala Thr Glu Ser Ser Asn Gln
                20                  25                  30

Leu Gly Val Thr Gly Phe Ile Asp Gln Tyr Ala Asn Lys Lys Asp Leu
            35                  40                  45

Lys Thr Phe Leu Lys Lys Tyr Arg Thr Asp Ile Ser Ser Ser Thr Thr
 50                 55                  60

Phe Thr Leu Gln Thr Leu Asp Gly Gly Ser Asn Ser Gln Thr Gly Ser
 65                 70                  75                  80

Lys Ala Gly Val Glu Ala Asn Leu Asp Ile Gln Tyr Thr Val Gly Val
                85                  90                  95

Ala Thr Gly Val Pro Thr Thr Phe Ile Ser Val Gly Asp Asp Phe Gln
                100                 105                 110

Asp Gly Asp Leu Glu Gly Phe Leu Asp Val Ile Asn Ala Leu Leu Asp
            115                 120                 125

Glu Asp Ala Pro Pro Ser Val Leu Thr Thr Ser Tyr Gly Gln Asp Glu
            130                 135                 140

Ser Thr Ile Ser Arg Ala Leu Ala Val Lys Leu Cys Asn Ala Tyr Ala
145                 150                 155                 160

Gln Leu Gly Ala Arg Gly Val Ser Ile Leu Phe Ala Ser Gly Asp Gly
                165                 170                 175

Gly Val Ser Gly Ser Gln Ser Ala Ser Cys Ser Lys Phe Val Pro Thr
                180                 185                 190

Phe Pro Ser Gly Cys Pro Tyr Met Thr Ser Val Gly Ala Thr Gln Gly
                195                 200                 205

Val Asn Pro Glu Thr Ala Ala Asp Phe Ser Ser Gly Gly Phe Ser Asn
            210                 215                 220

Tyr Trp Gly Val Pro Asp Tyr Gln Ser Asp Ala Val Ser Thr Tyr Leu
```

```
                225                 230                 235                 240
Ser Ala Leu Gly Lys Thr Asn Ser Gly Lys Tyr Asn Ala Ser Gly Arg
                    245                 250                 255

Gly Phe Pro Asp Val Ser Thr Gln Gly Val Ser Phe Glu Val Val
                260                 265                 270

Asp Gly Ser Val Glu Ala Val Asp Gly Thr Ser Cys Ala Ser Pro Thr
                275                 280                 285

Phe Ala Ser Ile Ile Ser Leu Val Asn Asp Lys Leu Val Ala Ala Gly
                290                 295                 300

Lys Ser Pro Leu Gly Phe Leu Asn Pro Phe Leu Tyr Ser Asp Gly Val
305                 310                 315                 320

Ala Ala Leu Asn Asp Ile Thr Ser Gly Ser Asn Pro Gly Cys Asn Thr
                    325                 330                 335

Asn Gly Phe Pro Ala Lys Lys Gly Trp Asp Pro Val Thr Gly Leu Gly
                340                 345                 350

Thr Pro Asp Phe Lys Lys Leu Leu Thr Ala Val Gly Leu
                355                 360                 365

<210> SEQ ID NO 10
<211> LENGTH: 1704
<212> TYPE: DNA
<213> ORGANISM: Polyporus arcularius

<400> SEQUENCE: 10
atggttgcca cccgcgggtt gttcttcgtc tcgctctttg ccctcgcctt gggaaagccc      60
atggcgcgca gcatgaagct gcatgagtcc cgcgagggca ttcccgaagg cttctcgctg     120
cgcggtgctg ctcagccgga gcagaccatc aagcttcgtc ttgcactcgt gcagagcaac     180
ttcgccgagc tcgagcgcaa gctgatggac gtcagcacgc cgtcgagcgc gaactacggg     240
aagcacctat cgaaggcaga ggtccagcaa ctcgttgccc ccactcagga cagcgtcgac     300
gccgtcaagt cttggttgaa ggagaacgac atcagtgcga agacgatctc cgccaccggt     360
gattggctct cgttcgaggt ccccgtcagc aaggcgaacg agctattcga tgccgacttc     420
tccatctaca cgcacgacga gaccggcacg gaagccgtcc gcaccctctc ctactctatc     480
ccggccgaac tccagggaca ccttgacctc gtgcacccga cggtcacttt cccaaacccc     540
agaggccttc ctccggtctt cactgcgccc atcaaggctg aggctcagaa cctgacgtcg     600
cgcgcgacga tcccctcgtc gtgcgcacgc accatcacac ccgcgtgcct gcaggcgatc     660
tacaacatac cttcgacgcc ggccaccgag tcgtcgaaca agctcgctgt caccggcttc     720
atcgagcagt cgccaacaa ggccgacctc aaaaccttct tgacccggtt ccgcacagac     780
atctcgtcct cgacgagctt tactcttcag acgctcgatg gcggctcgaa cccacaaagc     840
agcagcgagg ctggcgtcga ggctaacctt gacatccagt acaccgtcgg tgttgccacc     900
ggcgttccca ccgtgttcat ctccgttggc gaagacttcc aggacggtga cctcgagggg     960
ttcctcgatg tcgtcaactc cctcctcgac gaggacacgc ccccttccgt catgaccacg    1020
agctacggcc agaacgaaaa cacgatctct cgcaacctcg ccaacaactt gtgcaatgcg    1080
tacgcgcagc ttggggcccg gggtgtctcc atcctgttcg cctctggtga cggtggcgtc    1140
gctggctctc agtccgccag ctgcagcaag ttcgttccga cgttcccctc tggctgccct    1200
ttcatgactt ccgtcggggc cacccaaggc ttcagcccg agactgctgc cgacttctcg    1260
tccggcggct tctccaacta ctttgccatc ccgactacc agaccagtgc cgtccgggc    1320
tacatcaagg ccctcggtaa caccaactct ggcaagtaca cgcgaccgg ccgcggcttc    1380
```

```
cccgacatcg ccacgcaggg cgtcaacttc gaagttgtcg tcggtggcca atctggcacc    1440
gtcgagggga cgagctgctc gagtccgacg cttgccagca tcatctccct cttgaacgac    1500
cgcctcatcg ctgctgggaa gagccccctc gggttcctga acccttcct gtactcgact     1560 gggacgtcgg ccctcaacga catcacctct ggctcgaatc ccggctgcaa cacgaacggg    1620
ttcccggcga aggctggctg ggatcctgtc actggtctcg gtacgcccga cttcaacaag    1680
ctgctctcgg ctgtcggctt gtaa                                           1704
```

<210> SEQ ID NO 11
<211> LENGTH: 567
<212> TYPE: PRT
<213> ORGANISM: Polyporus arcularius

<400> SEQUENCE: 11

```
Met Val Ala Thr Arg Gly Leu Phe Phe Val Ser Leu Phe Ala Leu Ala
1               5                   10                  15

Leu Gly Lys Pro Met Ala Arg Ser Met Lys Leu His Glu Ser Arg Glu
            20                  25                  30

Gly Ile Pro Glu Gly Phe Ser Leu Arg Gly Ala Ala Gln Pro Glu Gln
        35                  40                  45

Thr Ile Lys Leu Arg Leu Ala Leu Val Gln Ser Asn Phe Ala Glu Leu
    50                  55                  60

Glu Arg Lys Leu Met Asp Val Ser Thr Pro Ser Ser Ala Asn Tyr Gly
65                  70                  75                  80

Lys His Leu Ser Lys Ala Glu Val Gln Gln Leu Val Ala Pro Thr Gln
                85                  90                  95

Asp Ser Val Asp Ala Val Lys Ser Trp Leu Lys Glu Asn Asp Ile Ser
            100                 105                 110

Ala Lys Thr Ile Ser Ala Thr Gly Asp Trp Leu Ser Phe Glu Val Pro
        115                 120                 125

Val Ser Lys Ala Asn Glu Leu Phe Asp Ala Asp Phe Ser Ile Tyr Thr
    130                 135                 140

His Asp Glu Thr Gly Thr Glu Ala Val Arg Thr Leu Ser Tyr Ser Ile
145                 150                 155                 160

Pro Ala Glu Leu Gln Gly His Leu Asp Leu Val His Pro Thr Val Thr
                165                 170                 175

Phe Pro Asn Pro Arg Gly Leu Pro Pro Val Phe Thr Ala Pro Ile Lys
            180                 185                 190

Ala Glu Ala Gln Asn Leu Thr Ser Arg Ala Thr Ile Pro Ser Ser Cys
        195                 200                 205

Ala Arg Thr Ile Thr Pro Ala Cys Leu Gln Ala Ile Tyr Asn Ile Pro
    210                 215                 220

Ser Thr Pro Ala Thr Glu Ser Ser Asn Lys Leu Ala Val Thr Gly Phe
225                 230                 235                 240

Ile Glu Gln Phe Ala Asn Lys Ala Asp Leu Lys Thr Phe Leu Thr Arg
                245                 250                 255

Phe Arg Thr Asp Ile Ser Ser Ser Thr Ser Phe Thr Leu Gln Thr Leu
            260                 265                 270

Asp Gly Gly Ser Asn Pro Gln Ser Ser Glu Ala Gly Val Glu Ala
        275                 280                 285

Asn Leu Asp Ile Gln Tyr Thr Val Gly Val Ala Thr Gly Val Pro Thr
    290                 295                 300

Val Phe Ile Ser Val Gly Glu Asp Phe Gln Asp Gly Asp Leu Glu Gly
```

```
                305                 310                 315                 320
        Phe Leu Asp Val Val Asn Ser Leu Leu Asp Glu Asp Thr Pro Pro Phe
                        325                 330                 335

Val Met Thr Thr Ser Tyr Gly Gln Asn Glu Asn Thr Ile Ser Arg Asn
                        340                 345                 350

Leu Ala Asn Asn Leu Cys Asn Ala Tyr Ala Gln Leu Gly Ala Arg Gly
                        355                 360                 365

Val Ser Ile Leu Phe Ala Ser Gly Asp Gly Val Ala Gly Ser Gln
                        370                 375                 380

Ser Ala Ser Cys Ser Lys Phe Val Pro Thr Phe Pro Ser Gly Cys Pro
        385                 390                 395                 400

Phe Met Thr Ser Val Gly Ala Thr Gln Gly Phe Ser Pro Glu Thr Ala
                        405                 410                 415

Ala Asp Phe Ser Ser Gly Gly Phe Ser Asn Tyr Phe Ala Ile Pro Asp
                        420                 425                 430

Tyr Gln Thr Ser Ala Val Ser Gly Tyr Ile Lys Ala Leu Gly Asn Thr
                        435                 440                 445

Asn Ser Gly Lys Tyr Asn Ala Thr Gly Arg Gly Phe Pro Asp Ile Ala
                        450                 455                 460

Thr Gln Gly Val Asn Phe Glu Val Val Gly Gly Gln Ser Gly Thr
        465                 470                 475                 480

Val Glu Gly Thr Ser Cys Ser Ser Pro Thr Leu Ala Ser Ile Ile Ser
                        485                 490                 495

Leu Leu Asn Asp Arg Leu Ile Ala Ala Gly Lys Ser Pro Leu Gly Phe
                        500                 505                 510

Leu Asn Pro Phe Leu Tyr Ser Thr Gly Thr Ser Ala Leu Asn Asp Ile
                        515                 520                 525

Thr Ser Gly Ser Asn Pro Gly Cys Asn Thr Asn Gly Phe Pro Ala Lys
                        530                 535                 540

Ala Gly Trp Asp Pro Val Thr Gly Leu Gly Thr Pro Asp Phe Asn Lys
        545                 550                 555                 560

Leu Leu Ser Ala Val Gly Leu
                        565

<210> SEQ ID NO 12
<211> LENGTH: 366
<212> TYPE: PRT
<213> ORGANISM: Polyporus arcularius

<400> SEQUENCE: 12

Ala Thr Ile Pro Ser Ser Cys Ala Arg Thr Ile Thr Pro Ala Cys Leu
        1               5                   10                  15

Gln Ala Ile Tyr Asn Ile Pro Ser Thr Pro Ala Thr Glu Ser Ser Asn
                        20                  25                  30

Lys Leu Ala Val Thr Gly Phe Ile Glu Gln Phe Ala Asn Lys Ala Asp
                        35                  40                  45

Leu Lys Thr Phe Leu Thr Arg Phe Arg Thr Asp Ile Ser Ser Ser Thr
                        50                  55                  60

Ser Phe Thr Leu Gln Thr Leu Asp Gly Gly Ser Asn Pro Gln Ser Ser
        65                  70                  75                  80

Ser Glu Ala Gly Val Glu Ala Asn Leu Asp Ile Gln Tyr Thr Val Gly
                        85                  90                  95

Val Ala Thr Gly Val Pro Thr Val Phe Ile Ser Val Gly Glu Asp Phe
                        100                 105                 110
```

```
Gln Asp Gly Asp Leu Glu Gly Phe Leu Asp Val Val Asn Ser Leu Leu
            115                 120                 125

Asp Glu Asp Thr Pro Pro Phe Val Met Thr Thr Ser Tyr Gly Gln Asn
        130                 135                 140

Glu Asn Thr Ile Ser Arg Asn Leu Ala Asn Asn Leu Cys Asn Ala Tyr
145                 150                 155                 160

Ala Gln Leu Gly Ala Arg Gly Val Ser Ile Leu Phe Ala Ser Gly Asp
                165                 170                 175

Gly Gly Val Ala Gly Ser Gln Ser Ala Ser Cys Ser Lys Phe Val Pro
            180                 185                 190

Thr Phe Pro Ser Gly Cys Pro Phe Met Thr Ser Val Gly Ala Thr Gln
        195                 200                 205

Gly Phe Ser Pro Glu Thr Ala Ala Asp Phe Ser Ser Gly Gly Phe Ser
    210                 215                 220

Asn Tyr Phe Ala Ile Pro Asp Tyr Gln Thr Ser Ala Val Ser Gly Tyr
225                 230                 235                 240

Ile Lys Ala Leu Gly Asn Thr Asn Ser Gly Lys Tyr Asn Ala Thr Gly
                245                 250                 255

Arg Gly Phe Pro Asp Ile Ala Thr Gln Gly Val Asn Phe Glu Val Val
            260                 265                 270

Val Gly Gly Gln Ser Gly Thr Val Glu Gly Thr Ser Cys Ser Ser Pro
        275                 280                 285

Thr Leu Ala Ser Ile Ile Ser Leu Leu Asn Asp Arg Leu Ile Ala Ala
    290                 295                 300

Gly Lys Ser Pro Leu Gly Phe Leu Asn Pro Phe Leu Tyr Ser Thr Gly
305                 310                 315                 320

Thr Ser Ala Leu Asn Asp Ile Thr Ser Gly Ser Asn Pro Gly Cys Asn
                325                 330                 335

Thr Asn Gly Phe Pro Ala Lys Ala Gly Trp Asp Pro Val Thr Gly Leu
            340                 345                 350

Gly Thr Pro Asp Phe Asn Lys Leu Leu Ser Ala Val Gly Leu
        355                 360                 365

<210> SEQ ID NO 13
<211> LENGTH: 1698
<212> TYPE: DNA
<213> ORGANISM: Lenzites betulinus

<400> SEQUENCE: 13
atggtcgcca ccagcttgtt tgtcgccgct ctcatcacgc tcgccgtcgg caagccgatg       60
ggccgcaacc tcaaggtgca cgaggcccgc gaggagatcc agacgggtt ctctctgcaa      120 ggctcggcgg cgcccgacac cacgctcaag ctgcgcatcg cgctggtgca gagcaacttc      180
gccgagctcg aacagaagct ctacgacgtc agcacccgt ccagcccaa ctacggtgct       240 cacctctcaa aggaggaggt cgagcagctc gtcgctccct ccgcggacag cgtagacgcc      300
gtgaatgcgt ggctcaagga gaacgatctc agcgcgcaga ctatttcccc cgccggagac      360
tggctggcgt tcgaggtccc cgtcagcaag gcgaacgagc tcttcgacgc cgacttctct      420
gttttcaccc cgatcagac cggcctggag gctatccgca ccatgtcgta ctcgatcccg      480
gccgagctcc agggccacct tgacctcgtc catcccaccg tcactttccc taacccgtac      540
tcccacctgc cggttgttcg ctctcccatc aaggcctccc agaacctgac ctcacgtgcc      600
acgatcccgc cttcctgcgc cagcaccatc actcccgcat gctgcaggag catttacggc      660
atccctacga ctaaggccac ccagtcttcc aacaagcttg ccgtcagcgg cttcatcgac      720
```

```
cagtttgcta actcggctga cttggcgacc ttcttgaaga agttccgtac cgacatctcg    780
tctaccacga ccttcgccct ccagaccctc gatggcggtt cgaacagcca gagcggcagc    840
caggccggtg ttgaggctaa cctcgacatt caatacactg tcggtctcgc ctcaggcgtc    900
cccgtcacgt tcatctccgt tggtgacaac ttccaggatg tgacctcga gggcttcctt     960
gacatcatca acttcctcct cgccgagagc gcgccccctc aggtgcttac gaccagctac   1020
ggccagaacg agaacaccat ctccgtcaag ctcgccaacc aactctgcaa cgcatacgct   1080
cagctcggtg ctcgtggcac ctccatcctg ttcgcctccg gtgacggcgg tgtgtccggt   1140
tcgcagtcct ccagctgctc caaattcgtc ccgactttcc cctctggctg ccccttcatg   1200
acctccgtcg gtgccaccca gggcgtcaac ccgagaccg cggccgactt ctcctccggc    1260
ggcttctcga actacttcgg catcccgtcg taccaggcca ccgcggtgaa gacctacctg   1320
accgcgctcg caccaccaa ctcgggcaag ttcaacacca gcggccgcgc gttccctgac    1380
gtgtccaccc agggtgtcga cttcgagatc gtcgttgacg gccggaccga gggcgtcgac   1440
ggcacctcgt gcgcgagccc cacgttcgcg gccatcatct cgctcgtcaa cgacaagctc   1500
atcgctgctg caagagccc gctcggcttc ctcaacccct tcctgtactc gaccggcgcc    1560
agcgcgttca ccgacatcac ctccggctcg aaccctggct gcaacaccaa aggcttcccc   1620
gcgaaggctg gctgggaccc cgtcactggt ctcggcacgc ccaacttcgc caagctcctc   1680
gcggccgcgg gcgtgtaa                                                 1698
```

<210> SEQ ID NO 14
<211> LENGTH: 565
<212> TYPE: PRT
<213> ORGANISM: Lenzites betulinus

<400> SEQUENCE: 14

```
Met Val Ala Thr Ser Leu Phe Val Ala Ala Leu Ile Thr Leu Ala Val
1               5                   10                  15

Gly Lys Pro Met Gly Arg Asn Leu Lys Val His Glu Ala Arg Glu Glu
            20                  25                  30

Ile Pro Asp Gly Phe Ser Leu Gln Gly Ser Ala Ala Pro Asp Thr Thr
        35                  40                  45

Leu Lys Leu Arg Ile Ala Leu Val Gln Ser Asn Phe Ala Glu Leu Glu
    50                  55                  60

Gln Lys Leu Tyr Asp Val Ser Thr Pro Ser Pro Asn Tyr Gly Ala
65                  70                  75                  80

His Leu Ser Lys Glu Glu Val Glu Gln Leu Val Ala Pro Ser Ala Asp
                85                  90                  95

Ser Val Asp Ala Val Asn Ala Trp Leu Lys Glu Asn Asp Leu Ser Ala
            100                 105                 110

Gln Thr Ile Ser Pro Ala Gly Asp Trp Leu Ala Phe Glu Val Pro Val
        115                 120                 125

Ser Lys Ala Asn Glu Leu Phe Asp Ala Asp Phe Ser Val Phe Thr His
    130                 135                 140

Asp Gln Thr Gly Leu Glu Ala Ile Arg Thr Met Ser Tyr Ser Ile Pro
145                 150                 155                 160

Ala Glu Leu Gln Gly His Leu Asp Leu Val His Pro Thr Val Thr Phe
                165                 170                 175

Pro Asn Pro Tyr Ser His Leu Pro Val Val Arg Ser Pro Ile Lys Ala
            180                 185                 190
```

-continued

Ser Gln Asn Leu Thr Ser Arg Ala Thr Ile Pro Ala Ser Cys Ala Ser
            195                 200                 205

Thr Ile Thr Pro Ala Cys Leu Gln Asp Ile Tyr Gly Ile Pro Thr Thr
210                 215                 220

Lys Ala Thr Gln Ser Ser Asn Lys Leu Ala Val Ser Gly Phe Ile Asp
225                 230                 235                 240

Gln Phe Ala Asn Ser Ala Asp Leu Ala Thr Phe Leu Lys Lys Phe Arg
                245                 250                 255

Thr Asp Ile Ser Ser Thr Thr Phe Ala Leu Gln Thr Leu Asp Gly
            260                 265                 270

Gly Ser Asn Ser Gln Ser Gly Ser Gln Ala Gly Val Glu Ala Asn Leu
            275                 280                 285

Asp Ile Gln Tyr Thr Val Gly Leu Ala Ser Gly Val Pro Val Thr Phe
290                 295                 300

Ile Ser Val Gly Asp Asn Phe Gln Asp Gly Asp Leu Glu Gly Phe Leu
305                 310                 315                 320

Asp Ile Ile Asn Phe Leu Leu Ala Glu Ser Ala Pro Pro Gln Val Leu
                325                 330                 335

Thr Thr Ser Tyr Gly Gln Asn Glu Asn Thr Ile Ser Val Lys Leu Ala
            340                 345                 350

Asn Gln Leu Cys Asn Ala Tyr Ala Gln Leu Gly Ala Arg Gly Thr Ser
            355                 360                 365

Ile Leu Phe Ala Ser Gly Asp Gly Val Ser Gly Ser Gln Ser Ser
            370                 375                 380

Ser Cys Ser Lys Phe Val Pro Thr Phe Pro Ser Gly Cys Pro Phe Met
385                 390                 395                 400

Thr Ser Val Gly Ala Thr Gln Gly Val Asn Pro Glu Thr Ala Ala Asp
                405                 410                 415

Phe Ser Ser Gly Gly Phe Ser Asn Tyr Phe Gly Ile Pro Ser Tyr Gln
                420                 425                 430

Ala Thr Ala Val Lys Thr Tyr Leu Thr Ala Leu Gly Thr Thr Asn Ser
            435                 440                 445

Gly Lys Phe Asn Thr Ser Gly Arg Ala Phe Pro Asp Val Ser Thr Gln
450                 455                 460

Gly Val Asp Phe Glu Ile Val Val Asp Gly Arg Thr Glu Gly Val Asp
465                 470                 475                 480

Gly Thr Ser Cys Ala Ser Pro Thr Phe Ala Ala Ile Ile Ser Leu Val
                485                 490                 495

Asn Asp Lys Leu Ile Ala Ala Gly Lys Ser Pro Leu Gly Phe Leu Asn
            500                 505                 510

Pro Phe Leu Tyr Ser Thr Gly Ala Ser Ala Phe Thr Asp Ile Thr Ser
            515                 520                 525

Gly Ser Asn Pro Gly Cys Asn Thr Lys Gly Phe Pro Ala Lys Ala Gly
            530                 535                 540

Trp Asp Pro Val Thr Gly Leu Gly Thr Pro Asn Phe Ala Lys Leu Leu
545                 550                 555                 560

Ala Ala Ala Gly Val
            565

<210> SEQ ID NO 15
<211> LENGTH: 366
<212> TYPE: PRT
<213> ORGANISM: Lenzites betulinus

<400> SEQUENCE: 15

```
Ala Thr Ile Pro Ala Ser Cys Ala Ser Thr Ile Thr Pro Ala Cys Leu
1               5                   10                  15

Gln Asp Ile Tyr Gly Ile Pro Thr Thr Lys Ala Thr Gln Ser Ser Asn
            20                  25                  30

Lys Leu Ala Val Ser Gly Phe Ile Asp Gln Phe Ala Asn Ser Ala Asp
        35                  40                  45

Leu Ala Thr Phe Leu Lys Lys Phe Arg Thr Asp Ile Ser Ser Thr Thr
    50                  55                  60

Thr Phe Ala Leu Gln Thr Leu Asp Gly Gly Ser Asn Ser Gln Ser Gly
65                  70                  75                  80

Ser Gln Ala Gly Val Glu Ala Asn Leu Asp Ile Gln Tyr Thr Val Gly
                85                  90                  95

Leu Ala Ser Gly Val Pro Val Thr Phe Ile Ser Val Gly Asp Asn Phe
                100                 105                 110

Gln Asp Gly Asp Leu Glu Gly Phe Leu Asp Ile Ile Asn Phe Leu Leu
            115                 120                 125

Ala Glu Ser Ala Pro Pro Gln Val Leu Thr Thr Ser Tyr Gly Gln Asn
        130                 135                 140

Glu Asn Thr Ile Ser Val Lys Leu Ala Asn Gln Leu Cys Asn Ala Tyr
145                 150                 155                 160

Ala Gln Leu Gly Ala Arg Gly Thr Ser Ile Leu Phe Ala Ser Gly Asp
                165                 170                 175

Gly Gly Val Ser Gly Ser Gln Ser Ser Cys Ser Lys Phe Val Pro
                180                 185                 190

Thr Phe Pro Ser Gly Cys Pro Phe Met Thr Ser Val Gly Ala Thr Gln
            195                 200                 205

Gly Val Asn Pro Glu Thr Ala Ala Asp Phe Ser Ser Gly Gly Phe Ser
        210                 215                 220

Asn Tyr Phe Gly Ile Pro Ser Tyr Gln Ala Thr Ala Val Lys Thr Tyr
225                 230                 235                 240

Leu Thr Ala Leu Gly Thr Thr Asn Ser Gly Lys Phe Asn Thr Ser Gly
                245                 250                 255

Arg Ala Phe Pro Asp Val Ser Thr Gln Gly Val Asp Phe Glu Ile Val
            260                 265                 270

Val Asp Gly Arg Thr Glu Gly Val Asp Gly Thr Ser Cys Ala Ser Pro
        275                 280                 285

Thr Phe Ala Ala Ile Ile Ser Leu Val Asn Asp Lys Leu Ile Ala Ala
290                 295                 300

Gly Lys Ser Pro Leu Gly Phe Leu Asn Pro Phe Leu Tyr Ser Thr Gly
305                 310                 315                 320

Ala Ser Ala Phe Thr Asp Ile Thr Ser Gly Ser Asn Pro Gly Cys Asn
                325                 330                 335

Thr Lys Gly Phe Pro Ala Lys Ala Gly Trp Asp Pro Val Thr Gly Leu
            340                 345                 350

Gly Thr Pro Asn Phe Ala Lys Leu Leu Ala Ala Gly Val
        355                 360                 365

<210> SEQ ID NO 16
<211> LENGTH: 583
<212> TYPE: PRT
<213> ORGANISM: Rhizomucor pusillus

<400> SEQUENCE: 16

Ala Thr Ser Asp Asp Trp Lys Gly Lys Ala Ile Tyr Gln Leu Leu Thr
```

-continued

```
1               5                   10                  15
Asp Arg Phe Gly Arg Ala Asp Asp Ser Thr Ser Asn Cys Ser Asn Leu
                20                  25                  30
Ser Asn Tyr Cys Gly Gly Thr Tyr Glu Gly Ile Thr Lys His Leu Asp
                35                  40                  45
Tyr Ile Ser Gly Met Gly Phe Asp Ala Ile Trp Ile Ser Pro Ile Pro
 50                  55                  60
Lys Asn Ser Asp Gly Gly Tyr His Gly Tyr Trp Ala Thr Asp Phe Tyr
 65                  70                  75                  80
Gln Leu Asn Ser Asn Phe Gly Asp Glu Ser Gln Leu Lys Ala Leu Ile
                85                  90                  95
Gln Ala Ala His Glu Arg Asp Met Tyr Val Met Leu Asp Val Val Ala
                100                 105                 110
Asn His Ala Gly Pro Thr Ser Asn Gly Tyr Ser Gly Tyr Thr Phe Gly
                115                 120                 125
Asp Ala Ser Leu Tyr His Pro Lys Cys Thr Ile Asp Tyr Asn Asp Gln
                130                 135                 140
Thr Ser Ile Glu Gln Cys Trp Val Ala Asp Glu Leu Pro Asp Ile Asp
145                 150                 155                 160
Thr Glu Asn Ser Asp Asn Val Ala Ile Leu Asn Asp Ile Val Ser Gly
                165                 170                 175
Trp Val Gly Asn Tyr Ser Phe Asp Gly Ile Arg Ile Asp Thr Val Lys
                180                 185                 190
His Ile Arg Lys Asp Phe Trp Thr Gly Tyr Ala Glu Ala Ala Gly Val
                195                 200                 205
Phe Ala Thr Gly Glu Val Phe Asn Gly Asp Pro Ala Tyr Val Gly Pro
210                 215                 220
Tyr Gln Lys Tyr Leu Pro Ser Leu Ile Asn Tyr Pro Met Tyr Tyr Ala
225                 230                 235                 240
Leu Asn Asp Val Phe Val Ser Lys Ser Lys Gly Phe Ser Arg Ile Ser
                245                 250                 255
Glu Met Leu Gly Ser Asn Arg Asn Ala Phe Glu Asp Thr Ser Val Leu
                260                 265                 270
Thr Thr Phe Val Asp Asn His Asp Asn Pro Arg Phe Leu Asn Ser Gln
                275                 280                 285
Ser Asp Lys Ala Leu Phe Lys Asn Ala Leu Thr Tyr Val Leu Leu Gly
                290                 295                 300
Glu Gly Ile Pro Ile Val Tyr Tyr Gly Ser Glu Gln Gly Phe Ser Gly
305                 310                 315                 320
Gly Ala Asp Pro Ala Asn Arg Glu Val Leu Trp Thr Thr Asn Tyr Asp
                325                 330                 335
Thr Ser Ser Asp Leu Tyr Gln Phe Ile Lys Thr Val Asn Ser Val Arg
                340                 345                 350
Met Lys Ser Asn Lys Ala Val Tyr Met Asp Ile Tyr Val Gly Asp Asn
                355                 360                 365
Ala Tyr Ala Phe Lys His Gly Asp Ala Leu Val Val Leu Asn Asn Tyr
                370                 375                 380
Gly Ser Gly Ser Thr Asn Gln Val Ser Phe Ser Val Ser Gly Lys Phe
385                 390                 395                 400
Asp Ser Gly Ala Ser Leu Met Asp Ile Val Ser Asn Ile Thr Thr Thr
                405                 410                 415
Val Ser Ser Asp Gly Thr Val Thr Phe Asn Leu Lys Asp Gly Leu Pro
                420                 425                 430
```

```
Ala Ile Phe Thr Ser Ala Thr Gly Gly Thr Thr Thr Ala Thr Pro
            435                 440                 445

Thr Gly Ser Gly Ser Val Thr Ser Thr Ser Lys Thr Thr Ala Thr Ala
450                 455                 460

Ser Lys Thr Ser Thr Ser Thr Ser Ser Thr Ser Cys Thr Thr Pro Thr
465                 470                 475                 480

Ala Val Ala Val Thr Phe Asp Leu Thr Ala Thr Thr Thr Tyr Gly Glu
                485                 490                 495

Asn Ile Tyr Leu Val Gly Ser Ile Ser Gln Leu Gly Asp Trp Glu Thr
            500                 505                 510

Ser Asp Gly Ile Ala Leu Ser Ala Asp Lys Tyr Thr Ser Ser Asp Pro
            515                 520                 525

Leu Trp Tyr Val Thr Val Thr Leu Pro Ala Gly Glu Ser Phe Glu Tyr
            530                 535                 540

Lys Phe Ile Arg Ile Glu Ser Asp Asp Ser Val Glu Trp Glu Ser Asp
545                 550                 555                 560

Pro Asn Arg Glu Tyr Thr Val Pro Gln Ala Cys Gly Thr Ser Thr Ala
                565                 570                 575

Thr Val Asp Thr Trp Arg
            580

<210> SEQ ID NO 17
<211> LENGTH: 556
<212> TYPE: PRT
<213> ORGANISM: Trametes cingulate

<400> SEQUENCE: 17

Gln Ser Ser Ala Ala Asp Ala Tyr Val Ala Ser Glu Ser Pro Ile Ala
1               5                   10                  15

Lys Ala Gly Val Leu Ala Asn Ile Gly Pro Ser Gly Ser Lys Ser Asn
                20                  25                  30

Gly Ala Lys Ala Gly Ile Val Ile Ala Ser Pro Ser Thr Ser Asn Pro
            35                  40                  45

Asn Tyr Leu Tyr Thr Trp Thr Arg Asp Ser Ser Leu Val Phe Lys Ala
50                  55                  60

Leu Ile Asp Gln Phe Thr Thr Gly Glu Asp Thr Ser Leu Arg Thr Leu
65                  70                  75                  80

Ile Asp Glu Phe Thr Ser Ala Glu Ala Ile Leu Gln Gln Val Pro Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Asp Ala Trp Gly Arg Pro Gln Arg Asp
            115                 120                 125

Gly Pro Ala Leu Arg Ala Thr Ala Ile Ile Thr Tyr Ala Asn Trp Leu
            130                 135                 140

Leu Asp Asn Lys Asn Thr Thr Tyr Val Thr Asn Thr Leu Trp Pro Ile
145                 150                 155                 160

Ile Lys Leu Asp Leu Asp Tyr Val Ala Ser Asn Trp Asn Gln Ser Thr
                165                 170                 175

Phe Asp Leu Trp Glu Glu Ile Asn Ser Ser Phe Phe Thr Thr Ala
            180                 185                 190

Val Gln His Arg Ala Leu Arg Glu Gly Ala Thr Phe Ala Asn Arg Ile
            195                 200                 205

Gly Gln Thr Ser Val Val Ser Gly Tyr Thr Thr Gln Ala Asn Asn Leu
```

```
                210                 215                 220
Leu Cys Phe Leu Gln Ser Tyr Trp Asn Pro Thr Gly Gly Tyr Ile Thr
225                 230                 235                 240

Ala Asn Thr Gly Gly Gly Arg Ser Gly Lys Asp Ala Asn Thr Val Leu
                245                 250                 255

Thr Ser Ile His Thr Phe Asp Pro Ala Ala Gly Cys Asp Ala Val Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Ser Ile Asn Ser Gly Ile Ala Ser Asn
290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Ile Val Trp Asn Lys Leu Gly Ala Leu Asn Val Thr Ser Thr
            340                 345                 350

Ser Leu Pro Phe Phe Gln Gln Phe Ser Ser Gly Val Thr Val Gly Thr
        355                 360                 365

Tyr Ala Ser Ser Ser Ser Thr Phe Lys Thr Leu Thr Ser Ala Ile Lys
370                 375                 380

Thr Phe Ala Asp Gly Phe Leu Ala Val Asn Ala Lys Tyr Thr Pro Ser
385                 390                 395                 400

Asn Gly Gly Leu Ala Glu Gln Tyr Ser Arg Ser Asn Gly Ser Pro Val
                405                 410                 415

Ser Ala Val Asp Leu Thr Trp Ser Tyr Ala Ala Ala Leu Thr Ser Phe
            420                 425                 430

Ala Ala Arg Ser Gly Lys Thr Tyr Ala Ser Trp Gly Ala Ala Gly Leu
        435                 440                 445

Thr Val Pro Thr Thr Cys Ser Gly Ser Gly Ala Gly Thr Val Ala
        450                 455                 460

Val Thr Phe Asn Val Gln Ala Thr Thr Val Phe Gly Glu Asn Ile Tyr
465                 470                 475                 480

Ile Thr Gly Ser Val Pro Ala Leu Gln Asn Trp Ser Pro Asp Asn Ala
                485                 490                 495

Leu Ile Leu Ser Ala Ala Asn Tyr Pro Thr Trp Ser Ile Thr Val Asn
            500                 505                 510

Leu Pro Ala Ser Thr Thr Ile Glu Tyr Lys Tyr Ile Arg Lys Phe Asn
        515                 520                 525

Gly Ala Val Thr Trp Glu Ser Asp Pro Asn Asn Ser Ile Thr Thr Pro
530                 535                 540

Ala Ser Gly Thr Phe Thr Gln Asn Asp Thr Trp Arg
545                 550                 555

<210> SEQ ID NO 18
<211> LENGTH: 591
<212> TYPE: PRT
<213> ORGANISM: Talaromyces emersonii

<400> SEQUENCE: 18

Ala Thr Gly Ser Leu Asp Ser Phe Leu Ala Thr Glu Thr Pro Ile Ala
1               5                   10                  15

Leu Gln Gly Val Leu Asn Asn Ile Gly Pro Asn Gly Ala Asp Val Ala
            20                  25                  30
```

```
Gly Ala Ser Ala Gly Ile Val Val Ala Ser Pro Ser Arg Ser Asp Pro
             35                  40                  45

Asn Tyr Phe Tyr Ser Trp Thr Arg Asp Ala Ala Leu Thr Ala Lys Tyr
 50                  55                  60

Leu Val Asp Ala Phe Ile Ala Gly Asn Lys Asp Leu Glu Gln Thr Ile
 65                  70                  75                  80

Gln Gln Tyr Ile Ser Ala Gln Ala Lys Val Gln Thr Ile Ser Asn Pro
                 85                  90                  95

Ser Gly Asp Leu Ser Thr Gly Gly Leu Gly Pro Lys Phe Asn Val
                100                 105                 110

Asn Glu Thr Ala Phe Thr Gly Pro Trp Gly Arg Pro Gln Arg Asp Gly
            115                 120                 125

Pro Ala Leu Arg Ala Thr Ala Leu Ile Ala Tyr Ala Asn Tyr Leu Ile
        130                 135                 140

Asp Asn Gly Glu Ala Ser Thr Ala Asp Glu Ile Ile Trp Pro Ile Val
145                 150                 155                 160

Gln Asn Asp Leu Ser Tyr Ile Thr Gln Tyr Trp Asn Ser Ser Thr Phe
                165                 170                 175

Asp Leu Trp Glu Glu Val Glu Gly Ser Ser Phe Phe Thr Thr Ala Val
            180                 185                 190

Gln His Arg Ala Leu Val Glu Gly Asn Ala Leu Ala Thr Arg Leu Asn
        195                 200                 205

His Thr Cys Ser Asn Cys Val Ser Gln Ala Pro Gln Val Leu Cys Phe
    210                 215                 220

Leu Gln Ser Tyr Trp Thr Gly Ser Tyr Val Leu Ala Asn Phe Gly Gly
225                 230                 235                 240

Ser Gly Arg Ser Gly Lys Asp Val Asn Ser Ile Leu Gly Ser Ile His
                245                 250                 255

Thr Phe Asp Pro Ala Gly Gly Cys Asp Asp Ser Thr Phe Gln Pro Cys
            260                 265                 270

Ser Ala Arg Ala Leu Ala Asn His Lys Val Val Thr Asp Ser Phe Arg
        275                 280                 285

Ser Ile Tyr Ala Ile Asn Ser Gly Ile Ala Glu Gly Ser Ala Val Ala
    290                 295                 300

Val Gly Arg Tyr Pro Glu Asp Val Tyr Gln Gly Gly Asn Pro Trp Tyr
305                 310                 315                 320

Leu Ala Thr Ala Ala Ala Glu Gln Leu Tyr Asp Ala Ile Tyr Gln
                325                 330                 335

Trp Lys Lys Ile Gly Ser Ile Ser Ile Thr Asp Val Ser Leu Pro Phe
            340                 345                 350

Phe Gln Asp Ile Tyr Pro Ser Ala Ala Val Gly Thr Tyr Asn Ser Gly
        355                 360                 365

Ser Thr Thr Phe Asn Asp Ile Ile Ser Ala Val Gln Thr Tyr Gly Asp
    370                 375                 380

Gly Tyr Leu Ser Ile Val Glu Lys Tyr Thr Pro Ser Asp Gly Ser Leu
385                 390                 395                 400

Thr Glu Gln Phe Ser Arg Thr Asp Gly Thr Pro Leu Ser Ala Ser Ala
                405                 410                 415

Leu Thr Trp Ser Tyr Ala Ser Leu Leu Thr Ala Ser Ala Arg Arg Gln
            420                 425                 430

Ser Val Val Pro Ala Ser Trp Gly Glu Ser Ser Ala Ser Ser Val Pro
        435                 440                 445

Ala Val Cys Ser Ala Thr Ser Ala Thr Gly Pro Tyr Ser Thr Ala Thr
```

```
            450                 455                 460
Asn Thr Val Trp Pro Ser Gly Ser Gly Ser Thr Thr Thr Ser
465                 470                 475                 480

Ser Ala Pro Cys Thr Thr Pro Thr Ser Val Ala Val Thr Phe Asp Glu
                    485                 490                 495

Ile Val Ser Thr Ser Tyr Gly Glu Thr Ile Tyr Leu Ala Gly Ser Ile
                    500                 505                 510

Pro Glu Leu Gly Asn Trp Ser Thr Ala Ser Ala Ile Pro Leu Arg Ala
                515                 520                 525

Asp Ala Tyr Thr Asn Ser Asn Pro Leu Trp Tyr Val Thr Val Asn Leu
            530                 535                 540

Pro Pro Gly Thr Ser Phe Glu Tyr Lys Phe Phe Lys Asn Gln Thr Asp
545                 550                 555                 560

Gly Thr Ile Val Trp Glu Asp Asp Pro Asn Arg Ser Tyr Thr Val Pro
                    565                 570                 575

Ala Tyr Cys Gly Gln Thr Thr Ala Ile Leu Asp Asp Ser Trp Gln
                580                 585                 590

<210> SEQ ID NO 19
<211> LENGTH: 555
<212> TYPE: PRT
<213> ORGANISM: Pycnoporus sanguineus

<400> SEQUENCE: 19

Gln Ser Ser Ala Val Asp Ala Tyr Val Ala Ser Glu Ser Pro Ile Ala
1               5                   10                  15

Lys Gln Gly Val Leu Asn Asn Ile Gly Pro Asn Gly Ser Lys Ala His
                20                  25                  30

Gly Ala Lys Ala Gly Ile Val Val Ala Ser Pro Ser Thr Glu Asn Pro
            35                  40                  45

Asp Tyr Leu Tyr Thr Trp Thr Arg Asp Ser Ser Leu Val Phe Lys Leu
    50                  55                  60

Leu Ile Asp Gln Phe Thr Ser Gly Asp Asp Thr Ser Leu Arg Gly Leu
65                  70                  75                  80

Ile Asp Asp Phe Thr Ser Ala Glu Ala Ile Leu Gln Gln Val Ser Asn
                85                  90                  95

Pro Ser Gly Thr Val Ser Thr Gly Gly Leu Gly Glu Pro Lys Phe Asn
            100                 105                 110

Ile Asp Glu Thr Ala Phe Thr Gly Ala Trp Gly Arg Pro Gln Arg Asp
        115                 120                 125

Gly Pro Ala Leu Arg Ala Thr Ser Ile Ile Arg Tyr Ala Asn Trp Leu
    130                 135                 140

Leu Asp Asn Gly Asn Thr Thr Tyr Val Ser Asn Thr Leu Trp Pro Val
145                 150                 155                 160

Ile Gln Leu Asp Leu Asp Tyr Val Ala Asp Asn Trp Asn Gln Ser Thr
                165                 170                 175

Phe Asp Leu Trp Glu Glu Val Asp Ser Ser Phe Phe Thr Thr Ala
            180                 185                 190

Val Gln His Arg Ala Leu Arg Glu Gly Ala Thr Phe Ala Ser Arg Ile
        195                 200                 205

Gly Gln Ser Ser Val Val Ser Gly Tyr Thr Thr Gln Ala Asp Asn Leu
    210                 215                 220

Leu Cys Phe Leu Gln Ser Tyr Trp Asn Pro Ser Gly Gly Tyr Val Thr
225                 230                 235                 240
```

```
Ala Asn Thr Gly Gly Gly Arg Ser Gly Lys Asp Ser Asn Thr Val Leu
                245                 250                 255

Thr Ser Ile His Thr Phe Asp Pro Ala Ala Gly Cys Asp Ala Ala Thr
            260                 265                 270

Phe Gln Pro Cys Ser Asp Lys Ala Leu Ser Asn Leu Lys Val Tyr Val
        275                 280                 285

Asp Ala Phe Arg Ser Ile Tyr Thr Ile Asn Asn Gly Ile Ala Ser Asn
    290                 295                 300

Ala Ala Val Ala Thr Gly Arg Tyr Pro Glu Asp Ser Tyr Met Gly Gly
305                 310                 315                 320

Asn Pro Trp Tyr Leu Thr Thr Ser Ala Val Ala Glu Gln Leu Tyr Asp
                325                 330                 335

Ala Leu Tyr Val Trp Asp Gln Leu Gly Gly Leu Asn Val Thr Ser Thr
            340                 345                 350

Ser Leu Ala Phe Phe Gln Gln Phe Ala Ser Gly Leu Ser Thr Gly Thr
        355                 360                 365

Tyr Ser Ala Ser Ser Ser Thr Tyr Ala Thr Leu Thr Ser Ala Ile Arg
    370                 375                 380

Ser Phe Ala Asp Gly Phe Leu Ala Ile Asn Ala Lys Tyr Thr Pro Ala
385                 390                 395                 400

Asp Gly Gly Leu Ala Glu Gln Tyr Ser Arg Asn Asp Gly Thr Pro Leu
                405                 410                 415

Ser Ala Val Asp Leu Thr Trp Ser Tyr Ala Ala Ala Leu Thr Ala Phe
            420                 425                 430

Ala Ala Arg Glu Gly Lys Thr Tyr Gly Ser Trp Gly Ala Ala Gly Leu
        435                 440                 445

Thr Val Pro Ala Ser Cys Ser Gly Gly Gly Ala Thr Val Ala Val
    450                 455                 460

Thr Phe Asn Val Gln Ala Thr Thr Val Phe Gly Glu Asn Ile Tyr Ile
465                 470                 475                 480

Thr Gly Ser Val Ala Ala Leu Gln Asn Trp Ser Pro Asp Asn Ala Leu
                485                 490                 495

Ile Leu Ser Ala Ala Asn Tyr Pro Thr Trp Ser Ile Thr Val Asn Leu
            500                 505                 510

Pro Ala Asn Thr Val Val Gln Tyr Lys Tyr Ile Arg Lys Phe Asn Gly
        515                 520                 525

Gln Val Thr Trp Glu Ser Asp Pro Asn Asn Gln Ile Thr Thr Pro Ser
    530                 535                 540

Gly Gly Ser Phe Thr Gln Asn Asp Val Trp Arg
545                 550                 555

<210> SEQ ID NO 20
<211> LENGTH: 556
<212> TYPE: PRT
<213> ORGANISM: Gloeophyllum sepiarium

<400> SEQUENCE: 20

Gln Ser Val Asp Ser Tyr Val Ser Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ser Ala Gly Val Val Val Ala Ser Pro Ser Thr Ser Asp Pro Asp Tyr
        35                  40                  45

Trp Tyr Thr Trp Thr Arg Asp Ser Ser Leu Val Phe Lys Ser Leu Ile
    50                  55                  60
```

```
Asp Gln Tyr Thr Thr Gly Ile Asp Ser Thr Ser Ser Leu Arg Thr Leu
 65                  70                  75                  80

Ile Asp Asp Phe Val Thr Ala Glu Ala Asn Leu Gln Gln Val Ser Asn
                 85                  90                  95

Pro Ser Gly Thr Leu Thr Thr Gly Gly Leu Gly Glu Pro Lys Phe Asn
                100                 105                 110

Val Asp Glu Thr Ala Phe Thr Gly Ala Trp Gly Arg Pro Gln Arg Asp
                115                 120                 125

Gly Pro Ala Leu Arg Ser Thr Ala Leu Ile Thr Tyr Gly Asn Trp Leu
130                 135                 140

Leu Ser Asn Gly Asn Thr Ser Tyr Val Thr Ser Asn Leu Trp Pro Ile
145                 150                 155                 160

Ile Gln Asn Asp Leu Gly Tyr Val Val Ser Tyr Trp Asn Gln Ser Thr
                165                 170                 175

Tyr Asp Leu Trp Glu Glu Val Asp Ser Ser Ser Phe Phe Thr Thr Ala
                180                 185                 190

Val Gln His Arg Ala Leu Arg Glu Gly Ala Ala Phe Ala Thr Ala Ile
                195                 200                 205

Gly Gln Thr Ser Gln Val Ser Ser Tyr Thr Thr Gln Ala Asp Asn Leu
210                 215                 220

Leu Cys Phe Leu Gln Ser Tyr Trp Asn Pro Ser Gly Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Ala Thr
                260                 265                 270

Phe Gln Pro Cys Ser Asp Lys Ala Leu Ser Asn Leu Lys Val Tyr Val
                275                 280                 285

Asp Ser Phe Arg Ser Val Tyr Ser Ile Asn Ser Gly Val Ala Ser Asn
                290                 295                 300

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
                325                 330                 335

Ala Leu Asn Val Trp Glu Ser Gln Gly Ser Leu Glu Val Thr Ser Thr
                340                 345                 350

Ser Leu Ala Phe Phe Gln Gln Phe Ser Ser Gly Val Thr Ala Gly Thr
                355                 360                 365

Tyr Ser Ser Ser Ser Thr Tyr Ser Thr Leu Thr Ser Ala Ile Lys
                370                 375                 380

Asn Phe Ala Asp Gly Phe Val Ala Ile Asn Ala Lys Tyr Thr Pro Ser
385                 390                 395                 400

Asn Gly Gly Leu Ala Glu Gln Tyr Ser Lys Ser Asp Gly Ser Pro Leu
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Ala Gly Leu
                435                 440                 445

Thr Val Pro Ser Ser Cys Ser Gly Asn Ser Gly Pro Thr Val Ala
                450                 455                 460

Val Thr Phe Asn Val Asn Ala Glu Thr Val Trp Gly Glu Asn Ile Tyr
465                 470                 475                 480
```

```
Leu Thr Gly Ser Val Asp Ala Leu Glu Asn Trp Ser Ala Asp Asn Ala
                    485                 490                 495

Leu Leu Leu Ser Ser Ala Asn Tyr Pro Thr Trp Ser Ile Thr Val Asn
                500                 505                 510

Leu Pro Ala Ser Thr Ala Ile Glu Tyr Lys Tyr Ile Arg Lys Asn Asn
            515                 520                 525

Gly Ala Val Thr Trp Glu Ser Asp Pro Asn Asn Ser Ile Thr Thr Pro
        530                 535                 540

Ala Ser Gly Ser Thr Thr Glu Asn Asp Thr Trp Arg
545                 550                 555

<210> SEQ ID NO 21
<211> LENGTH: 559
<212> TYPE: PRT
<213> ORGANISM: Gloeophyllum trabeum

<400> SEQUENCE: 21

Gln Ser Val Asp Ser Tyr Val Gly Ser Glu Gly Pro Ile Ala Lys Ala
1               5                   10                  15

Gly Val Leu Ala Asn Ile Gly Pro Asn Gly Ser Lys Ala Ser Gly Ala
            20                  25                  30

Ala Ala Gly Val Val Ala Ser Pro Ser Lys Ser Asp Pro Asp Tyr
        35                  40                  45

Trp Tyr Thr Trp Thr Arg Asp Ser Ser Leu Val Phe Lys Ser Leu Ile
    50                  55                  60

Asp Gln Tyr Thr Thr Gly Ile Asp Ser Thr Ser Ser Leu Arg Ser Leu
65                  70                  75                  80

Ile Asp Ser Phe Val Ile Ala Glu Ala Asn Ile Gln Gln Val Ser Asn
                85                  90                  95

Pro Ser Gly Thr Leu Thr Thr Gly Leu Gly Glu Pro Lys Phe Asn
            100                 105                 110

Val Asp Glu Thr Ala Phe Thr Gly Ala Trp Gly Arg Pro Gln Arg Asp
        115                 120                 125

Gly Pro Ala Leu Arg Ala Thr Ala Leu Ile Thr Tyr Gly Asn Trp Leu
    130                 135                 140

Leu Ser Asn Gly Asn Thr Thr Trp Val Thr Ser Thr Leu Trp Pro Ile
145                 150                 155                 160

Ile Gln Asn Asp Leu Asn Tyr Val Val Gln Tyr Trp Asn Gln Thr Thr
                165                 170                 175

Phe Asp Leu Trp Glu Glu Val Asn Ser Ser Ser Phe Phe Thr Thr Ala
            180                 185                 190

Val Gln His Arg Ala Leu Arg Glu Gly Ala Ala Phe Ala Thr Lys Ile
        195                 200                 205

Gly Gln Thr Ser Ser Val Ser Ser Tyr Thr Thr Gln Ala Ala Asn Leu
    210                 215                 220

Leu Cys Phe Leu Gln Ser Tyr Trp Asn Pro Thr Ser Gly Tyr Ile Thr
225                 230                 235                 240

Ala Asn Thr Gly Gly Gly Arg Ser Gly Lys Asp Ala Asn Thr Leu Leu
                245                 250                 255

Ala Ser Ile His Thr Tyr Asp Pro Ser Ala Gly Cys Asp Ala Thr Thr
            260                 265                 270

Phe Gln Pro Cys Ser Asp Lys Ala Leu Ser Asn Leu Lys Val Tyr Val
        275                 280                 285

Asp Ser Phe Arg Ser Val Tyr Ser Ile Asn Ser Gly Ile Ala Ser Asn
    290                 295                 300
```

Ala Ala Val Ala Thr Gly Arg Tyr Pro Glu Asp Ser Tyr Gln Gly Gly
305                 310                 315                 320

Asn Pro Trp Tyr Leu Thr Thr Phe Ala Val Ala Glu Gln Leu Tyr Asp
            325                 330                 335

Ala Leu Asn Val Trp Ala Ala Gln Gly Ser Leu Asn Val Thr Ser Ile
            340                 345                 350

Ser Leu Pro Phe Phe Gln Gln Phe Ser Ser Val Thr Ala Gly Thr
    355                 360                 365

Tyr Ala Ser Ser Ser Thr Thr Tyr Thr Thr Leu Thr Ser Ala Ile Lys
    370                 375                 380

Ser Phe Ala Asp Gly Phe Val Ala Ile Asn Ala Gln Tyr Thr Pro Ser
385                 390                 395                 400

Asn Gly Gly Leu Ala Glu Gln Phe Ser Arg Ser Asn Gly Ala Pro Val
                405                 410                 415

Ser Ala Val Asp Leu Thr Trp Ser Tyr Ala Ser Ala Leu Thr Ala Phe
                420                 425                 430

Glu Ala Arg Asn Asn Thr Gln Phe Ala Gly Trp Gly Ala Val Gly Leu
            435                 440                 445

Thr Val Pro Thr Ser Cys Ser Ser Asn Ser Gly Gly Gly Gly Ser
    450                 455                 460

Thr Val Ala Val Thr Phe Asn Val Asn Ala Gln Thr Val Trp Gly Glu
465                 470                 475                 480

Asn Ile Tyr Ile Thr Gly Ser Val Asp Ala Leu Ser Asn Trp Ser Pro
                485                 490                 495

Asp Asn Ala Leu Leu Leu Ser Ser Ala Asn Tyr Pro Thr Trp Ser Ile
                500                 505                 510

Thr Val Asn Leu Pro Ala Ser Thr Ala Ile Gln Tyr Lys Tyr Ile Arg
            515                 520                 525

Lys Asn Asn Gly Ala Val Thr Trp Glu Ser Asp Pro Asn Asn Ser Ile
530                 535                 540

Thr Thr Pro Ala Ser Gly Ser Val Thr Glu Asn Asp Thr Trp Arg
545                 550                 555

<210> SEQ ID NO 22
<211> LENGTH: 515
<212> TYPE: PRT
<213> ORGANISM: Bacillus stearothermophilus

<400> SEQUENCE: 22

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
                100                 105                 110

Thr Glu Trp Val Asp Ala Val Glu Val Asn Pro Ser Asp Arg Asn Gln

```
               115                 120                 125
Glu Ile Ser Gly Thr Tyr Gln Ile Gln Ala Trp Thr Lys Phe Asp Phe
        130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Ile Gly Lys Ala Trp Asp Trp Glu Val Asp Thr Glu
            180                 185                 190

Asn Gly Asn Tyr Asp Tyr Leu Met Tyr Ala Asp Leu Asp Met Asp His
        195                 200                 205

Pro Glu Val Val Thr Glu Leu Lys Asn Trp Gly Lys Trp Tyr Val Asn
    210                 215                 220

Thr Thr Asn Ile Asp Gly Phe Arg Leu Asp Ala Val Lys His Ile Lys
225                 230                 235                 240

Phe Ser Phe Phe Pro Asp Trp Leu Ser Tyr Val Arg Ser Gln Thr Gly
                245                 250                 255

Lys Pro Leu Phe Thr Val Gly Glu Tyr Trp Ser Tyr Asp Ile Asn Lys
            260                 265                 270

Leu His Asn Tyr Ile Thr Lys Thr Asn Gly Thr Met Ser Leu Phe Asp
        275                 280                 285

Ala Pro Leu His Asn Lys Phe Tyr Thr Ala Ser Lys Ser Gly Gly Ala
    290                 295                 300

Phe Asp Met Arg Thr Leu Met Thr Asn Thr Leu Met Lys Asp Gln Pro
305                 310                 315                 320

Thr Leu Ala Val Thr Phe Val Asp Asn His Asp Thr Glu Pro Gly Gln
                325                 330                 335

Ala Leu Gln Ser Trp Val Asp Pro Trp Phe Lys Pro Leu Ala Tyr Ala
            340                 345                 350

Phe Ile Leu Thr Arg Gln Glu Gly Tyr Pro Cys Val Phe Tyr Gly Asp
        355                 360                 365

Tyr Tyr Gly Ile Pro Gln Tyr Asn Ile Pro Ser Leu Lys Ser Lys Ile
    370                 375                 380

Asp Pro Leu Leu Ile Ala Arg Arg Asp Tyr Ala Tyr Gly Thr Gln His
385                 390                 395                 400

Asp Tyr Leu Asp His Ser Asp Ile Ile Gly Trp Thr Arg Glu Gly Val
                405                 410                 415

Thr Glu Lys Pro Gly Ser Gly Leu Ala Ala Leu Ile Thr Asp Gly Pro
            420                 425                 430

Gly Gly Ser Lys Trp Met Tyr Val Gly Lys Gln His Ala Gly Lys Val
        435                 440                 445

Phe Tyr Asp Leu Thr Gly Asn Arg Ser Asp Thr Val Thr Ile Asn Ser
    450                 455                 460

Asp Gly Trp Gly Glu Phe Lys Val Asn Gly Gly Ser Val Ser Val Trp
465                 470                 475                 480

Val Pro Arg Lys Thr Thr Val Ser Thr Ile Ala Arg Pro Ile Thr Thr
                485                 490                 495

Arg Pro Trp Thr Gly Glu Phe Val Arg Trp Thr Glu Pro Arg Leu Val
            500                 505                 510

Ala Trp Pro
        515

<210> SEQ ID NO 23
```

```
<211> LENGTH: 1704
<212> TYPE: DNA
<213> ORGANISM: Polyporus arcularius

<400> SEQUENCE: 23
atggtggcaa ctaggggttt gttcttcgtg tccttgttcg cattggccct cggtaagccc      60
atggccaggt cgatgaagct ccacgaatcg cgagagggta tccctgaagg cttctccttg     120
aggggagcag cccagcctga gcagacgatc aagctccgtt tggcgttggt gcagtccaac     180
ttcgccgagt tggagcggaa gttgatggac gtgtcgacgc cgtcgtcggc gaactatggc     240
aagcacttgt ccaaggccga ggtccagcag ttggtggcac ctacccagga ctccgtggat     300
gccgtgaagt cgtggctcaa agaaaacgat atctcggcca agacgatctc ggcaaccgga     360
gattggttgt ccttcgaggt ccccgtctcg aaggccaacg agttgttcga cgcagatttc     420
tcgatctaca cccacgacga aaccggtacc gaagccgtgc gcacattgtc ctactccatt     480
cctgccgaac tccagggtca cttggatctc gtccacccca cagtgacttt ccccaaccct     540
cgcggattgc tcctgtgtt cacagcaccc atcaaagcag aagcccagaa cttgacatcc     600
agggcgacca ttccgtcctc gtgtgccagg acaatcacac cggcatgtct ccaggcaatc     660
tacaacatcc cttcgacccc tgccacagag tcgtccaaca agttggcagt caccggattc     720
atcgaacagt tcgccaacaa ggcggacttg aaaactttct tgacacgatt caggaccgac     780
atctcctcgt ccacctcgtt cacactccag acactcgatg gtggctccaa ccctcagtcc     840
tcgtccgaag caggagtcga agccaacttg gatatccagt acaccgtggg cgtggcaaca     900
ggtgtcccca ccgtgttcat ctcggtggga gaggacttcc aggatggtga tttggaggga     960
ttcttggatg tcgtcaactc gttgttggac gaggatacac ctccgttcgt gatgacgacc    1020
tcgtacggcc agaacgagaa cacgatctcg aggaacctcg ccaacaactt gtgtaacgca    1080
tacgcgcagt tgggagcgcg tggcgtgtcc atcttgttcg cgtccggaga tggaggcgtc    1140
gcaggttcgc agtccgcgtc gtgttcgaag ttcgtgccta cattcccctc cggttgtccc    1200
ttcatgacct cggtcggagc cactcaggga ttctcgcctg agactgcagc cgatttctcc    1260
tcgggtggtt tctcgaacta cttcgccatc ccggattacc agaccacggc agtctcggga    1320
tacatcaagg cgctcggtaa caccaactcg ggcaagtaca acgcaaccgg tcgaggattc    1380
ccggatatcg caacccaggg cgtcaacttc gaggtggtgg tcgtggcca gtcgggcacg    1440
gtggagggca cctcctgttc ctcgcccact ctcgcatcga tcatctccct cctcaacgac    1500
cgattgattg cggcaggtaa atcgcctctc ggtttcttga ccccttcct ctattccacg    1560
ggcacttccg cactcaacga cattacatcg ggatcgaacc ctggctgtaa cacgaacgga    1620
ttccctgcaa aagccggatg ggaccccggtc accggcttgg gcacacccga cttcaacaag    1680
ctcttgtcgg cagtgggcct ctaa                                            1704

<210> SEQ ID NO 24
<211> LENGTH: 1698
<212> TYPE: DNA
<213> ORGANISM: Lenzites betulinus

<400> SEQUENCE: 24
atggtggcaa cgtccttgtt cgtggcagcc ctcatcacct tggcagtggg caagcccatg     60
ggacggaact tgaaggtgca cgaagcacgc gaagagatcc cggacggttt ctcgctccag    120
ggttccgcag caccccgacac tacactcaaa ctcaggatcg cattggtcca gtcgaacttc    180
gcagaattgg agcagaagct ctacgacgtc tccaccccct cctcgccgaa ctatggagcg    240
```

```
catttgtcga aggaggaggt ggagcagttg gtggcacctt cggcagattc ggtcgacgcc      300
gtgaacgcct ggttgaagga aaacgatttg tcggcacaga ccatctcgcc tgcaggagat      360
tggctcgcgt tcgaggtccc tgtctcgaaa gcaaacgaac tcttcgatgc cgacttctcg      420
gtcttcacac atgatcagac cggattggaa gcgatcagga caatgtcgta ctcgattccg      480
gcagagttgc agggtcattt ggatctcgtc caccctacag tcaccttccc caacccttac      540
tcgcacctcc ctgtcgtgcg ctcgcccatc aaggcctcgc agaacctcac ctccagggca      600
acgatccctg cctcctgtgc atccacaatt actcctgcct gtctccagga tatctatggc      660
atcccgacaa ctaaggccac gcagtcctcg aacaagctcg ccgtctccgg cttcatcgac      720
cagttcgcaa actccgcaga tttggcaacc ttcctcaaga agttcaggac agatatctcg      780
tccaccacta cgttcgcact ccagaccctc gacggaggtt ccaactcgca gtccggctcc      840
caggcaggag tggaagccaa cctcgatatc cagtataccg tgggcttggc ctcgggagtg      900
cccgtcacgt tcatttccgt gggcgataac ttccaggacg tgatttgga gggtttcttg      960 gacatcatta acttcttgtt ggccgaatcg gcacctcccc aggtcctcac gacctcctac     1020
ggacagaacg agaacactat ctcggtgaaa ttggccaacc agttgtgtaa cgcctacgcg     1080
cagctcggag cacgcggtac ttcgatcctc ttcgcctcgg gagacggtgg agtgtccggt     1140
tcgcagtcgt cctcgtgttc caaattcgtg cctacattcc cttccggttg tccgttcatg     1200
acatcggtgg gagcaaccca gggcgtgaac cccgagacag ccgcagattt ctcgtcggga     1260
ggattctcca actacttcgg tatcccttcc taccaggcaa ccgcagtcaa gacgtacttg     1320
acggccttgg gaacaacgaa ctccggaaag ttcaacactt cgggacgagc cttccccgat     1380
gtgtcgactc agggcgtcga cttcgaaatc gtcgtcgatg gtcgaactga gggagtcgat     1440
ggaacttcct gtgcatcccc cacgttcgca gcgatcatct cgctcgtcaa cgacaaactc     1500
attgccgcag gcaagtcgcc tctcggattc ctcaaccccc tcctctattc cacaggcgca     1560
tcggcattca ccgacattac ctcgggttcc aaccctggcg taacaccaa gggcttccct     1620 gcgaaagccg gttgggaccc tgtcacagga ctcggcacac ccaacttcgc gaagctcctc     1680
gcagcagcag gcgtctaa                                                    1698
```

<210> SEQ ID NO 25  
<211> LENGTH: 1880  
<212> TYPE: DNA  
<213> ORGANISM: Ganoderma lucidum

<400> SEQUENCE: 25

```
atggttgcct ccggcttgct ccttgcttcc ctcgtcaccc ttgccttggg caagaccgcc       60
actcgcaacc tcaagctcca tgagacaagc cagggcgctc ccagcggctt ctctctcact      120
ggctctgcgg acccccgacca gaccttgaag ttgcgtctcg ccctcgtcca gggcaacgtc      180
gccgagcttg agcgcaggct ctacgacgtc agcacaccat caagtccgaa ctacggcaag      240
cacctgtcga agtctgaggt attattccgt tgccgttacc ctcattctaa tgttctctct      300
ctaatctgtt tgcgtcacac acaggtacaa cagctcgttg cccccgcaca agatagcatc      360
gatgctatca atgcgtggct taaggagaac gggatctcgg ctaagacgac ctccgccacc      420
ggcgattggc tctcgttcga ggtccctgtc agcaaggcca acgagctctt cgacgccgac      480
ttctcagtgt acaagcacca tgacaccggc atggaggttg ccgcaccct ctcgtactcg      540 attccggccg aactccaggc ccacctcgac cttgtccacc cgacggtgac gttcccgaac      600
```

```
ccgaagggcc accctccggt cttccaagca ccggccatga tcaccaatga tgttcagaac    660
ttcagcgccg gggccgttcc gtcatcgtgc tcgagccgca tcactcctgc ttgcctgcag    720
gctctttaca acatcccgtc ggacccggca acacagccgt caaacaagct cgccgtcact    780
ggttatattg agcagtacgc taatcaggat gaccttgcgg tacgcttacg ccattcaaat    840
ctggtaccat caacccaata ctgatcgatt tacctgccgt caggtcttct tgaaggagta    900
tcgtgccgac atgtcatcga acacgacctt caccctccag acactcgatg gtggcgttaa    960
ctctcaaacg gacgaggctg gtatcgaagc gaaccttgac gttcagtaca cggtcggtat   1020
cgccactggt gtcccgacgg tcttcatctc tgtcggtgat cagtaccagg acggcaacct   1080
cgagggcttc ctcgacgttg tcaacttcct ccttgacgaa gatacccctc cctatgttat   1140
gacaacttcc tacggccagg acgaacacac catgtcgcgg aaactcgcgc agtgcgtaca   1200
tctcatcttc ctatgagcgg tcgctcacgc atctcgcttg caggaacctt tgcaacgcat   1260
acgcccagct cggcgctcgc ggtgtgtcca tcctcttcgc ctccggtgat ggcggcgtcg   1320
caggctcgcg gtcctccagc tgctccaagt tcgtccccac cttcccctcg ggctgccccc   1380
acatgacctc cgtcggcgcc acccaaggtg tgcccgagac cgcggccgac ttctcctccg   1440
gcggcttctc caactacttc ggcatccccg actaccaggc ctccgccgtc agcggctacc   1500
tctccgcgct cgggcacacg aacaagggca gtacaacgc gtcgggccgt ggattccctg   1560
acgtgtccac gcagggcgtc aacttcgaag tcatggtcga cggcgcgctc gagggcgtct   1620
cgggcacttc cgccgcgtcg cccacgttcg cggctgttgt tgcgctcctc aatgacaggc   1680
tcatcgcggc gggcaagagc ccccttgggt tcctcaaccc tttcctgtac tcgaagggcg   1740
tgtccgcgct caacgacatc acgtccggct ccaacccggg ctgcaggacg aacggcttcc   1800
cagcgaagga gggctgggac ccggtcaccg gtcttggtac gcccgacttc cagaagctcg   1860
cgtctgccgc tggcctctaa                                               1880
```

```
<210> SEQ ID NO 26
<211> LENGTH: 565
<212> TYPE: PRT
<213> ORGANISM: Ganoderma lucidum

<400> SEQUENCE: 26
```

Met Val Ala Ser Gly Leu Leu Leu Ala Ser Leu Val Thr Leu Ala Leu
1               5                   10                  15

Gly Lys Thr Ala Thr Arg Asn Leu Lys Leu His Glu Thr Ser Gln Gly
            20                  25                  30

Ala Pro Ser Gly Phe Ser Leu Thr Gly Ser Ala Asp Pro Asp Gln Thr
        35                  40                  45

Leu Lys Leu Arg Leu Ala Leu Val Gln Gly Asn Val Ala Glu Leu Glu
    50                  55                  60

Arg Arg Leu Tyr Asp Val Ser Thr Pro Ser Pro Asn Tyr Gly Lys
65                  70                  75                  80

His Leu Ser Lys Ser Glu Val Gln Gln Leu Val Ala Pro Ala Gln Asp
                85                  90                  95

Ser Ile Asp Ala Ile Asn Ala Trp Leu Lys Glu Asn Gly Ile Ser Ala
            100                 105                 110

Lys Thr Thr Ser Ala Thr Gly Asp Trp Leu Ser Phe Glu Val Pro Val
        115                 120                 125

Ser Lys Ala Asn Glu Leu Phe Asp Ala Asp Phe Ser Val Tyr Lys His
    130                 135                 140

His Asp Thr Gly Met Glu Val Val Arg Thr Leu Ser Tyr Ser Ile Pro
145                 150                 155                 160

Ala Glu Leu Gln Ala His Leu Asp Leu Val His Pro Thr Val Thr Phe
            165                 170                 175

Pro Asn Pro Lys Gly His Pro Val Phe Gln Ala Pro Ala Met Ile
        180                 185                 190

Thr Asn Asp Val Gln Asn Phe Ser Ala Gly Ala Val Pro Ser Ser Cys
        195                 200                 205

Ser Ser Arg Ile Thr Pro Ala Cys Leu Gln Ala Leu Tyr Asn Ile Pro
    210                 215                 220

Ser Asp Pro Ala Thr Gln Pro Ser Asn Lys Leu Ala Val Thr Gly Tyr
225                 230                 235                 240

Ile Glu Gln Tyr Ala Asn Gln Asp Asp Leu Ala Val Phe Leu Lys Glu
                245                 250                 255

Tyr Arg Ala Asp Met Ser Ser Asn Thr Thr Phe Thr Leu Gln Thr Leu
                260                 265                 270

Asp Gly Gly Val Asn Ser Gln Thr Asp Glu Ala Gly Ile Glu Ala Asn
            275                 280                 285

Leu Asp Val Gln Tyr Thr Val Gly Ile Ala Thr Gly Val Pro Thr Val
290                 295                 300

Phe Ile Ser Val Gly Asp Gln Tyr Gln Asp Gly Asn Leu Glu Gly Phe
305                 310                 315                 320

Leu Asp Val Val Asn Phe Leu Leu Asp Glu Asp Thr Pro Pro Tyr Val
                325                 330                 335

Met Thr Thr Ser Tyr Gly Gln Asp Glu His Thr Met Ser Arg Lys Leu
                340                 345                 350

Ala Gln Asn Leu Cys Asn Ala Tyr Ala Gln Leu Gly Ala Arg Gly Val
            355                 360                 365

Ser Ile Leu Phe Ala Ser Gly Asp Gly Val Ala Gly Ser Arg Ser
    370                 375                 380

Ser Ser Cys Ser Lys Phe Val Pro Thr Phe Pro Ser Gly Cys Pro Tyr
385                 390                 395                 400

Met Thr Ser Val Gly Ala Thr Gln Gly Val Pro Glu Thr Ala Ala Asp
                405                 410                 415

Phe Ser Ser Gly Gly Phe Ser Asn Tyr Phe Gly Ile Pro Asp Tyr Gln
                420                 425                 430

Ala Ser Ala Val Ser Gly Tyr Leu Ser Ala Leu Gly His Thr Asn Lys
        435                 440                 445

Gly Lys Tyr Asn Ala Ser Gly Arg Gly Phe Pro Asp Val Ser Thr Gln
    450                 455                 460

Gly Val Asn Phe Glu Val Met Val Asp Gly Ala Leu Glu Gly Val Ser
465                 470                 475                 480

Gly Thr Ser Ala Ala Ser Pro Thr Phe Ala Ala Val Val Ala Leu Leu
            485                 490                 495

Asn Asp Arg Leu Ile Ala Ala Gly Lys Ser Pro Leu Gly Phe Leu Asn
                500                 505                 510

Pro Phe Leu Tyr Ser Lys Gly Val Ser Ala Leu Asn Asp Ile Thr Ser
        515                 520                 525

Gly Ser Asn Pro Gly Cys Arg Thr Asn Gly Phe Pro Ala Lys Glu Gly
        530                 535                 540

Trp Asp Pro Val Thr Gly Leu Gly Thr Pro Asp Phe Gln Lys Leu Ala
545                 550                 555                 560

Ser Ala Ala Gly Leu

<210> SEQ ID NO 27
<211> LENGTH: 363
<212> TYPE: PRT
<213> ORGANISM: Ganoderma lucidum

<400> SEQUENCE: 27

```
Ala Val Pro Ser Ser Cys Ser Ser Arg Ile Thr Pro Ala Cys Leu Gln
1               5                   10                  15

Ala Leu Tyr Asn Ile Pro Ser Asp Pro Ala Thr Gln Pro Ser Asn Lys
            20                  25                  30

Leu Ala Val Thr Gly Tyr Ile Glu Gln Tyr Ala Asn Gln Asp Asp Leu
        35                  40                  45

Ala Val Phe Leu Lys Glu Tyr Arg Ala Asp Met Ser Ser Asn Thr Thr
    50                  55                  60

Phe Thr Leu Gln Thr Leu Asp Gly Gly Val Asn Ser Gln Thr Asp Glu
65                  70                  75                  80

Ala Gly Ile Glu Ala Asn Leu Asp Val Gln Tyr Thr Val Gly Ile Ala
                85                  90                  95

Thr Gly Val Pro Thr Val Phe Ile Ser Val Gly Asp Gln Tyr Gln Asp
            100                 105                 110

Gly Asn Leu Glu Gly Phe Leu Asp Val Val Asn Phe Leu Leu Asp Glu
        115                 120                 125

Asp Thr Pro Pro Tyr Val Met Thr Thr Ser Tyr Gly Gln Asp Glu His
    130                 135                 140

Thr Met Ser Arg Lys Leu Ala Gln Asn Leu Cys Asn Ala Tyr Ala Gln
145                 150                 155                 160

Leu Gly Ala Arg Gly Val Ser Ile Leu Phe Ala Ser Gly Asp Gly Gly
                165                 170                 175

Val Ala Gly Ser Arg Ser Ser Cys Ser Lys Phe Val Pro Thr Phe Pro
            180                 185                 190

Pro Ser Gly Cys Pro Tyr Met Thr Ser Val Gly Ala Thr Gln Gly Val
        195                 200                 205

Pro Glu Thr Ala Ala Asp Phe Ser Ser Gly Gly Phe Ser Asn Tyr Phe
    210                 215                 220

Gly Ile Pro Asp Tyr Gln Ala Ser Ala Val Ser Gly Tyr Leu Ser Ala
225                 230                 235                 240

Leu Gly His Thr Asn Lys Gly Lys Tyr Asn Ala Ser Gly Arg Gly Phe
                245                 250                 255

Pro Asp Val Ser Thr Gln Gly Val Asn Phe Glu Val Met Val Asp Gly
            260                 265                 270

Ala Leu Glu Gly Val Ser Gly Thr Ser Ala Ala Ser Pro Thr Phe Ala
        275                 280                 285

Ala Val Val Ala Leu Leu Asn Asp Arg Leu Ile Ala Ala Gly Lys Ser
    290                 295                 300

Pro Leu Gly Phe Leu Asn Pro Phe Leu Tyr Ser Lys Gly Val Ser Ala
305                 310                 315                 320

Leu Asn Asp Ile Thr Ser Gly Ser Asn Pro Gly Cys Arg Thr Asn Gly
                325                 330                 335

Phe Pro Ala Lys Glu Gly Trp Asp Pro Val Thr Gly Leu Gly Thr Pro
            340                 345                 350

Asp Phe Gln Lys Leu Ala Ser Ala Ala Gly Leu
        355                 360
```

<210> SEQ ID NO 28
<211> LENGTH: 1698
<212> TYPE: DNA
<213> ORGANISM: Ganoderma lucidum

<400> SEQUENCE: 28

| | | | | | | |
|---|---|---|---|---|---|---|
| atggtcgcat | ccggcttgtt | gctcgcatcc | ctcgtcacac | tcgcgctcgg | aaagacggcc | 60 |
| actcggaacc | tcaaactcca | tgagacctcc | cagggagcac | cctcgggatt | ctcgttgacg | 120 |
| ggctccgcag | atccggatca | gacgctcaag | ctcaggttgg | cgctcgtgca | gggcaacgtc | 180 |
| gcagagctcg | agcgacgcct | ctacgatgtg | tccacgccct | cctcgcccaa | ctacggaaag | 240 |
| cacttgtcga | atcggaggt | ccagcagttg | gtcgcacctg | cgcaggactc | gatcgacgcg | 300 |
| atcaacgcat | ggttgaagga | aaacggcatc | tcggccaaga | caacctcggc | aacaggcgat | 360 |
| tggctctcgt | tcgaagtgcc | tgtgtcgaag | gcaaacgagc | tcttcgacgc | cgatttctcc | 420 |
| gtgtacaaac | accatgatac | aggcatggag | gtcgtccgca | cattgtccta | ctccattcct | 480 |
| gcggaactcc | aggcccattt | ggatctcgtc | catcccaccg | tcacattccc | caaccccaaa | 540 |
| ggacaccctc | ccgtgttcca | ggcacccgca | atgattacca | acgatgtgca | gaacttctcc | 600 |
| gcaggagcag | tcccgtcgtc | ctgttcctcg | cgcatcactc | ctgcgtgtct | ccaggcattg | 660 |
| tataacattc | cttccgatcc | tgcgacccag | ccttcgaaca | agctcgcagt | gactggctat | 720 |
| atcgaacagt | acgccaacca | ggacgacttg | gccgtcttct | tgaaggagta | tcgagccgac | 780 |
| atgtcgtcga | acacaaacctt | cactctccag | actctcgatg | gaggcgtgaa | ctcccagacg | 840 |
| gacgaagcag | gcatcgaagc | caacctcgac | gtgcagtaca | ccgtgggcat | cgcaacaggc | 900 |
| gtccccaccg | tgttcatctc | cgtgggcgat | cagtatcagg | acggtaacct | cgagggattc | 960 |
| ctcgatgtcg | tcaacttctt | gttggacgaa | gatactcctc | cttatgtgat | gacgacgtcc | 1020 |
| tacggccagg | atgaacatac | tatgtcccgg | aaattggcac | agaacttgtg | taacgcctat | 1080 |
| gcccagttgg | gagcacgagg | cgtgtccatc | ctcttcgcct | ccggagacgg | aggcgtcgca | 1140 |
| ggttcccgat | cgtcgtcgtg | ttcgaaattc | gtccccacgt | tcccgtccgg | ctgtccttac | 1200 |
| atgacttccg | tcggagcaac | acagggcgtg | cctgagactg | cagccgactt | ctcctcgggt | 1260 |
| ggtttctcga | actatttcgg | aattcccgac | taccaggcat | cggcagtgtc | gggatacttg | 1320 |
| tcggcccttgg | gccacacgaa | caagggcaag | tacaacgcat | cgggcagggg | cttcccggat | 1380 |
| gtctcgacac | agggcgtgaa | cttcgaagtg | atggtcgatg | gtgcattgga | aggagtgtcg | 1440 |
| ggtacttcgg | cagcatcccc | cacgttcgca | gcggtcgtcg | ccctcttgaa | cgatcgactc | 1500 |
| attgcagcag | gcaaatcccc | cttgggattc | ctcaaccct | tcttgtattc | caagggagtg | 1560 |
| tcggcattga | acgacatcac | atcgggttcc | aaccctggct | gtcggaccaa | cggcttccct | 1620 |
| gcgaaagagg | gctgggaccc | ggtcactgga | ttgggaacac | cggacttcca | gaaattggcc | 1680 |
| tcggcagcag | gcctctaa | | | | | 1698 |

<210> SEQ ID NO 29
<211> LENGTH: 2048
<212> TYPE: DNA
<213> ORGANISM: Neolentinus lepideus

<400> SEQUENCE: 29

| | | | | | | |
|---|---|---|---|---|---|---|
| atggttgcgc | tctctaccgc | ccttcttgcc | tcacttgtgg | ctctggcatg | cgcgggtccc | 60 |
| gctcctcgca | acctcgtcct | gcacgagtcg | cgcgatggag | tccccgaagg | cttcgtcaag | 120 |
| tcgagcaccg | cgtctcctga | cactacactc | aagctgcgta | ttgcccttgt | tcagggtgat | 180 |

```
atggccagcc ttgagaaggc actgtacgac gtcagcgtgc cttcaagccc gctctacggg    240
caacacctat cgaagcagga ggtatgccac atatgctcct gttctgaaga gttatgcagc    300
taattacttg ctgttaggtt gaggagtacg tgaagcccac gcaggagtcg gtagacgccg    360
taaaccagtg gctctcgtcc gaggggatta cggcgaacac catctcacct gccggcgact    420
ggctccaatt ttccgttcct gtcagcaagg cgaacgagat gtttgacgca gacttcagtg    480
tgttcaccca cactgagtct ggccagcaag ctatcaggac actctcctat tccattccca    540
aggagctcgt gggtcacctt gacctggtac accctaccat cacgtacgtt ccataatccc    600
aacctccttc ggactgaatg tatcactgac cctttcgttg tagtttcccc aacccgtact    660
cccacctgcc cgtggtctct tccccggcgc caggaacct cacgatcgat gcttctgttc     720
cctcatcctg tggctcgacg atcactccca cttgtctaca ggatctgtac ggcattccaa    780
ctactgccgc cacacagtca tccaacaagc tcgctgtctc tggtttcatt gatcagtatg    840
caaacaaagc tgacctcaag tccttcttga ccacgtaccg caaggacatt tcgtcttcga    900
cgacgtttac tctggagacc atcgatggtg gtgagaaccc ccaggacggg agcgatgctg    960
gtgtcgaagc tgtgagctgg ttttactttt gctctgtcaa atgaaatgcg attggtatga   1020
ctgactgacc gaatcataga accttgacac ccagtacact gtcggccttg ctaccggtgt   1080
cccgacctac ttcatctccg tcggagatga ctaccaggat ggtgaccttg aagggttctt   1140
ggacattgtc aactacctcc tcagcatgga ccagccgcag caagtcttga ccacctcgta   1200
cggccagaac gagaacacca tgtccagatc cttggcgaag tatgtagtaa agagattgtt   1260
accgggattc gcgactaaag attcgattgc agcaatcttt gtaatgctta catgcagctt   1320
ggcgctcgcg gcacctccat cctgtttgcc tctggtgacg tggtgtctc tggctcacag    1380 tccggcagct gcggcagcaa gttcgtgccc acattcccct ctggatgccc ctagtaagac   1440
cttccccctc tcatcctcct ttcgattact aacatatcgt actcagcctg acctccgttg   1500
gtgcaacgac cggcatcaac ccggaggtcg cagcctcctt ctcctcgggc gggttcagca   1560
actactgggg tgtgccatcg taccagcagt ccgttgtttc ttcgtacatc agcggcctag   1620
gctcgacgaa caagggcaag tataacagct ccggccgtgg gttccccgat gtctccgcgc   1680
agggcgagaa cgtcgaaatt gtcgtcgacg gttcaactga gggggtagat ggaacgagct   1740
gctcgagccc catctttgcc agtatcgttt cgcttctgaa cgacgagctg attgcagccg   1800
ggaagagccc gcttgggttc ttgaaccct tcttgtactc tgatggcgcc tcggctttca    1860
atgatattac ttctggtgag cgtcgctgtt tgagagtgaa gtttatggat gctgatctac   1920
tttcgaaata cttaggtgac aatccaggct gcaacaccaa tggtttctct gcgaaatcag   1980
gctgggaccc cgtcaccggt cttggtactc ccaactacgc aaaactgagg accgctgtcg   2040
gcttctga                                                            2048
```

<210> SEQ ID NO 30
<211> LENGTH: 565
<212> TYPE: PRT
<213> ORGANISM: Neolentinus lepideus

<400> SEQUENCE: 30

Met Val Ala Leu Ser Thr Ala Leu Leu Ala Ser Leu Val Ala Leu Ala
1               5                   10                  15

Cys Ala Gly Pro Ala Pro Arg Asn Leu Val Leu His Glu Ser Arg Asp
            20                  25                  30

```
Gly Val Pro Glu Gly Phe Val Lys Ser Ser Thr Ala Ser Pro Asp Thr
             35                  40                  45

Thr Leu Lys Leu Arg Ile Ala Leu Val Gln Gly Asp Met Ala Ser Leu
 50                  55                  60

Glu Lys Ala Leu Tyr Asp Val Ser Val Pro Ser Ser Pro Leu Tyr Gly
 65                  70                  75                  80

Gln His Leu Ser Lys Gln Glu Val Glu Tyr Val Lys Pro Thr Gln
                 85                  90                  95

Glu Ser Val Asp Ala Val Asn Gln Trp Leu Ser Ser Glu Gly Ile Thr
                100                 105                 110

Ala Asn Thr Ile Ser Pro Ala Gly Asp Trp Leu Gln Phe Ser Val Pro
                115                 120                 125

Val Ser Lys Ala Asn Glu Met Phe Asp Ala Asp Phe Ser Val Phe Thr
130                 135                 140

His Thr Glu Ser Gly Gln Gln Ala Ile Arg Thr Leu Ser Tyr Ser Ile
145                 150                 155                 160

Pro Lys Glu Leu Val Gly His Leu Asp Leu Val His Pro Thr Ile Thr
                165                 170                 175

Phe Pro Asn Pro Tyr Ser His Leu Pro Val Val Ser Ser Pro Ala Pro
                180                 185                 190

Arg Asn Leu Thr Ile Asp Ala Ser Val Pro Ser Ser Cys Gly Ser Thr
                195                 200                 205

Ile Thr Pro Thr Cys Leu Gln Asp Leu Tyr Gly Ile Pro Thr Thr Ala
                210                 215                 220

Ala Thr Gln Ser Ser Asn Lys Leu Ala Val Ser Gly Phe Ile Asp Gln
225                 230                 235                 240

Tyr Ala Asn Lys Ala Asp Leu Lys Ser Phe Leu Thr Thr Tyr Arg Lys
                245                 250                 255

Asp Ile Ser Ser Ser Thr Thr Phe Thr Leu Glu Thr Ile Asp Gly Gly
                260                 265                 270

Glu Asn Pro Gln Asp Gly Ser Asp Ala Gly Val Glu Ala Asn Leu Asp
                275                 280                 285

Thr Gln Tyr Thr Val Gly Leu Ala Thr Gly Val Pro Thr Tyr Phe Ile
                290                 295                 300

Ser Val Gly Asp Asp Tyr Gln Asp Gly Asp Leu Glu Gly Phe Leu Asp
305                 310                 315                 320

Ile Val Asn Tyr Leu Leu Ser Met Asp Gln Pro Gln Val Leu Thr
                325                 330                 335

Thr Ser Tyr Gly Gln Asn Glu Asn Thr Met Ser Arg Ser Leu Ala Asn
                340                 345                 350

Asn Leu Cys Asn Ala Tyr Met Gln Leu Gly Ala Arg Gly Thr Ser Ile
                355                 360                 365

Leu Phe Ala Ser Gly Asp Gly Val Ser Gly Ser Gln Ser Gly Ser
                370                 375                 380

Cys Gly Ser Lys Phe Val Pro Thr Phe Pro Ser Gly Cys Pro Tyr Leu
385                 390                 395                 400

Thr Ser Val Gly Ala Thr Thr Gly Ile Asn Pro Glu Val Ala Ala Ser
                405                 410                 415

Phe Ser Ser Gly Gly Phe Ser Asn Tyr Trp Gly Val Pro Ser Tyr Gln
                420                 425                 430

Gln Ser Val Val Ser Ser Tyr Ile Ser Gly Leu Gly Ser Thr Asn Lys
                435                 440                 445

Gly Lys Tyr Asn Ser Ser Gly Arg Gly Phe Pro Asp Val Ser Ala Gln
```

```
            450                 455                 460
Gly Glu Asn Val Glu Ile Val Asp Gly Ser Thr Glu Gly Val Asp
465                 470                 475                 480

Gly Thr Ser Cys Ser Ser Pro Ile Phe Ala Ser Ile Val Ser Leu Leu
                    485                 490                 495

Asn Asp Glu Leu Ile Ala Ala Gly Lys Ser Pro Leu Gly Phe Leu Asn
                500                 505                 510

Pro Phe Leu Tyr Ser Asp Gly Ala Ser Ala Phe Asn Asp Ile Thr Ser
            515                 520                 525

Gly Asp Asn Pro Gly Cys Asn Thr Asn Gly Phe Ser Ala Lys Ser Gly
        530                 535                 540

Trp Asp Pro Val Thr Gly Leu Gly Thr Pro Asn Tyr Ala Lys Leu Arg
545                 550                 555                 560

Thr Ala Val Gly Phe
                565

<210> SEQ ID NO 31
<211> LENGTH: 367
<212> TYPE: PRT
<213> ORGANISM: Neolentinus lepideus

<400> SEQUENCE: 31

Ala Ser Val Pro Ser Ser Cys Gly Ser Thr Ile Thr Pro Thr Cys Leu
1               5                   10                  15

Gln Asp Leu Tyr Gly Ile Pro Thr Thr Ala Thr Gln Ser Ser Asn
            20                  25                  30

Lys Leu Ala Val Ser Gly Phe Ile Asp Gln Tyr Ala Asn Lys Ala Asp
        35                  40                  45

Leu Lys Ser Phe Leu Thr Thr Tyr Arg Lys Asp Ile Ser Ser Ser Thr
50                  55                  60

Thr Phe Thr Leu Glu Thr Ile Asp Gly Gly Glu Asn Pro Gln Asp Gly
65                  70                  75                  80

Ser Asp Ala Gly Val Glu Ala Asn Leu Asp Thr Gln Tyr Thr Val Gly
                85                  90                  95

Leu Ala Thr Gly Val Pro Thr Tyr Phe Ile Ser Val Gly Asp Asp Tyr
            100                 105                 110

Gln Asp Gly Asp Leu Glu Gly Phe Leu Asp Ile Val Asn Tyr Leu Leu
        115                 120                 125

Ser Met Asp Gln Pro Gln Gln Val Leu Thr Thr Ser Tyr Gly Gln Asn
130                 135                 140

Glu Asn Thr Met Ser Arg Ser Leu Ala Asn Asn Leu Cys Asn Ala Tyr
145                 150                 155                 160

Met Gln Leu Gly Ala Arg Gly Thr Ser Ile Leu Phe Ala Ser Gly Asp
                165                 170                 175

Gly Gly Val Ser Gly Ser Gln Ser Gly Ser Cys Gly Ser Lys Phe Val
            180                 185                 190

Pro Thr Phe Pro Ser Gly Cys Pro Tyr Leu Thr Ser Val Gly Ala Thr
        195                 200                 205

Thr Gly Ile Asn Pro Glu Val Ala Ala Ser Phe Ser Ser Gly Gly Phe
210                 215                 220

Ser Asn Tyr Trp Gly Val Pro Ser Tyr Gln Gln Ser Val Val Ser Ser
225                 230                 235                 240

Tyr Ile Ser Gly Leu Gly Ser Thr Asn Lys Gly Lys Tyr Asn Ser Ser
                245                 250                 255
```

```
Gly Arg Gly Phe Pro Asp Val Ser Ala Gln Gly Glu Asn Val Glu Ile
            260                 265                 270

Val Val Asp Gly Ser Thr Glu Gly Val Asp Gly Thr Ser Cys Ser Ser
            275                 280                 285

Pro Ile Phe Ala Ser Ile Val Ser Leu Leu Asn Asp Glu Leu Ile Ala
            290                 295                 300

Ala Gly Lys Ser Pro Leu Gly Phe Leu Asn Pro Phe Leu Tyr Ser Asp
305                 310                 315                 320

Gly Ala Ser Ala Phe Asn Asp Ile Thr Ser Gly Asp Asn Pro Gly Cys
                325                 330                 335

Asn Thr Asn Gly Phe Ser Ala Lys Ser Gly Trp Asp Pro Val Thr Gly
            340                 345                 350

Leu Gly Thr Pro Asn Tyr Ala Lys Leu Arg Thr Ala Val Gly Phe
            355                 360                 365

<210> SEQ ID NO 32
<211> LENGTH: 1698
<212> TYPE: DNA
<213> ORGANISM: Neolentinus lepideus

<400> SEQUENCE: 32
atggtggccc tctcgacagc cttgttggca tcgctcgtcg cactcgcatg tgcaggccct      60
gcacctcgaa acttggtcct ccatgaatcc agggatggcg tccctgaagg tttcgtgaag     120
tcctccacgg cctcccctga taccacattg aaattgagga tcgcgctcgt ccagggagat     180
atggcgtccc tcgaaaaggc gctctatgac gtgtcggtcc cgtcctcgcc tctctatggc     240
cagcacctct cgaagcagga ggtcgaagag tacgtcaagc ctactcagga atccgtcgac     300
gccgtgaacc agtggctctc ctccgaaggc attacagcga acactatttc gcctgcagga     360
gactggctcc agttctcggt gcccgtctcg aaggcgaacg agatgttcga cgccgacttc     420
tccgtcttca cccacaccga gtcgggacag caggccatcc ggacattgtc gtattccatt     480
cctaaggagc tcgtcggtca tctcgacttg gtccatccta ctatcacttt ccccaacccg     540
tactcgcatc tccctgtcgt ctcgtccccc gccctagga acttgacgat tgatgcgtcc     600
gtgccttcct cgtgtggatc gactatcaca cctacgtgtt tgcaggatct ctacggtatc     660
ccgactacag cagccactca gtcctccaac aagttggccg tgtcgggctt catcgatcag     720
tacgccaaca aggcagactt gaaatccttc ctcacaacct accggaagga tatctcctcc     780
tccacaacct tcaccctcga gaccatcgat ggtggcgaaa accgcagga tggctcggat     840 gcaggcgtcg aagccaactt ggatacacag tacaccgtgg gtttggcaac tggcgtcccc     900
acctatttca tctcggtcgg tgatgactac caggatggcg acctcgaagg tttcctcgat     960
attgtcaact acttgttgtc catggaccag ccccagcagg tcctcacgac gtcgtatggt    1020
cagaacgaaa acacaatgtc gcggtcgttg gcgaacaacc tctgtaacgc atacatgcag    1080
ctcggagcac gaggcacctc catcctcttc gcgtccggag atggaggcgt tcgggctcc    1140 cagtccggct cctgtggttc gaaattcgtc cccacattcc cctccggatg tccttacttg    1200
acatcggtcg gtgcaacaac cggcatcaac ccggaggtgg cagcatcgtt ctcgtccggt    1260
ggcttctcca actattgggg tgtgccctcc tatcagcagt cggtggtctc gtcgtacatc    1320
tccggactcg gctccaccaa caagggcaaa tacaactcct cgggcagggg cttcccggat    1380
gtgtccgcac agggcgaaaa cgtcgagatc gtggtcgacg gctccacaga gggcgtggac    1440
ggcacgtcgt gttcgtcccc catcttcgca tccatcgtct cgctcctcaa cgacgagctc    1500
```

```
attgcggcag gcaaatcccc gttgggcttc ttgaacccgt tcctctactc cgatggcgca    1560
tcggcattca acgacatcac ttcgggagat aaccctggat gtaacaccaa cggattctcc    1620
gccaagtcgg gctgggaccc ggtgacaggt ctcggcactc ccaactacgc caagctcagg    1680
actgccgtcg gcttctaa                                                  1698

<210> SEQ ID NO 33
<211> LENGTH: 2317
<212> TYPE: DNA
<213> ORGANISM: Bacillus sp-19138

<400> SEQUENCE: 33
aagcacagcg catgtgatta accaaagaa atcaagatta aatatgaaaa acagcaactc      60
tattgatttt cacactcaga tcaagtataa ttccgacaag agaatacacg aaagattcag     120
cctaaacaga aaatatatac tccgcaatct tttgtggatc cgaaatttgc aagttccaga    180
aaaaaaggag cttttcaaa atgaaaaaat taagtaaaaa attgcttgcc gtagctgcgg     240
caggtacgct gttgcttgca accgtgccaa gcattgcctt tgcagacact gcgcaagaaa    300
tcccccaagg cgtaggttcc ggtgtgctgt ccaacgtcga ctatttcggt ggtctcgatc    360
caagcactgt ggtaacggtt gatatcgtca tgaaaatcca aaacaaatac gacttggcca    420
actacatcaa ggaaacgacc tctccgggta gcaacaccta ccataaatac ctgacaccga    480
cgcaattcaa agccaaatac gcaccttctc cagcgagcgt caatgcgatt actcactatc    540
tctcgtccta tggcatcacg tcttccgttt acccggacaa cctgatcatc acagcgaccg    600
gcaccgtcgg tcaattcaac aacgcgttca cgtcaccat tgaacgtgcc caatacaaag    660
gcaagagctt ccatgcatcc aaaaccaacc ctaaagcacc ggctgccatc gccgactcca    720
tcctgtgcat tttgggcatc agcaactact ccaacttcac ttcgcacatt gcgaaacagc    780
agccgctcga cagcagccaa tccacagcga acgtcacgcc gaacccgacc ggccgcatga    840
ccaacgactt ggtgtcccgt tacaacgtac aacccttgta caccaaagga gccaacggtt    900
ccggtcaaac gatcggcatc gtgacgctgg ctgatttcaa cccgagtgat gcctactcgt    960
actggcagta caacaacatc aacgtcaacc cgaaccgcat caccaaaatc aacgtggacg   1020
gtggttccgg cctgagtgaa gatgccggtt cagacgaaac atcgctcgac gtggaacaat   1080
ccggagctct ggcaccgggc gcaaacctca atgtctatgt cggcccgaac accgatacag   1140
ggtttgtgga tgcgtacgca aaagcgatca acgacaacgt cgcacaccag atctccgcaa   1200
gctggggcga atccgaatcg ctgattaatt actacgtcca acagcaaatg gaaacacctg   1260
agtatgcgga acattcaac caactcttca tgcaagcagc ggcacaggga acttcgatgt   1320
tcgcgtcggc tggtgactcc ggtgcctatg atgcttccgg tgacctcaac acgtacgatc   1380
tctccgtcga caatccggct gacagcccgt acatcacggc ggccggcggc accaccgtgc   1440
cgtttaccta tacgtcgacg caatacaacc tgtcgattac cgtaccgcaa gaacgcgcat   1500
ggggctggga ttatctctac ccgctgtttg acgcacgcgg cttgaacaac ccgaccggct   1560
gggcacaacg ttactttgtc ggcggcggcg gcggtttcag ccaactcttc gcaacacctg   1620
actaccaaac cggcgtatcc ggcgtgaaca gctacaccgc tgtccaccaa tggactccga   1680
gttccgactt cacctcggtc actcgtgacg cacaaccgac catcgtcacc ggcacaggca   1740
ccggccgtaa cctgcctgac ctgtcgatga cgccgacccc gtacaccggc tactccgtgt   1800
acttcaactt gccgaccacg aacgtgcgca cgacagtaga ctccggctgg gcaacgtacg   1860
gcggtacttc ctttgtagca ccgcaattgg caggtctcag cgcgttgatc aacagtgcaa   1920
```

```
acggcagcga agcaggcttc tggaaccctc agctctaccg ttttgcacaa agcaatcact      1980
cgccgttgca cccgctcaac accgcaggcg catccaacga caacgtcttc tattccggca      2040
ctccgggcgc catctacaac caagcaaccg tcttggcac gcccgacgtg acggcacttg       2100
cacaagcgtt tggcaaataa gttcttttgc tccccttac acaaaccaaa gaccactcga       2160
ctcccgagtg gtctttggtt tgatgctcag cgactgtagt tcacgttgat tctgccattc      2220
ttgctgatca agcggatggg aatttctccc gttccacca ctataagtca actggttttg       2280
caacccggat gtgacaactg gcaacacatc tccgcga                              2317
```

<210> SEQ ID NO 34
<211> LENGTH: 639
<212> TYPE: PRT
<213> ORGANISM: Bacillus sp. 19138

<400> SEQUENCE: 34

```
Met Lys Lys Leu Ser Lys Lys Leu Leu Ala Val Ala Ala Ala Gly Thr
1               5                   10                  15

Leu Leu Leu Ala Thr Val Pro Ser Ile Ala Phe Ala Asp Thr Ala Gln
                20                  25                  30

Glu Ile Pro Gln Gly Val Gly Ser Gly Val Leu Ser Asn Val Asp Tyr
            35                  40                  45

Phe Gly Gly Leu Asp Pro Ser Thr Val Val Thr Val Asp Ile Val Met
        50                  55                  60

Lys Ile Gln Asn Lys Tyr Asp Leu Ala Asn Tyr Ile Lys Glu Thr Thr
65                  70                  75                  80

Ser Pro Gly Ser Asn Thr Tyr His Lys Tyr Leu Thr Pro Thr Gln Phe
                85                  90                  95

Lys Ala Lys Tyr Ala Pro Ser Pro Ala Ser Val Asn Ala Ile Thr His
            100                 105                 110

Tyr Leu Ser Ser Tyr Gly Ile Thr Ser Ser Val Tyr Pro Asp Asn Leu
        115                 120                 125

Ile Ile Thr Ala Thr Gly Thr Val Gly Gln Phe Asn Asn Ala Phe Asn
130                 135                 140

Val Thr Ile Glu Arg Ala Gln Tyr Lys Gly Lys Ser Phe His Ala Ser
145                 150                 155                 160

Lys Thr Asn Pro Lys Ala Pro Ala Ala Ile Ala Asp Ser Ile Leu Cys
                165                 170                 175

Ile Leu Gly Ile Ser Asn Tyr Ser Asn Phe Thr Ser His Ile Ala Lys
            180                 185                 190

Gln Gln Pro Leu Asp Ser Ser Gln Ser Thr Ala Asn Val Thr Pro Asn
        195                 200                 205

Pro Thr Gly Arg Met Thr Asn Asp Leu Val Ser Arg Tyr Asn Val Gln
    210                 215                 220

Pro Leu Tyr Thr Lys Gly Ala Asn Gly Ser Gly Gln Thr Ile Gly Ile
225                 230                 235                 240

Val Thr Leu Ala Asp Phe Asn Pro Ser Asp Ala Tyr Ser Tyr Trp Gln
                245                 250                 255

Tyr Asn Asn Ile Asn Val Asn Pro Asn Arg Ile Thr Lys Ile Asn Val
            260                 265                 270

Asp Gly Gly Ser Gly Leu Ser Glu Asp Ala Gly Ser Asp Glu Thr Ser
        275                 280                 285

Leu Asp Val Glu Gln Ser Gly Ala Leu Ala Pro Gly Ala Asn Leu Asn
    290                 295                 300
```

```
Val Tyr Val Gly Pro Asn Thr Asp Thr Gly Phe Val Asp Ala Tyr Ala
305                 310                 315                 320

Lys Ala Ile Asn Asp Asn Val Ala His Gln Ile Ser Ala Ser Trp Gly
            325                 330                 335

Glu Ser Glu Ser Leu Ile Asn Tyr Tyr Val Gln Gln Met Glu Thr
        340                 345                 350

Pro Glu Tyr Ala Glu Thr Phe Asn Gln Leu Phe Met Gln Ala Ala
        355                 360                 365

Gln Gly Thr Ser Met Phe Ala Ser Ala Gly Asp Ser Gly Ala Tyr Asp
    370                 375                 380

Ala Ser Gly Asp Leu Asn Thr Tyr Asp Leu Ser Val Asp Asn Pro Ala
385                 390                 395                 400

Asp Ser Pro Tyr Ile Thr Ala Ala Gly Gly Thr Thr Val Pro Phe Thr
                405                 410                 415

Tyr Thr Ser Thr Gln Tyr Asn Leu Ser Ile Thr Val Pro Gln Glu Arg
                420                 425                 430

Ala Trp Gly Trp Asp Tyr Leu Tyr Pro Leu Phe Asp Ala Arg Gly Leu
            435                 440                 445

Asn Asn Pro Thr Gly Trp Ala Gln Arg Tyr Phe Val Gly Gly Gly Gly
450                 455                 460

Gly Phe Ser Gln Leu Phe Ala Thr Pro Asp Tyr Gln Thr Gly Val Ser
465                 470                 475                 480

Gly Val Asn Ser Tyr Thr Ala Val His Gln Trp Pro Ser Ser Asp
                485                 490                 495

Phe Thr Ser Val Thr Arg Asp Ala Gln Pro Thr Ile Val Thr Gly Thr
                500                 505                 510

Gly Thr Gly Arg Asn Leu Pro Asp Leu Ser Met Asn Ala Asp Pro Tyr
            515                 520                 525

Thr Gly Tyr Ser Val Tyr Phe Asn Leu Pro Thr Thr Asn Gly Ala Thr
530                 535                 540

Thr Val Asp Ser Gly Trp Ala Thr Tyr Gly Gly Thr Ser Phe Val Ala
545                 550                 555                 560

Pro Gln Leu Ala Gly Leu Ser Ala Leu Ile Asn Ser Ala Asn Gly Ser
                565                 570                 575

Glu Ala Gly Phe Trp Asn Pro Gln Leu Tyr Arg Phe Ala Gln Ser Asn
            580                 585                 590

His Ser Pro Leu His Pro Leu Asn Thr Ala Gly Ala Ser Asn Asp Asn
            595                 600                 605

Val Phe Tyr Ser Gly Thr Pro Gly Ala Ile Tyr Asn Gln Ala Thr Gly
            610                 615                 620

Leu Gly Thr Pro Asp Val Thr Ala Leu Ala Gln Ala Phe Gly Lys
625                 630                 635

<210> SEQ ID NO 35
<211> LENGTH: 431
<212> TYPE: PRT
<213> ORGANISM: Bacillus sp. 19138

<400> SEQUENCE: 35

Pro Thr Gly Arg Met Thr Asn Asp Leu Val Ser Arg Tyr Asn Val Gln
1               5                   10                  15

Pro Leu Tyr Thr Lys Gly Ala Asn Gly Ser Gly Gln Thr Ile Gly Ile
            20                  25                  30

Val Thr Leu Ala Asp Phe Asn Pro Ser Asp Ala Tyr Ser Tyr Trp Gln
```

```
              35                  40                  45
Tyr Asn Asn Ile Asn Val Asn Pro Asn Arg Ile Thr Lys Ile Asn Val
 50                  55                  60

Asp Gly Gly Ser Gly Leu Ser Glu Asp Ala Gly Ser Asp Glu Thr Ser
 65                  70                  75                  80

Leu Asp Val Glu Gln Ser Gly Ala Leu Ala Pro Gly Ala Asn Leu Asn
                 85                  90                  95

Val Tyr Val Gly Pro Asn Thr Asp Thr Gly Phe Val Asp Ala Tyr Ala
                100                 105                 110

Lys Ala Ile Asn Asp Asn Val Ala His Gln Ile Ser Ala Ser Trp Gly
                115                 120                 125

Glu Ser Glu Ser Leu Ile Asn Tyr Tyr Val Gln Gln Gln Met Glu Thr
                130                 135                 140

Pro Glu Tyr Ala Glu Thr Phe Asn Gln Leu Phe Met Gln Ala Ala Ala
145                 150                 155                 160

Gln Gly Thr Ser Met Phe Ala Ser Ala Gly Asp Ser Gly Ala Tyr Asp
                165                 170                 175

Ala Ser Gly Asp Leu Asn Thr Tyr Asp Leu Ser Val Asp Asn Pro Ala
                180                 185                 190

Asp Ser Pro Tyr Ile Thr Ala Ala Gly Gly Thr Thr Val Pro Phe Thr
                195                 200                 205

Tyr Thr Ser Thr Gln Tyr Asn Leu Ser Ile Thr Val Pro Gln Glu Arg
210                 215                 220

Ala Trp Gly Trp Asp Tyr Leu Tyr Pro Leu Phe Asp Ala Arg Gly Leu
225                 230                 235                 240

Asn Asn Pro Thr Gly Trp Ala Gln Arg Tyr Phe Val Gly Gly Gly Gly
                245                 250                 255

Gly Phe Ser Gln Leu Phe Ala Thr Pro Asp Tyr Gln Thr Gly Val Ser
                260                 265                 270

Gly Val Asn Ser Tyr Thr Ala Val His Gln Trp Thr Pro Ser Ser Asp
                275                 280                 285

Phe Thr Ser Val Thr Arg Asp Ala Gln Pro Thr Ile Val Thr Gly Thr
290                 295                 300

Gly Thr Gly Arg Asn Leu Pro Asp Leu Ser Met Asn Ala Asp Pro Tyr
305                 310                 315                 320

Thr Gly Tyr Ser Val Tyr Phe Asn Leu Pro Thr Thr Asn Gly Ala Thr
                325                 330                 335

Thr Val Asp Ser Gly Trp Ala Thr Tyr Gly Gly Thr Ser Phe Val Ala
                340                 345                 350

Pro Gln Leu Ala Gly Leu Ser Ala Leu Ile Asn Ser Ala Asn Gly Ser
                355                 360                 365

Glu Ala Gly Phe Trp Asn Pro Gln Leu Tyr Arg Phe Ala Gln Ser Asn
                370                 375                 380

His Ser Pro Leu His Pro Leu Asn Thr Ala Gly Ala Ser Asn Asp Asn
385                 390                 395                 400

Val Phe Tyr Ser Gly Thr Pro Gly Ala Ile Tyr Asn Gln Ala Thr Gly
                405                 410                 415

Leu Gly Thr Pro Asp Val Thr Ala Leu Ala Gln Ala Phe Gly Lys
                420                 425                 430

<210> SEQ ID NO 36
<211> LENGTH: 177
<212> TYPE: PRT
<213> ORGANISM: Thermoascus aurantiacus
```

<400> SEQUENCE: 36

```
Thr Arg Ile Ser Ser Cys Ser Gly Ser Arg Gln Ser Ala Leu Thr Thr
1               5                   10                  15

Ala Leu Arg Asn Ala Ala Ser Leu Ala Asn Ala Ala Asp Ala Ala
            20                  25                  30

Gln Ser Gly Ser Ala Ser Lys Phe Ser Glu Tyr Phe Lys Thr Thr Ser
        35                  40                  45

Ser Ser Thr Arg Gln Thr Val Ala Ala Arg Leu Arg Ala Val Ala Arg
    50                  55                  60

Glu Ala Ser Ser Ser Ser Gly Ala Thr Thr Tyr Tyr Cys Asp Asp
65                  70                  75                  80

Pro Tyr Gly Tyr Cys Ser Ser Asn Val Leu Ala Tyr Thr Leu Pro Ser
                85                  90                  95

Tyr Asn Ile Ile Ala Asn Cys Asp Ile Phe Tyr Thr Tyr Leu Pro Ala
            100                 105                 110

Leu Thr Ser Thr Cys His Ala Gln Asp Gln Ala Thr Thr Ala Leu His
            115                 120                 125

Glu Phe Thr His Ala Pro Gly Val Tyr Ser Pro Gly Thr Asp Asp Leu
130                 135                 140

Ala Tyr Gly Tyr Gln Ala Ala Met Gly Leu Ser Ser Gln Ala Val
145                 150                 155                 160

Met Asn Ala Asp Thr Tyr Ala Leu Tyr Ala Asn Ala Ile Tyr Leu Gly
                165                 170                 175

Cys
```

<210> SEQ ID NO 37
<211> LENGTH: 412
<212> TYPE: PRT
<213> ORGANISM: Pyrococcus furiosus

<400> SEQUENCE: 37

```
Ala Glu Leu Glu Gly Leu Asp Glu Ser Ala Ala Gln Val Met Ala Thr
1               5                   10                  15

Tyr Val Trp Asn Leu Gly Tyr Asp Gly Ser Gly Ile Thr Ile Gly Ile
            20                  25                  30

Ile Asp Thr Gly Ile Asp Ala Ser His Pro Asp Leu Gln Gly Lys Val
        35                  40                  45

Ile Gly Trp Val Asp Phe Val Asn Gly Arg Ser Tyr Pro Tyr Asp Asp
    50                  55                  60

His Gly His Gly Thr His Val Ala Ser Ile Ala Ala Gly Thr Gly Ala
65                  70                  75                  80

Ala Ser Asn Gly Lys Tyr Lys Gly Met Ala Pro Gly Ala Lys Leu Ala
                85                  90                  95

Gly Ile Lys Val Leu Gly Ala Asp Gly Ser Gly Ser Ile Ser Thr Ile
            100                 105                 110

Ile Lys Gly Val Glu Trp Ala Val Asp Asn Lys Asp Lys Tyr Gly Ile
            115                 120                 125

Lys Val Ile Asn Leu Ser Leu Gly Ser Ser Gln Ser Ser Asp Gly Thr
        130                 135                 140

Asp Ala Leu Ser Gln Ala Val Asn Ala Ala Trp Asp Ala Gly Leu Val
145                 150                 155                 160

Val Val Val Ala Ala Gly Asn Ser Gly Pro Asn Lys Tyr Thr Ile Gly
                165                 170                 175
```

```
Ser Pro Ala Ala Ala Ser Lys Val Ile Thr Val Gly Ala Val Asp Lys
            180                 185                 190

Tyr Asp Val Ile Thr Ser Phe Ser Ser Arg Gly Pro Thr Ala Asp Gly
                195                 200                 205

Arg Leu Lys Pro Glu Val Val Ala Pro Gly Asn Trp Ile Ile Ala Ala
        210                 215                 220

Arg Ala Ser Gly Thr Ser Met Gly Gln Pro Ile Asn Asp Tyr Tyr Thr
225                 230                 235                 240

Ala Ala Pro Gly Thr Ser Met Ala Thr Pro His Val Ala Gly Ile Ala
                245                 250                 255

Ala Leu Leu Leu Gln Ala His Pro Ser Trp Thr Pro Asp Lys Val Lys
            260                 265                 270

Thr Ala Leu Ile Glu Thr Ala Asp Ile Val Lys Pro Asp Glu Ile Ala
        275                 280                 285

Asp Ile Ala Tyr Gly Ala Gly Arg Val Asn Ala Tyr Lys Ala Ile Asn
        290                 295                 300

Tyr Asp Asn Tyr Ala Lys Leu Val Phe Thr Gly Tyr Val Ala Asn Lys
305                 310                 315                 320

Gly Ser Gln Thr His Gln Phe Val Ile Ser Gly Ala Ser Phe Val Thr
                325                 330                 335

Ala Thr Leu Tyr Trp Asp Asn Ala Asn Ser Asp Leu Asp Leu Tyr Leu
            340                 345                 350

Tyr Asp Pro Asn Gly Asn Gln Val Asp Tyr Ser Tyr Thr Ala Tyr Tyr
        355                 360                 365

Asp Phe Glu Lys Val Gly Tyr Tyr Asn Pro Thr Asp Gly Thr Trp Thr
        370                 375                 380

Ile Lys Val Val Ser Tyr Ser Gly Ser Ala Asn Tyr Gln Val Asp Val
385                 390                 395                 400

Val Ser Asp Gly Ser Leu Ser Gln Pro Gly Ser Ser
                405                 410

<210> SEQ ID NO 38
<211> LENGTH: 560
<212> TYPE: PRT
<213> ORGANISM: Lecanicillium sp. WMM742

<400> SEQUENCE: 38

Met Val Ser Phe Ser Lys Ile Cys Phe Ala Ala Val Ser Ala Gly Ser
1               5                   10                  15

Val Leu Ala Ala Pro Ala Pro His Gly Pro Leu Val Lys Phe Gly Glu
            20                  25                  30

Ile Thr Lys Leu Pro Ser Lys Trp Ile Ala Thr Gly Ala Ala Asp Ser
        35                  40                  45

Asp Ala Val Ile Lys Ala Gln Ile Gly Ile Lys Gln Asn Asn Ile Lys
    50                  55                  60

Gly Leu Gln Asp Lys Leu Ala Asp Ile Ala Asp Pro Asn Ser Pro Asn
65                  70                  75                  80

Tyr Gly Gln Trp Leu Ser Lys Glu Val Asp Lys Tyr Ser Ala Pro
                85                  90                  95

Ala Ala Ala Asp Val Ala Val Lys Ala Trp Leu Ala Ser Ser Gly
                100                 105                 110

Ile Thr Asp Val Thr Met Pro Thr Asn Asp Trp Ile Glu Phe Ser Val
            115                 120                 125

Pro Val Ser Lys Met Glu Ser Leu Leu Gly Ser Lys Tyr Glu Trp Phe
        130                 135                 140
```

```
Val His Leu Glu Thr Gly Glu Lys Val Pro Arg Thr Lys Gln Phe Ser
145                 150                 155                 160

Val Pro Gln Asn Leu His Asp Leu Ile Asp Val Val Thr Pro Thr Thr
            165                 170                 175

Val Leu Tyr His Asn Met Gly Pro His Ala His Ala Ser Pro Gln Ala
            180                 185                 190

Ala Asp Ala Ser Gly Leu Thr Ser Pro Ala Ser Ile Lys Ser Ala Tyr
            195                 200                 205

Asn Val Asp Tyr Lys Gly Thr Gly Asn Thr Leu Val Gly Thr Thr Gly
            210                 215                 220

Phe Leu Gly Val Gly Ala Ser His Gln Asp Tyr Ala Asn Phe Ala Arg
225                 230                 235                 240

Gln Phe Ser Pro Gly Leu Thr Asp Phe Lys Asp Val Ser Ile Asn Gly
            245                 250                 255

Gly Ser Asn Ser Gly Asp Gly Ser Ala Leu Glu Gly Asn Leu Asp Thr
            260                 265                 270

Gln Tyr Cys Gly Ala Leu Ala Ala Pro Asn Pro Ser Glu Tyr Leu Ala
            275                 280                 285

His Ala Pro Glu Gly Ser Asp Gly Ser Ser Phe Asn Asp Ala Met Leu
            290                 295                 300

Ala Phe Gly Asn Tyr Leu Asn Ala Asn Ser Asn Pro Pro Ser Ala Val
305                 310                 315                 320

Ser Thr Ser Tyr Gly Gly Glu Glu Asp Gly Thr Asp Pro Asn Tyr Met
            325                 330                 335

Asp Arg Ile Cys Asn Glu Phe Met Lys Ala Gly Ser Arg Gly Val Ser
            340                 345                 350

Ile Phe Phe Ser Ser Gly Asp Asn Gly Val Gly Gly Asn Gly Glu Ser
            355                 360                 365

Ser Cys Tyr Asn Gly Tyr Tyr Pro Leu Trp Pro Ala Ser Cys Pro Tyr
370                 375                 380

Val Thr Thr Val Gly Gly Thr Glu Phe Asp Gly Ser Gly Arg Glu Val
385                 390                 395                 400

Val Ala Asn Phe Glu Gln Tyr Asn Lys Asn Val Lys Ser Pro Gly Gly
            405                 410                 415

Gly Phe Ser Asn His Phe Pro Ala Pro Ser Tyr Asn Lys Asn Val Thr
            420                 425                 430

Thr Ala Tyr Ala Asn Ser Leu Ser Ala Ala Gln Lys Gln Arg Leu Asn
            435                 440                 445

Pro Asn Gly Arg Gly Phe Pro Asp Ile Ala Leu Val Ser Val Lys Tyr
            450                 455                 460

Gln Val Asn Val Asn Gly Gln Ile Ser Gln Val Leu Gly Thr Ser Ala
465                 470                 475                 480

Ser Ser Pro Ser Met Ala Gly Leu Val Gly Leu Leu Asn Asp Tyr Arg
            485                 490                 495

Lys Thr Gln Gly Lys Pro Asn Leu Gly Phe Ile Asn Pro Leu Leu Tyr
            500                 505                 510

Ser Asp Lys Val Lys Pro Ala Leu Arg Asp Val Thr Ser Gly Ala Asn
            515                 520                 525

Lys Gly Cys Asp Ser Ser Gly Leu Pro Ala Lys Thr Gly Trp Asp Ala
            530                 535                 540

Ala Ser Gly Leu Gly Ser Phe Asp Phe Ala Lys Leu Arg Thr Leu Val
545                 550                 555                 560
```

<210> SEQ ID NO 39
<211> LENGTH: 649
<212> TYPE: PRT
<213> ORGANISM: Talaromyces proteolyticus

<400> SEQUENCE: 39

```
Met Lys Ser Ser Val Leu Leu Ser Leu Ala Ala Ser Ala Leu Ala
1               5                   10                  15

Val Pro Ala Pro Ser Lys Arg His Val His Glu Arg Arg Asp Ala
                20                  25                  30

Leu Pro His Ser Trp Ser Glu Pro Arg Arg Val Asp Gly Arg Thr Gln
                35                  40                  45

Leu Pro Val Arg Ile Gly Leu Thr Gln Ser Asn Ile Asp Glu Ser His
50                  55                  60

Asp Met Leu Met Asp Ile Ala Ser Pro Ser Pro Asn Tyr Arg Lys
65                  70                  75                  80

Tyr Met Thr Val His Glu Val Asn Glu Leu Phe Ala Pro Ala Gly Glu
                85                  90                  95

Ala Val Ser Ala Val Arg Asp Trp Leu Glu Ser Ala Gly Ile Ala Ala
                100                 105                 110

Glu Arg Val Thr Gln Ser Ala Asn Lys Gln Trp Leu Gln Phe Asp Gly
                115                 120                 125

Asp Ala Ala Glu Val Glu Ser Leu Leu Gly Ala Glu Tyr Tyr Ile Tyr
130                 135                 140

Thr His Asp Thr Asn Gly Arg Ser His Met Gly Cys Glu Lys Tyr His
145                 150                 155                 160

Val Pro Glu His Ile Ser His His Ile Asp Tyr Ile Ile Pro Gly Val
                165                 170                 175

Lys Ser Leu Glu Val Arg Glu Pro Gln Pro Ala Glu Leu Glu Lys Arg
                180                 185                 190

Thr Phe Gly Phe Arg Lys Pro Gln Pro Pro Leu Phe Lys Ala Leu Pro
                195                 200                 205

Glu Ser Leu Glu Thr Ile Ile Asn Ser Ile Leu Gly Gly Leu Leu Asp
                210                 215                 220

Leu Cys Ser Thr Val Ile Thr Pro Ser Cys Ile Lys Thr Leu Tyr Asn
225                 230                 235                 240

Ile Thr Glu Gly Thr Thr Ala Thr Lys Gly Asn Glu Leu Gly Ile Phe
                245                 250                 255

Glu Asp Leu Gly Asp Tyr Tyr Ser Gln Thr Asp Leu Asp Leu Phe Phe
                260                 265                 270

Thr Leu Phe Tyr Ser Gln Ile Pro Ala Gly Thr Gly Pro Thr Leu Lys
                275                 280                 285

Gly Ile Asp Gly Ala Gln Ala Pro Thr Gln Thr Leu Thr Gln Ala Gly
                290                 295                 300

Pro Glu Ser Asp Leu Asp Phe Gln Val Ser Tyr Pro Ile Ile Trp Pro
305                 310                 315                 320

Gln Asn Ser Ile Leu Phe Gln Thr Asp Asp Ala Asn Tyr Glu Ala Asn
                325                 330                 335

Tyr Thr Phe Asn Gly Phe Leu Asn Asn Phe Leu Asp Ala Ile Asp Gly
                340                 345                 350

Ser Tyr Cys Thr Tyr Ser Ala Phe Gly Ile Asp Gly Asn Thr Ala Asp
                355                 360                 365

Asp Pro Pro Tyr Pro Asp Pro Ala Ser Asn Gly Tyr Lys Gly Ser Leu
                370                 375                 380
```

-continued

```
Gln Cys Gly Val Tyr Glu Pro Thr Asn Val Ile Ser Ile Ser Tyr Gly
385                 390                 395                 400

Gly Asp Glu Ala Gly Leu Ser Val Asn Tyr Gln Lys Arg Gln Cys Asn
            405                 410                 415

Glu Tyr Lys Lys Leu Gly Leu Gln Gly Val Ser Val Val Ser Ser
            420                 425                 430

Gly Asp Ser Gly Val Ala Gly Ala Asp Gly Cys Leu Gly Gly Gly Lys
            435                 440                 445

Ile Phe Asn Pro Asp Phe Pro Ala Gly Cys Pro Tyr Ile Thr Thr Val
            450                 455                 460

Gly Ala Thr Tyr Leu Pro Ser Gly Ala Ser Ser Thr Ser Asp Ser Glu
465                 470                 475                 480

Val Ala Val Ser Arg Phe Pro Ser Gly Gly Gly Phe Ser Asn Ile Tyr
                485                 490                 495

Ser Gln Pro Ser Tyr Gln Ser Asp Ala Val Asn Thr Tyr Leu Thr Gln
                500                 505                 510

His Thr Pro Pro Tyr Pro Ala Tyr Glu Thr Ser Asp Asn Ser Ser Val
            515                 520                 525

Gly Ala Asn Gly Gly Ile Tyr Asn Lys Ala Gly Arg Gly Tyr Pro Asp
530                 535                 540

Val Ala Ala Val Gly Asp Asn Ile Val Ile Phe Asn Ala Gly Ala Pro
545                 550                 555                 560

Thr Leu Ile Gly Gly Thr Ser Ala Ser Ala Pro Ile Phe Ala Ser Ile
                565                 570                 575

Leu Thr Arg Ile Asn Glu Val Leu Leu Ala Lys Lys Gly Thr Thr Val
            580                 585                 590

Gly Phe Val Asn Pro Thr Leu Tyr Ala Asn Pro Asp Ala Phe His Asp
            595                 600                 605

Ile Thr Ser Gly Asp Asn Pro Gly Cys Ser Thr Asn Gly Phe Ser Thr
            610                 615                 620

Ala Pro Gly Trp Asp Pro Val Thr Gly Leu Gly Thr Pro Asn Tyr Pro
625                 630                 635                 640

Ala Leu Leu Lys Val Phe Leu Gly Glu
                645
```